US010683557B2

(12) United States Patent
Chim et al.

(10) Patent No.: US 10,683,557 B2
(45) Date of Patent: Jun. 16, 2020

(54) DETECTING BACTERIAL TAXA FOR PREDICTING ADVERSE PREGNANCY OUTCOMES

(71) Applicant: THE CHINESE UNIVERSITY OF HONG KONG, Shatin, N.T., Hong Kong (CN)

(72) Inventors: Stephen Siu-Chung Chim, Quarry Bay (CN); Chee-Yin Cheung, Tai Po (CN); Wan-Chee Cheung, Shaukeiwan (CN); Meng Meng, Shanghai (CN); Tak-Yeung Leung, Shatin (CN); Keun-Young Lee, Seoul (KR)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 15/317,021

(22) PCT Filed: Jun. 23, 2015

(86) PCT No.: PCT/CN2015/082044
§ 371 (c)(1),
(2) Date: Dec. 7, 2016

(87) PCT Pub. No.: WO2016/000539
PCT Pub. Date: Jan. 7, 2016

(65) Prior Publication Data
US 2017/0114396 A1 Apr. 27, 2017

Related U.S. Application Data

(60) Provisional application No. 62/018,920, filed on Jun. 30, 2014.

(51) Int. Cl.
C12Q 1/68 (2018.01)
C12Q 1/689 (2018.01)
C12Q 1/6883 (2018.01)

(52) U.S. Cl.
CPC .......... *C12Q 1/689* (2013.01); *C12Q 1/6883* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2001/0051344 A1* 12/2001 Shalon .................. B01L 3/0244
435/6.11

FOREIGN PATENT DOCUMENTS

WO 199/39007 A1 8/1999
WO 2002/095410 A1 11/2002

OTHER PUBLICATIONS

Enard et al. (Science 2002 vol. 296 p. 340) (Year: 2002).*
Cobb et al (Crit Care Med 2002 vol. 30 p. 2711 (Year: 2002).*
Kroese et al. (Genetics in Medicine, vol. 6 (2004), p. 475-480) (Year: 2004).*
Lucentini (The Scientist, 2004, vol. 18, p. 20) (Year: 2004).*
Romero et al. (Microbiome May 27, 2014 vol. 2 p. 18) (Year: 2014).*
Marrazzo et al. (Anaerobe 2011 vol. 17 p. 186) (Year: 2011).*
Zhou et al. (Microbiology 2004 vol. 150 p. 2565) (Year: 2004).*
Lamont et al. (BJOG 2011 p. 535) (Year: 2011).*
Jost (Apr. 2014 Curr Microbiol vol. 68 p. 419) (Year: 2014).*
Nelson et al., "Early Pregnancy Changes in Bacterial Vaginosis-Associated Bacteria and Preterm Delivery," Paediatric and Perinatal Epidemiology, 2014, 28, 88-96.
Nelson et al., "Preterm Labor and Bacterial Vaginosis-Associated Bacteria Among Urban Women," J. Perinat. Med. 37 (2009) 130-134.
Office Action in JP2017-500020 dated Jan. 16, 2018.
Jones et al., "Differing Prevalence and Diversity of Bacterial Species in Fetal Membranes from Very Preterm and Term Labor," PLoS One 4, No. 12 (2009): e8205.
Aagaard, et al., "A Metagenomic Approach to Characterization of the Vaginal Microbiome Signature in Pregnancy," PLoS One, vol. 7, No. 6, Jun. 30, 2012, e36466.
Claesson et al., "Comparison of Tow Next-Generation Sequencing Technologies for Resolving Highly Complex Microbiota Composition Using Tandem Variable 16S rRNA Gene Regions," Nucleac Acids Research, vol. 38, No. 22, Dec. 30, 2010, pp. 1-13.
Gajer et al., "Temporal Dynamics of the Human Vaginal Microbiota," Sci Trans Med, vol. 132, No. 4, May 2, 2012, pp. 132-152.
Gerber et al, "Detection of Ureaplasma Urealyticum in Second-Trimester Amniotic Fluid by Polymerase Chain Reaction Correlates with Subsequent Preterm Labor and Delivery," J Infect Dis, vol. 187, No. 3, Feb. 1, 2003, pp. 518-521.
Gray et al., "Adverse Outcome in Pregnancy Following Amniotic Fluid Isolation of Ureaplasma Urealyticum," Prenatal Diagnosis, vol. 12, No. 2, Dec. 31, 1992, pp. 111-117.
Perni et al., "Mycoplasma Hominis and Ureaplasma Urealyticum in Midtrimster Amniotic Fluid: Association with Amniotic Fluid Cytokine Levels and Pregnancy Outcome," American Journal of Obstetrics and Gynecology, vol. 191, No. 4, Dec. 31, 2004, pp. 1382-1386.
Wang et al., "Diversity of Human Vaginal Bacterial Communities in Healthy Women and Bacterial Vaginosis," Labeled Immunoassays & Clin Med, vol. 18, No. 6, Dec. 31, 2011, pp. 402-407.
Xu et al., "Illumina Sequencing 16S rRNA Tagging Reveals Diverse Vaginal Microbiomes Associated with Bacterial Vaginosis," J. South Med. Univ., vol. 33, No. 5, May 10, 2013, pp. 672-677.

(Continued)

Primary Examiner — Katherine D Salmon
(74) Attorney, Agent, or Firm — Kilpatrick Townsend & Stockton LLP

(57) ABSTRACT

It provides a method for predicting the risk of an adverse pregnancy or neonatal outcome for a pregnant subject by detecting the elevated level of bacteria from one or more selected bacterial taxa (e.g., genera or species). A kit useful for such a method is also provided. In addition, it provides a method for determining the risk of having advanced cervical dilation and/or premature cervical shortening based on differentially abundant bacterial taxa.

7 Claims, 2 Drawing Sheets
Specification includes a Sequence Listing.

(56) References Cited

OTHER PUBLICATIONS

International Search Report in PCT/CN2015/082044, dated Sep. 18, 2015.
Aagaard et al., "The Placenta Harbors a Unique Microbiome," Sci Transl Med vol. 6, 237ra65 (May 21, 2014).
Hummelen et al., "Deep Sequencing of the Vaginal Microbiota of Women with HIV," PLoS One, Aug. 2010, vol. 5, Issue 8, e12078, 9 pages.
Oh et al., "Detection of Ureaplasmas by the Polymerase Chain Reaction in the Amniotic Fluid of Patients with Cervical Insufficiency," J. Perinat. Med. 38 (2010) 261-268.
Owen et al., "Multicenter Randomized Trial of Cerclage for Preterm Birth Prevention in High-Risk Women with Shortened Midtrimester Cervical Length," American Journal of Obstetrics & Gynecology, Oct. 2009, 375.e1-375.e8.
Quince et al., "Acurate Determination of Microbial Diversity from 454 Pyrosequencing Data," Nature Methods, vol. 6, No. 9, Sep. 2009.
Ravel et al., "Vaginal Microbiome of Reproductive-Age Women," PNAS, Mar. 15, 2011, vol. 108, Suppl. 1, 4680-4687.
Romero et al., "Microbial Invasion of the Amniotic Cavity in Patients with Suspected Cervical Incompetence: Prevalence and Clinical Significance," Am J Obstet Gynecol, Oct. 1992, vol. 167, No. 4, Pt. 1, 1086-1091.
Schloss et al., "Introducing Mothur: Open-Source, Platform-Independent, Community-Supported Software for Describing and Comparing Microbial Communities," Applied and Environmental Microbiology, Dec. 2009, vol. 75, No. 23 7537-7541.
Storey et al., "Statistical Significance for Genomewide Studies," PNAS, vol. 100, No. 16, Aug. 5, 2003, 9440-9445.
Wang et al., "Naïve Bayesian Classifier for Rapid Assignment for rRNA Sequences into the New Bacterial Taxonomy," Applied and Environmental Microbiology, vol. 73, No. 16, Aug. 2007, 5261-5267.
White, et al., "Statistical Methods for Detecting Differentially Abundant Features in Clinical Metagenomic samples," PLoS Computational Biology, Apr. 2009, vol. 5, Issue 4, e1000352.
Yuan et al., Evaluation of Methods for the Extraction and Purification of DNA from the Human Microbiome, PLoS One, Mar. 2012, vol. 7, Issue 3, e33865.
Kataoka, et al. "Association between preterm birth and vaginal colonization by mycoplasmas in early pregnancy." Journal of clinical microbiology 44, No. 1 (2006): 51-55.
Larsen, et al. "Mycoplasma, Ureaplasma, and adverse pregnancy outcomes: a fresh look." Infectious diseases in obstetrics and gynecology 2010 (2010).

* cited by examiner

FIG. 1A

| Outcomes after treatment | P1 | P2 | P3 | P4 | P5 | P6 | P7 | P8 | P9 | P10 | P11 | P12 | P13 | P14 | P15 | P16 | P17 | P18 | P19 | P20 | P21 | P22 | P23 | P24 | P25 |
|---|---|---|---|---|---|---|---|---|---|---|---|---|---|---|---|---|---|---|---|---|---|---|---|---|---|
| Spontaneous preterm birth (sPTB) or Term Birth (TB) | sPTB | sPTB | sPTB | sPTB | sPTB | sPTB | sPTB | sPTB | sPTB | sPTB | TB | TB | TB | TB | TB | TB | TB | TB | TB | TB | TB | TB | TB | TB | TB |
| GA at delivery (weeks) | 18 | 20 | 21 | 21 | 24 | 24 | 25 | 26 | 31 | 33 | 38 | 38 | 38 | 38 | 38 | 38 | 38 | 39 | 39 | 40 | 40 | 40 | 40 | 40 | 41 |
| Latency (days) | 32 | 10 | 7 | 7 | 24 | 8 | 34 | 9 | 51 | 129 | 131 | 129 | 108 | 105 | 146 | 158 | 171 | 119 | 112 | 109 | 126 | 134 | 139 | 104 | 129 |
| Perinatal death | YES | YES | YES | YES | YES | no | no | no | YES | no | no | no | no | no | no | no | no | no | no | no | no | no | no | no | no |
| RDS/BPD | + | + | + | Y/Y | Y/Y | Y/N | + | + | Y/N | + | + | + | + | + | + | + | + | N/N | + | + | + | + | + | N/N | + |
| ROP/IVH | + | + | + | Y/Y | Y/Y | N/N | + | + | Y/Y | + | + | + | + | + | + | + | + | N/N | + | + | + | + | + | N/N | + |

FIG. 1B

The 10 most abundant bacteria in the "sPTB after treatment" CI cervices.

| Taxon | Operational Taxonomic Unit | sPTB | sPTB | sPTB | sPTB | sPTB | sPTB | sPTB | sPTB | sPTB | sPTB | TB | TB | TB | TB | TB | TB | TB | TB | TB | TB | TB | TB | TB | TB | TB | p value (*, FDR < 5%) |
|---|---|---|---|---|---|---|---|---|---|---|---|---|---|---|---|---|---|---|---|---|---|---|---|---|---|---|---|
| Gardnerella | Otu 4 | 2.3 | 3.5 | 4.1 | 4.1 | 0 | 5.7 | 2.4 | 4.6 | 4.1 | 5.7 | 2.7 | 3.1 | 2.5 | 1.7 | 2.5 | 2.0 | 2.5 | 0 | 0 | 0 | 2.0 | 5.8 | 2.7 | 2.0 | 0 | 0.022 |
| L.iners | Otu 2 | 2.6 | 2.7 | 5.9 | 2.9 | 0 | 3.7 | 2.4 | 4.3 | 5.8 | 3.0 | 0 | 5.7 | 2.3 | 0 | 2.4 | 6.3 | 2.6 | 6.3 | 0 | 0 | 6.3 | 2.5 | 2.0 | 6.5 | 2.3 | 0.403 |
| L.crispatus | Otu 1 | 8.2 | 1.9 | 2.7 | 3.9 | 6.3 | 0 | 1.7 | 1.7 | 3.1 | 2.5 | 5.3 | 1.7 | 5.7 | 8.3 | 6.3 | 0 | 6.2 | 3.2 | 5.8 | 6.2 | 2.3 | 0 | 6.2 | 2.9 | 5.8 | 0.183 |
| Sneathia | Otu 11 | 2.0 | 5.5 | 0 | 3.8 | 0 | 1.4 | 1.7 | 4.8 | 4.7 | 0 | 0 | 0 | 2.1 | 0 | 0 | 0 | 0 | 0 | 0 | 0 | 0 | 0 | 0 | 2.6 | 1.7 | 0.019 * |
| Sneathia | Otu 10 | 0 | 3.4 | 0 | 5.5 | 0 | 1.4 | 2.2 | 5.0 | 3.8 | 0 | 1.8 | 0 | 0 | 1.8 | 0 | 0 | 2.0 | 0 | 0 | 2.4 | 0 | 2.0 | 0 | 0 | 0.077 |
| Aerococcus | Otu 6 | 0 | 0 | 0 | 2.7 | 0 | 3.4 | 2.0 | 3.3 | 3.9 | 5.7 | 0 | 3.2 | 0 | 0 | 0 | 0 | 0 | 0 | 0 | 0 | 1.5 | 0 | 0 | 3.1 | 0 | 0.024 |
| Megasphaera | Otu 15 | 0 | 2.3 | 0 | 4.3 | 0 | 3.7 | 0 | 4.6 | 3.6 | 0 | 0 | 0 | 0 | 0 | 0 | 0 | 0 | 0 | 0 | 2.0 | 0 | 1.7 | 0 | 0 | 0.023 |
| Pseudomonas | Otu 26 | 0 | 2.3 | 2.2 | 0 | 2.1 | 2.5 | 2.8 | 2.3 | 2.6 | 1.6 | 1.8 | 1.7 | 1.8 | 0 | 0 | 4.1 | 0 | 2.5 | 1.9 | 2.0 | 2.7 | 2.2 | 2.4 | 0 | 2.5 | 0.576 |
| Anaerococcus | Otu 18 | 0 | 3.0 | 0 | 4.5 | 1.8 | 2.4 | 0 | 3.3 | 3.1 | 0 | 1.8 | 0 | 2.1 | 0 | 0 | 0 | 0 | 0 | 1.9 | 0 | 0 | 2.0 | 0 | 0 | 2.0 | 0.067 |
| L.gasseri | Otu 3 | 0 | 0 | 3.0 | 1.3 | 0 | 1.4 | 6.1 | 3.2 | 1.8 | 0 | 2.1 | 1.7 | 1.8 | 2.2 | 2.0 | 3.3 | 0 | 0 | 0 | 0 | 0 | 2.9 | 0 | 0 | 2.9 | 0.794 |

FIG. 1C

The 10 most abundant bacteria in the "TB after treatment" CI cervices.

| Taxon | Operational Taxonomic Unit | sPTB | sPTB | sPTB | sPTB | sPTB | sPTB | sPTB | sPTB | sPTB | sPTB | TB | TB | TB | TB | TB | TB | TB | TB | TB | TB | TB | TB | TB | TB | TB | p value (*, FDR < 5%) |
|---|---|---|---|---|---|---|---|---|---|---|---|---|---|---|---|---|---|---|---|---|---|---|---|---|---|---|---|
| L.crispatus | Otu 1 | 8.2 | 1.9 | 2.7 | 3.9 | 6.3 | 0 | 1.7 | 1.7 | 3.1 | 2.5 | 5.3 | 1.7 | 5.7 | 8.3 | 6.3 | 0 | 6.2 | 3.2 | 5.8 | 6.2 | 2.3 | 0 | 6.2 | 2.9 | 5.8 | 0.183 |
| L.iners | Otu 2 | 2.6 | 2.7 | 5.9 | 2.9 | 0 | 3.7 | 2.4 | 4.3 | 5.8 | 3.0 | 0 | 5.7 | 2.3 | 0 | 2.4 | 6.3 | 2.6 | 6.3 | 0 | 0 | 6.3 | 2.5 | 2.0 | 6.5 | 2.3 | 0.403 |
| L.jensenii | Otu 5 | 2.3 | 0 | 4.9 | 0 | 0 | 0 | 0 | 0 | 0 | 0 | 4.6 | 0 | 3.3 | 0 | 2.2 | 0 | 4.1 | 5.0 | 3.3 | 0 | 5.4 | 2.6 | 0 | 0 | 0 | 0.103 |
| Gardnerella | Otu 4 | 2.3 | 3.5 | 4.1 | 4.1 | 0 | 5.7 | 2.4 | 4.6 | 4.1 | 5.7 | 2.7 | 3.1 | 2.5 | 1.7 | 2.5 | 2.0 | 2.5 | 0 | 0 | 0 | 2.0 | 5.8 | 2.7 | 2.0 | 0 | 0.022 |
| Pseudomonas | Otu 26 | 0 | 2.3 | 2.2 | 0 | 2.1 | 2.5 | 2.8 | 2.3 | 2.6 | 1.8 | 1.8 | 1.7 | 1.8 | 0 | 0 | 4.1 | 0 | 2.5 | 1.9 | 2.0 | 2.7 | 2.2 | 2.4 | 0 | 2.5 | 0.576 |
| L.vaginalis | Otu 19 | 0 | 0 | 2.7 | 0 | 0 | 0 | 0 | 0 | 0 | 0 | 0 | 0 | 3.5 | 0 | 1.8 | 0 | 3.5 | 0 | 3.2 | 2.9 | 4.0 | 0 | 0 | 0 | 3.9 | 0.052 |
| L.gasseri | Otu 3 | 0 | 0 | 3.0 | 1.3 | 0 | 1.4 | 6.1 | 3.2 | 1.8 | 0 | 2.1 | 1.7 | 1.8 | 2.2 | 2.0 | 3.3 | 0 | 0 | 0 | 0 | 0 | 2.9 | 0 | 0 | 2.9 | 0.794 |
| Corynebacterium | Otu 44 | 2.0 | 0 | 0 | 0 | 0 | 0 | 0 | 0 | 0 | 0 | 0 | 0 | 2.1 | 0 | 0 | 0 | 2.3 | 2.1 | 2.3 | 0 | 2.0 | 0 | 0 | 1.7 | 0 | 0.108 |
| Sneathia | Otu 10 | 0 | 3.4 | 0 | 5.5 | 0 | 1.4 | 2.2 | 5.0 | 3.8 | 0 | 1.8 | 0 | 0 | 2 | 1.8 | 0 | 0 | 2.0 | 0 | 0 | 2.4 | 0 | 2.0 | 0 | 0 | 0.077 |
| Anaerococcus | Otu 18 | 0 | 3.0 | 0 | 4.5 | 1.8 | 2.4 | 0 | 3.3 | 3.1 | 0 | 1.8 | 0 | 2.1 | 0 | 0 | 0 | 0 | 0 | 1.9 | 0 | 0 | 2.0 | 0 | 0 | 2.0 | 0.067 |

FIG. 1D

Differentially abundant bacteria between the "sPTB after treatment" and the "TB after treatment" CI cervices.

| Taxon | Operational Taxonomic Unit | sPTB | sPTB | sPTB | sPTB | sPTB | sPTB | sPTB | sPTB | sPTB | sPTB | TB | TB | TB | TB | TB | TB | TB | TB | TB | TB | TB | TB | TB | TB | TB | p value (*, FDR < 5%) |
|---|---|---|---|---|---|---|---|---|---|---|---|---|---|---|---|---|---|---|---|---|---|---|---|---|---|---|---|
| Sneathia | Otu 11 | 2.0 | 5.5 | 0 | 3.8 | 0 | 1.4 | 1.7 | 4.8 | 4.7 | 0 | 0 | 0 | 2.1 | 0 | 0 | 0 | 0 | 0 | 0 | 0 | 0 | 0 | 0 | 2.6 | 1.7 | 0.019 * |
| Parvimonas | Otu 16 | 0 | 0 | 0 | 4.5 | 0 | 3.7 | 2.0 | 4.4 | 0 | 0 | 0 | 0 | 0 | 0 | 0 | 0 | 0 | 0 | 0 | 0 | 0 | 0 | 0 | 0 | 0 | 0.009 * |
| Ureaplasma | Otu 58 | 2.3 | 0 | 2.4 | 0 | 2.8 | 0 | 0 | 3.1 | 0 | 0 | 0 | 0 | 0 | 0 | 0 | 0 | 0 | 0 | 0 | 0 | 0 | 0 | 0 | 0 | 0 | 0.009 * |
| Atopobium | Otu 42 | 0 | 0 | 0 | 2.7 | 0 | 1.9 | 0 | 2.9 | 2.4 | 0 | 0 | 0 | 0 | 0 | 0 | 0 | 0 | 0 | 0 | 0 | 0 | 0 | 0 | 0 | 0 | 0.009 * |
| Peptoniphilus | Otu 28 | 0 | 0 | 0 | 0 | 0 | 2.3 | 2.0 | 3.7 | 1.8 | 0 | 0 | 0 | 0 | 0 | 0 | 0 | 0 | 0 | 0 | 0 | 0 | 0 | 0 | 0 | 0 | 0.009 * |
| Megasphaera | Otu 47 | 0 | 0 | 0 | 2.8 | 0 | 2.6 | 0 | 1.4 | 2.6 | 0 | 0 | 0 | 0 | 0 | 0 | 0 | 0 | 0 | 0 | 0 | 0 | 0 | 0 | 0 | 0 | 0.009 * |
| Parvegerhella | Otu 40 | 0 | 1.4 | 0 | 2.0 | 0 | 3.0 | 0 | 2.4 | 0 | 0 | 0 | 0 | 0 | 0 | 0 | 0 | 0 | 0 | 0 | 0 | 0 | 0 | 0 | 0 | 0 | 0.009 * |

FIG. 1E

| Normalized read counts: | log (abundance): |
|---|---|
| >10,000 | > 4.0 |
| >1,000 to 10,000 | > 3.0 to 4.0 |
| >100 to 1,000 | > 2.0 to 3.0 |
| >10 to 100 | > 1.0 to 2.0 |
| >1 to 10 | > 0.5 to 1.0 |
| 1 | 0 |

SEQUENCE LISTING

<160> NUMBER OF SEQ ID NOS: 57

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: a, c, t, g, unknown or other

<400> SEQUENCE: 1
aytgggydta aagng                                                15

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgtcaatty ytttragttt                                           20

<210> SEQ ID NO 3
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 3
ggagcgcagg cggttttttta agtctgatgt gaaagccctc ggcttaaccg aggaagcgca    60
tcggaaactg ggaaacttga gtgcagaaga ggacagtgga actccatgtg tagcggtgaa   120
atgcgtagat atatggaaga acaccagtgg cgaaggcggc tgtctggtct gtaactgacg   180
ct                                                                  182

<210> SEQ ID NO 4
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 4
cgcgcgcagg cggactagcc agtcagtctt aaaagttcgg ggcttaaccc cgtgatggga    60

```
ttgaaactac tagtctagag tatcggagag gaaagtggaa ttcctagtgt agcggtgaaa      120
tgcgtagata ttaggaagaa caccagtggc gaaggcgact ttctggacga acactgacgc      180
t                                                                     181

<210> SEQ ID NO 5
<211> LENGTH: 178
<212> TYPE: DNA
<213> ORGANISM: Unknown
<220> FEATURE:
<223> OTHER INFORMATION: Description of Unknown:
      16S ribosomal RNA sequence

<400> SEQUENCE: 5
ggcgcgcagg cggttcggta agtctgtctt aaagtgcggg cttaaccccg tgagggacgg       60
aaactgtcga acttgagtgt cggagaggaa agcggaattc ctagtgtagc ggtgaaatgc      120
gtagatatta ggaggaacac cggtggcgaa agcggctttc tggacgacaa ctgacgct       178

<210> SEQ ID NO 6
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 6
agatgagatg gcggtttgtc gcgtctggtg tgaaagtcca tcgcttaacg gtggattggc       60
gctgggtacg ggcaggctag agtgtagtag gggagactgg aattctcggt gtaacggtgg      120
aatgtgtaga tatcgggaag aacaccaatg gcgaaggcag gtctctgggc tattactgac      180
gct                                                                   183

<210> SEQ ID NO 7
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 7
cgagcgcagg cgggtttgta agtttggtat taaatctaga tgcttaacgt ctagctgtat       60
caaaaactgt aaacctagag tgtagtaggg agttggggaa ctccatgtgg agcggtaaaa      120
tgcgtagata tatggaagaa caccggtggc gaaggcgcca acttggacta tcactgacgc      180
t                                                                     181

<210> SEQ ID NO 8
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 8
cgcgcgtagg cggtctgtta ggtcaggagt caaatctggg ggctcaaccc ctatccgctc       60
ctgataccgg caggcttgag tctggtatgg gaaggtggaa ttccaagtgt agcggtgaaa      120
tgcgcagata tttggaagaa caccagtggc gaaggcggcc ttctgggcca tgactgacgc      180
t                                                                     181
```

<210> SEQ ID NO 9
<211> LENGTH: 181
<212> TYPE: DNA
<213> ORGANISM: Unknown
<220> FEATURE:
<223> OTHER INFORMATION: Description of Unknown:
    16S ribosomal RNA sequence

<400> SEQUENCE: 9

```
cgcgcgcagg cggttgctca agcggaacct ctaatctcgg ggcttaacct cgagccgggt      60
tccgaactgg acgactcgag tgcggtagag gcagatggaa ttcccggtgt agcggtggaa     120
tgcgcagata tcgggaagaa caccaacggc gaaggcagtc tgctgggccg tcactgacgc     180
t                                                                    181
```

<210> SEQ ID NO 10
<211> LENGTH: 181
<212> TYPE: DNA
<213> ORGANISM: Unknown
<220> FEATURE:
<223> OTHER INFORMATION: Description of Unknown:
    16S ribosomal RNA sequence

<400> SEQUENCE: 10

```
agtacgtagg cggcctagta agttagaagt gaaagaatat agctcaacta tataaagctt      60
ttaaaactgt taggcttgag agatgaaagg gaaagtggaa ttcctagtgt agcggtgaaa     120
tgcgcagata ttaggaagaa taccggtggc gaaggcgact ttctggtcat catctgacgc     180
t                                                                    181
```

<210> SEQ ID NO 11
<211> LENGTH: 181
<212> TYPE: DNA
<213> ORGANISM: Unknown
<220> FEATURE:
<223> OTHER INFORMATION: Description of Unknown:
    16S ribosomal RNA sequence

<400> SEQUENCE: 11

```
ggtgcgtagg cggtctgtta agttcatggt taaattttgg ggctcaaccc cattgagcca      60
tggatactgg cagactagag tattggagag gcaagcggaa ttccatgtgt agcggtaaaa     120
tgcgtagata tatggaggaa caccggtggc gaaggcggct tgctagccaa agactgacgc     180
t                                                                    181
```

<210> SEQ ID NO 12
<211> LENGTH: 182
<212> TYPE: DNA
<213> ORGANISM: Unknown
<220> FEATURE:
<223> OTHER INFORMATION: Description of Unknown:
    16S ribosomal RNA sequence

<400> SEQUENCE: 12

```
ggtgcgcagg cggctttaca agttggatgt gaaatattgt ggctcaacca caaacgtgca      60
tccaaaactg caaagcttga gttaaggaga ggtaagtgga attcctggtg tagcggtgga     120
atgcgtagat atcaggagga ataccggtgg cgaaggcgac ttactggact aaaactgacg     180
ct                                                                   182
```

<210> SEQ ID NO 13

<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 13
ggcgcgtagg cggaatggca agtcagcaag tgaaagcgtg gggctcaacc ccatgatgcg    60
gctgaaactg ttattctaga ggcatggaga ggcaaacgga attcccggtg tagcggtgaa   120
atgcgtagat atcgggaaga acaccagtgg cgaaggcggt ttgctggcca tgaactgacg   180
ct                                                                 182

<210> SEQ ID NO 14
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 14
tgggcgcagg cggtttctta agtctgatgt gaaagcccac ggcttaaccg tggaagtgca    60
ttggaaactg ggaacttga gtacagaaga ggaaagtgga actccatgtg tagcggtgga   120
atgcgtagat atatggaaga acaccagtgg cgaaggcgac tttctggtct gtcactgacg   180
ct                                                                 182

<210> SEQ ID NO 15
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 15
cgttcgcagg cggcaatgca agtctcgtgt gaaaggcaag ggctcaaccc ttgtaagcac    60
aagaaactgc atagcttgag tagtggagag gcaagtggaa ttcctagtgt agcggtgaaa   120
tgcgtagata ttaggaggaa taccggtggc gaaggcgact tgctggacac aaactgacgc   180
t                                                                  181

<210> SEQ ID NO 16
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 16
ggctcgtagg tggtttgtcg cgtcgtctgt gaaattccgg ggcttaactc cgggcgtgca    60
ggcgatacgg gcataacttg agtactgtag gggagactgg aattcctggt gtagcggtga   120
aatgcgcaga tatcaggagg aacaccggtg gcgaaggcgg gtctctgggc agtaactgac   180
gct                                                                183

<210> SEQ ID NO 17
<211> LENGTH: 182
<212> TYPE: DNA
<213> ORGANISM: Unknown

<220> FEATURE:
<223> OTHER INFORMATION: Description of Unknown:
      16S ribosomal RNA sequence

<400> SEQUENCE: 17
cgcgtgtagg cggattctca agttggatgt gaaacccctt ggctaaactg agggcttgca      60
ttcaaaactg aggaccttga gtatcagagg ggaaagtgga attcctggtg gagcggtaaa     120
atgcgtagag atcaggagga acaccggtgg cgaaggcgac tttctggctg acaactgacg     180
ct                                                                    182

<210> SEQ ID NO 18
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 18
tgtgtgtagg tggcgtgatt agtcgtttgt gaaagatccg agcttaactt ggaaaacgcg      60
aacgaaacgg tcatgcttga gtatgtgaga ggtaagcaga actcatggtg tagggtgaa     120 atccgttgat atcatgggga ataccaaaag cgaaggcagc ttactggcac attactgaca     180
ct                                                                    182

<210> SEQ ID NO 19
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 19
ggttcgtagg ctgtttgtta agtctggagt taaatcccgg ggctcaaccc cggctcgctt      60
tggatactag caaactagag ttagatagag gtaagcggaa ttccatgtga agcggtgaaa     120
tgcgtagata tatggaagaa caccaaaggc gaaggcagct tactgggtct atactgacgc     180
t                                                                     181

<210> SEQ ID NO 20
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 20
cgcgcgcagg cggactagcc agtcagtctt aaaagttcgg ggcttaaccc cgtgatggga      60
ttgaaactac tagtctagag tatcggagag gaaagtggaa ttcctagtgt agcggtgaaa     120
tgcgtagata ttaggaagaa caccagtggc gaaggcgact ttctggacga acactgacgc     180
t                                                                     181

<210> SEQ ID NO 21
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 21

```
agatgagatg gcggtttgtc gcgtctggtg tgaaagtcca tcgcttaacg gtggattggc    60
gctgggtacg ggcaggctag agtgtagtag gggagactgg aattctcggt gtaacggtgg   120
aatgtgtaga tatcgggaag aacaccaatg gcgaaggcag gtctctgggc tattactgac   180
gct                                                                 183
```

<210> SEQ ID NO 22
<211> LENGTH: 181
<212> TYPE: DNA
<213> ORGANISM: Unknown
<220> FEATURE:
<223> OTHER INFORMATION: Description of Unknown:
    16S ribosomal RNA sequence

<400> SEQUENCE: 22

```
agtacgtagg cggcctagta agttagaagt gaaagaatat agctcaacta tataaagctt    60
ttaaaactgt taggcttgag agatgaaagg gaaagtggaa ttcctagtgt agcggtgaaa   120
tgcgcagata ttaggaagaa taccggtggc gaaggcgact ttctggtcat catctgacgc   180
t                                                                   181
```

<210> SEQ ID NO 23
<211> LENGTH: 181
<212> TYPE: DNA
<213> ORGANISM: Unknown
<220> FEATURE:
<223> OTHER INFORMATION: Description of Unknown:
    16S ribosomal RNA sequence

<400> SEQUENCE: 23

```
ggcttgtagg cggtttgtcg cgtcgaaagt gtaaactcag tgcttaacgc tgagcctgct    60
ttcgatacgg gctgactaga ggaaggtagg ggagaatgga attcccggtg gagcggtgga   120
atgcgcagat atcgggagga acaccagtgg cgaaggcggt tctctggacc tttcctgacg   180
c                                                                   181
```

<210> SEQ ID NO 24
<211> LENGTH: 181
<212> TYPE: DNA
<213> ORGANISM: Unknown
<220> FEATURE:
<223> OTHER INFORMATION: Description of Unknown:
    16S ribosomal RNA sequence

<400> SEQUENCE: 24

```
cgctcgtagg tggtgtgttg cgtcgtctgt gtaatccagg ggcttaactt ttggttggca    60
ggcgatacgg gcattgcttg agtgctgtag gggagactgg aattcctggt gtagcggtga   120
aatgcgcaga tatcaggagg aacaccgatg gcgaaggcag gtctctgggc agttactgac   180
g                                                                   181
```

<210> SEQ ID NO 25
<211> LENGTH: 182
<212> TYPE: DNA
<213> ORGANISM: Unknown
<220> FEATURE:
<223> OTHER INFORMATION: Description of Unknown:
    16S ribosomal RNA sequence

<400> SEQUENCE: 25

```
tgagcgtagg cggcagtaca agtcgggagt gaaaactcgg ggctcaaccc cgagactgct    60
ctcgaaactg tacagctaga gtgcaggatg ggcaggcgga attcctggtg tagcggtgaa   120
atgcgtagat atcaggagga acaccggtgg cgaaggcggc ctgctggact gtaactgacg   180
ct                                                                  182
```

<210> SEQ ID NO 26
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 26

```
ggcttgtagg cggcttgttg cgcctgctgt gaaaacgcgg ggcttaactt cgcgcgtgca    60
gtgggtacgg gcaggcttga gtgtggtagg ggtgactgga attccaggtg tagcggtgga   120
atgcgcagat atctggagga acaccgatgg cgaaggcagg tcactgggcc attactgacg   180
ct                                                                  182
```

<210> SEQ ID NO 27
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 27

```
ggtacgtagg cggtttgtta agtttggcgt taaatcacgg ggctcaaccc cgttcagcgt    60
tgaaaactgg caaacttgag tagtagaggg gacagtggaa ttcctagtgt agcggtgaaa   120
tgcgtagaga ttaggaagaa taccggtggc gaaggcgact gtctggatac atactgacgc   180
t                                                                   181
```

<210> SEQ ID NO 28
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 28

```
ggtgtgtagg cggttatatt agtcatttgt taaatcctcg ggcttaaccc gagaatcgcg    60
agcgaaacgg tataactaga aagtgtgagg ggtgtacaga actcatggtg tagggggtgaa  120 atccgttgat atcatgggga ataccaaaag cgaaggcagt acactggcac atatttgacg   180
ct                                                                  182
```

<210> SEQ ID NO 29
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 29

```
tgcgcgcagg cggttcggta agtctgtctt aaaagtgcgg ggcttaaccc cgtgagggga    60
cggaaactgt cgaacttgag tgtcggagag gaaagcggaa ttcctagtgt agcggtgaaa   120
```

```
tgcgtagata ttaggaggaa caccggtggc gaaagcggct ttctggacga caactgacgc    180
t                                                                    181

<210> SEQ ID NO 30
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 30
ggttcgcagg cggaataaca agtcagatgt gaaaggcatg ggctcaaccc atgtaagcat    60
ttgaaactgt aattcttgag aagtggagag gtaagtggaa ttcctagtgt agcggtgaaa   120
tgcgtagata ttaggaggaa tacctgtggc gaaggcgact tactggacac aaatctgacg   180
ct                                                                   182

<210> SEQ ID NO 31
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 31
cgcgtgtagg cggcactgta agtcagatgt gaaatctccc ggctcaaccg ggagcgtgca   60
tctgatactg caatgcttga gtgatagagg ggaaagcgga attcctagtg tagcggtaaa   120
atgcgtagat attaggagga acaccagtgg cgaaggcggc tttctggcta ttaactgacg   180
ct                                                                   182

<210> SEQ ID NO 32
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 32
ggtgcgtagg cggttcggta agtcttgtgt gaaatcttca ggctcaactt gaagtctgca   60
cgagaaactg ccgggcttga gtgtgggaga ggtgagtgga atttccggtg tagcggtgaa   120
atgcgtagat atcggaagga acacctgtgg cgaaagcggc tcactggacc acaactgacg   180
ct                                                                   182

<210> SEQ ID NO 33
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 33
ggtgtgtagg tggttatgtt agtctccttt caaagctccc ggcctaaccg ggaaaaggga   60
ggggaaacgg cacaactaga ggatgcgagg ggtctgtgga actcatggag tagggggtgaa   120 atccgttgat atcatgggga acaccaaaaa gcgaaggcag cagactggcg cattcctgac   180
```

```
act                                                          183

<210> SEQ ID NO 34
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 34
cgagtgcagg cggttttcta agtctgatgt gaaagccttc ggcttaaccg gagaagtgca    60
tcggaaactg gataacttga gtgcagaaga gggtagtgga actccatgtg tagcggtgga   120
atgcgtagat atatggaaga acaccagtgg cgaaggcggc tacctggtct gcaactgacg   180
ct                                                          182

<210> SEQ ID NO 35
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 35
tgggcgcagg cggttttctta agtctgatgt gaaagcccac ggcttaaccg tggaagtgca    60
ttggaaactg ggaacttga gtacagaaga ggaaagtgga actccatgtg tagcggtgga   120
atgcgtagat atatggaaga acaccagtgg cgaaggcgac tttctggtct gtcactgacg   180
ct                                                          182

<210> SEQ ID NO 36
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 36
cgttcgcagg cggcaatgca agtctcgtgt gaaaggcaag ggctcaaccc ttgtaagcac    60
aagaaactgc atagcttgag tagtggagag gcaagtggaa ttcctagtgt agcggtgaaa   120
tgcgtagata ttaggaggaa taccggtggc gaaggcgact tgctggacac aaactgacgc   180
t                                                           181

<210> SEQ ID NO 37
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 37
tgagcgcagg cggtttttta agtctgatgt gaaagccttc ggcttaaccg gagaagtgca    60
tcggaaactg ggagacttga gtgcagaaga ggacagtgga actccatgtg tagcggtgga   120
atgcgtagat atatggaaga acaccagtgg cgaaggcggc tgtctagtct gtaactgacg   180
ct                                                          182
```

```
<210> SEQ ID NO 38
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 38
ggctcgtagg tggtttgtcg cgtcgtctgt gaaattccgg ggcttaactc cgggcgtgca    60
ggcgatacgg gcataacttg agtactgtag gggagactgg aattcctggt gtagcggtga   120
aatgcgcaga tatcaggagg aacaccggtg gcgaaggcgg gtctctgggc agtaactgac   180
gct                                                                  183

<210> SEQ ID NO 39
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 39
agggcgcagg ctgtttctta agtctgatgt gaaagcccac ggcttaaccg tggaagtgca    60
ttggaaactg ggaagcttga gtacagaaga ggaaagtgga actccatgtg tagcggtgga   120
atgcgtagat atatggaaga acaccagtgg cgaaagcgac tttctggtct gtcactgacg   180
ctga                                                                 184

<210> SEQ ID NO 40
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 40
cgctcgtagg cggttcgtcg cgtccggtgt gaaagtccat cgcttaacgg tggatccgcg    60
ccgggtacgg gcgggcttga gtgcggtagg ggagactgga attcccggtg taacggtgga   120
atgtgtagat atcgggaaga acaccaatgg cgaaggcagg tctctgggcc gttactgacg   180
ctga                                                                 184

<210> SEQ ID NO 41
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 41
cgcgtgtagg cggctagata agtgtgatgt ttaaatccaa ggcttaacct tggggttcat    60
tacaaactgt ttagcttgag tgctggagag gatagtggaa ttcctagtgt agcggtaaaa   120
tgcgtagata ttaggaggaa caccggtggc gaaggcggct atctggacag taactgacgc   180
tga                                                                  183

<210> SEQ ID NO 42
<211> LENGTH: 184
<212> TYPE: DNA
```

```
<213> ORGANISM: Unknown
<220> FEATURE:
<223> OTHER INFORMATION: Description of Unknown:
      16S ribosomal RNA sequence

<400> SEQUENCE: 42
cgagcgtagg ctgtttgtta agcgtgttgt gaaatgtagg agctcaactt ttagattgca    60
gcgcgaactg gcagacttga gtgcgcacaa cgtaggcgga attcatggtg tagcggtgaa   120
atgcttagat atcatgacga actccgattg cgaaggcagc ttacgggagc gcaactgacg   180
ctaa                                                                184

<210> SEQ ID NO 43
<211> LENGTH: 182
<212> TYPE: DNA
<213> ORGANISM: Unknown
<220> FEATURE:
<223> OTHER INFORMATION: Description of Unknown:
      16S ribosomal RNA sequence

<400> SEQUENCE: 43
ggtacgtagg cggtttttaa gtcaggtgtc aaagcgtgga gcttaactcc attaagcact    60
tgaaactgaa agacttgagt gaaggagagg aaagtggaat tcctagtgta gcggtgaaat   120
gcgtagatat taggaggaat accggtggcg aaggcgactt tctggacttt tactgacgct   180
ca                                                                  182

<210> SEQ ID NO 44
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 44
tgttcgcagg cggcaatgca agtcagatgt aaaaggcaaa ggctcaacct ttgtaagcat    60
ctgaaactgt atagcttgag aagtgtagag gcaagtggaa tttttagtgt agcggtgaaa   120
tgcgtagata ttaaaagaa taccggtggc gaaggcgact tgctgggcac aatctgacgc   180
tga                                                                 183

<210> SEQ ID NO 45
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 45
agtacgtagg cggataagca agttagaagt gaaatcctat agctcaacta tagtaagctt    60
ttaaaactgc tcatcttgag gtatggaagg gaaagtggaa ttcctagtgt agcggtgaaa   120
tgcgcagata ttaggaggaa taccggtggc gaaggcgact ttctggccat aaactgacgc   180
tga                                                                 183

<210> SEQ ID NO 46
<211> LENGTH: 183
<212> TYPE: DNA
<213> ORGANISM: Unknown
<220> FEATURE:
<223> OTHER INFORMATION: Description of Unknown:
```

16S ribosomal RNA sequence

<400> SEQUENCE: 46
ggcgcgcagg cggtttttta agtcggtctt aaaagtgcgg ggcttaaccc cgtgagggga    60
ccgaaactgg aagacttgag tgtcggagag gaaagcggaa ttcctagtgt agcggtgaaa   120
tgcgtagata ttaggaggaa caccggtggc gaaagcggct ttctggacga caactgacgc   180
tga                                                                183

<210> SEQ ID NO 47
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 47
ggcgcgcagg cggtcactta agtccatctt agaagtgcgg ggcttaaccc cgtgatggga    60
tggaaactgg gagactggag tatcggagag gaaagtggaa ttcctagtgt agcggtgaaa   120
tgcgtagata ttaggaagaa caccggtggc gaaggcgact ttctggacga aaactgacgc   180
tga                                                                183

<210> SEQ ID NO 48
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 48
ggtgcgtagg tggtctttca agtcggtggt taaaggctac ggctcaaccg tagttagcct    60
ccgaaactgg aagacttgag tgcaggagag gaaagtggaa ttcccagtgt agcggtgaaa   120
tgcgtagata ttgggaggaa caccagtagc gaaggcggct ttctggactg caactgacac   180
tga                                                                183

<210> SEQ ID NO 49
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 49
ggcgtgtagg cggctagata agtgtgatgt ttaaatccaa ggcttaaacc ttggggttca    60
ttacaaactg tttagcttga gtgctggaga ggatagtgga attcctagtg tagcggtaaa   120
atgcgtagat attaggagga acaccggtgg cgaaggcggc tatctggaca gtaactgacg   180
ctga                                                               184

<210> SEQ ID NO 50
<211> LENGTH: 183
<212> TYPE: DNA
<213> ORGANISM: Unknown
<220> FEATURE:
<223> OTHER INFORMATION: Description of Unknown:
      16S ribosomal RNA sequence

<400> SEQUENCE: 50
ggcgcgtagg cggtctgtta ggtcaggagt caaatctggg ggctcaaccc ctatccgctc    60
ctgataccgg caggcttgag tctggtatgg aaggtggaa ttccaagtgt agcggtgaaa   120
tgcgcagata tttggaagaa caccagtggc gaaggcggcc ttctgggcca tgactgacgc   180
tga                                                                 183

<210> SEQ ID NO 51
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 51
gatgagatgg cggttcgtcg cgtccggtgt gaaagtccat cgcttaacgg tggatccgcg    60
ccgggtacgg gcgggcttga gtgcggtagg ggagactgga attcccggtg taacggtgga   120
atgtgtagat atcgggaaga acaccaatgg cgaaggcagg tctctgggcc gttactgacg   180
ctga                                                                184

<210> SEQ ID NO 52
<211> LENGTH: 185
<212> TYPE: DNA
<213> ORGANISM: Unknown
<220> FEATURE:
<223> OTHER INFORMATION: Description of Unknown:
      16S ribosomal RNA sequence

<400> SEQUENCE: 52
ggcaggtagg tggtctgatt agtcaatagg tgaaatcctc gggcttaacc cgagaagtgc    60
ctttgaaacg gtcagactgg agtactctag agggtcgtgg aattcccggt gtagcggtga   120
aatgcgtaga gatcgggagg aacaccagag gcgaaggcgg cgacctgggg agtgactgac   180
actca                                                               185

<210> SEQ ID NO 53
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 53
cgtgcgtagg cggttctttta agtcagaggt gaaagacggc agcttaactg tcgcagtgcc    60
tttgatactg aagaacttga attgggttga ggaatgcgga atgagacaag tagcggtgaa   120
atgcatagat atgtctcaga accccgattg cgaaggcagc attccaagcc tatattgacg   180
ctga                                                                184

<210> SEQ ID NO 54
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 54
ggcaggtagg ctgttttgta agtccggcgt gaaatcccag agctcaactc tggaactgcg    60

```
ttggaaacta catgacttga gtatcggaga ggttagggga attctcggtg taagggtgaa    120
atctgtagat atcgagagga acaccagtgg cgaaggcgcc taactggccg attactgacg    180
ctga                                                                  184

<210> SEQ ID NO 55
<211> LENGTH: 184
<212> TYPE: DNA
<213> ORGANISM: Unknown
<220> FEATURE:
<223> OTHER INFORMATION: Description of Unknown:
      16S ribosomal RNA sequence

<400> SEQUENCE: 55
agagcgcagg cggtttctta agtctgatgt gaaagccctc ggctcaaccg aggaaggtca     60
ttggaaactg gggaacttga atgcagaaga ggagagtgga attccatgtg tagcggtgaa    120
atgcgtagat atatggagga acaccagtgg cgaaggcgac tctctggtct gtaattgacg    180
ctga                                                                  184

<210> SEQ ID NO 56
<211> LENGTH: 127
<212> TYPE: DNA
<213> ORGANISM: Sneathia sanguinegens

<400> SEQUENCE: 56
cgcatctagg cggtaagaca agttgaaggt gaaaacctgt ggctcaacca taggcttgcc     60
tacaaaactg ttgaactaga gtactggaaa ggtgggtgga actacacgag tagaggtgaa    120
attcgta                                                               127

<210> SEQ ID NO 57
<211> LENGTH: 181
<212> TYPE: DNA
<213> ORGANISM: Unknown
<220> FEATURE:
<223> OTHER INFORMATION: Description of Unknown:
      16S ribosomal RNA sequence

<400> SEQUENCE: 57
ggtgcgcagg cggctttaca agttggatgt gaaatattgt ggctcaacca caaacgtgca     60
tccaaaactg caaagcttga gttaaggaga ggtaagtgga attcctggtg tagcggtgga    120
atgcgtagat atcaggagga ataccggtgg cgaaggcgac ttactggact taaactgacg    180
c                                                                     181
```

DETECTING BACTERIAL TAXA FOR PREDICTING ADVERSE PREGNANCY OUTCOMES

CROSS-REFERENCES TO RELATED APPLICATIONS

This application is a U.S. National Phase Application of PCT/CN2015/082044, international filing date Jun. 23, 2015, which the benefit to U.S. Provisional Application No. 62/018,920, filed Jun. 30, 2014, the disclosure of which is hereby incorporated by reference in its entirety for all purposes.

REFERENCE TO SUBMISSION OF A SEQUENCE LISTING AS A TEXT FILE

The Sequence Listing written in file 080015-1026306-015510US_SL.txt created on Jan. 23, 2020, 25,324 bytes, machine format IBM-PC, MS-Windows operating system, is hereby incorporated by reference in its entirety for all purposes.

BACKGROUND OF THE INVENTION

In a normal uncomplicated pregnancy, the cervix is long and closed until the late third trimester, when it will eventually shorten and dilate around the time when the fetus fully develops and is ready for birth. Contrastingly, in a pregnancy complicated by cervical shortening or advanced cervical dilation, the cervix progresses to shortening or dilation, respectively, well ahead of the normal schedule above. Consequently, certain women with these conditions will result in birth sooner than thirty-seven gestational weeks, when fetal development is incomplete. Hence, this may lead to neonatal mortality and morbidity. To prolong such pregnancy, the clinicians may place a cerclage or a cervical pessary to support the cervix. Based primarily on consensus and expert opinion, it is recommended that cerclage placement may be beneficial if intra-amniotic infection is ruled out. Similar guidelines are suggested for pessary placement. To rule out infection effectively, a highly sensitive detection method is required.

Currently, the detection of bacteria in a sample relies on culture, microscopy and bacterial species-specific polymerase chain reaction (PCR) assays, which only offer low to moderate sensitivity. Such sensitivity could be improved if we can specifically target the bacterial taxa which are differentially abundant in the abnormal (i.e., short/dilated) cervix, but not those which are only part of the "normal" flora residing in a "normal" cervix. However, to-date, there are limited data on those taxa, because the bacterial taxa in the abnormal cervix have not been systematically profiled and compared with those in the "normal" cervix from appropriately-matched women. Given the prevalence and implications of premature birth, there exists a need for new methods to more accurately detect an increased risk of an adverse pregnancy outcome in women, such that preventive measures may be timely taken to reduce or eliminate the chances of premature birth or neonatal complications. This invention fulfills this and other related needs.

BRIEF SUMMARY OF THE INVENTION

The present disclosure is based, in part, on the discovery that the level of bacteria belonging to a specific group of bacterial taxa (e.g., a bacterial species or genera) in a woman's cervix is increased in correlation with the likelihood of an adverse pregnancy outcome, such as a premature birth at less than 34 weeks or 37 weeks of gestational age, or an adverse neonatal condition, such as an Apgar score of less than 7 at 1 or 5 minutes, chorioamnionitis, respiratory distress syndrome, bronchopulmonary dysplasia, intraventricular hemorrhage, neonatal sepsis and neonatal death within 7 days of birth. As such, in a first aspect, the present invention provides a method for determining the risk of an adverse pregnancy or neonatal outcome for a subject, e.g., a pregnant woman or a non-pregnant woman. The method includes the steps of (a) detecting in a biological sample taken from the subject the level of bacteria from at least one bacterial taxa selected from the group consisting of *Megasphaera cerevisiae, Alloscardovia omnicolens, Ureaplasma urealyticum, Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8, and a bacterial taxon specified by the nearest species classification based on BLAST nucleotide alignment in Tables 4E, 4G and 9; and (b) determining that the subject has an increased risk for an adverse pregnancy or neonatal outcome if the level of bacteria from the at least one bacterial genus is greater than that of a standard control level. In some embodiments, the method includes detecting the level of *Sneathia sanguinegens, Parvimonas micra, Ureaplasma urealyticum* or *Ureaplasma parvum, Atopobium vaginae, Peptoniphilus lacrimalis, Megasphaera cerevisiae, Parvibacter caecicola* in a biological sample taken from the subject, and determining that the subject has an increased risk of an adverse pregnancy outcome, if the total level of the bacteria is increased compared to a standard control level.

In some embodiments, adverse pregnancy or neonatal outcome includes preterm birth at <34 weeks, preterm birth at <37 weeks, delivery within about 1-196 days after the biological sample is taken, delivery within about 1-196 days after a clinical intervention is performed, an Apgar score at 1 minute of <7, an Apgar score at 5 minutes of <7, chorioamnionitis, respiratory distress syndrome, bronchopulmonary dysplasia, intraventricular hemorrhage, neonatal death within 7 days after birth or neonatal sepsis. In some cases, the method includes determining that the subject has a risk of having advanced cervical dilation or premature cervical shortening if the level of bacteria belonging the at least one bacterial taxon is greater than a standard control level In other embodiments, the method includes detecting the level of *Parvimonas micra, Ureaplasma urealyticum* or *Ureaplasma parvum, Atopobium vaginae, Peptoniphilus lacrimalis, Megasphaera cerevisiae, Parvibacter caecicola* in a biological sample taken from the subject, and determining that the subject has an increased risk of an adverse pregnancy outcome, such as delivery within 7 days after cervical intervention (i.e., cerclage/pessary intervention), if the total level of the bacteria is increased compared to a standard control level. In some cases, the method also includes determining that the subject is at risk of having an infection in the amniotic cavity, uterine cavity, cervix or vagina.

One class of *Megasphaera cerevisiae* can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_113307.1. In some embodiments, bacteria of the taxon *Megasphaera cerevisiae* are detected as having 16S rRNA nucleotide sequence with at least 93% or 94% sequence identity to the sequence of GenBank Accession No. NR_113307.1. In some embodiments, bacteria of the taxon *Megasphaera cerevisiae* are detected as having 16S rRNA nucleotide sequence shown in SEQ ID NO: 5.

*Alloscardovia omnicolens* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_042583.1. In some embodiments, bacteria of the taxon *Alloscardovia omnicolens* are detected as having 16S rRNA genomic sequence with 100% sequence identity to the nucleotide sequence of GenBank Accession No. NR_042583.1.

*Ureaplasma urealyticum* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA genomic sequence of GenBank Accession No. NR_102836.1. In some embodiments, bacteria of the taxon *Ureaplasma urealyticum* are detected as having 16S rRNA nucleotide sequence with 100% sequence identity to the nucleotide sequence of GenBank Accession No. NR_102836.1. *Ureaplasma parvum* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA genomic sequence of GenBank Accession No. NR_074176.1. In some embodiments, bacteria of the taxon *Ureaplasma parvum* are detected as having 16S rRNA nucleotide sequence with 100% sequence identity to the nucleotide sequence of GenBank Accession No. NR_074176.1. In some embodiments, bacteria of the taxon *Ureaplasma parvum* are detected as having 16S rRNA nucleotide sequence shown in SEQ ID NO: 7.

*Atopobium vaginae* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_117757.1. In some embodiments, bacteria of the taxon *Atopobium vaginae* are detected as having a 16S rRNA nucleotide sequence with 97% sequence identity to the nucleotide sequence of GenBank Accession No. NR_117757.1. In some embodiments, bacteria of the taxon *Atopobium vaginae* are detected as having a 16S rRNA nucleotide sequence shown in SEQ ID NO: 8.

*Parvibacter caecicola* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_117374.1. In some embodiments, bacteria of the taxon *Parvibacter caecicola* are detected as having a 16S rRNA nucleotide sequence with at least 92% sequence identity to the nucleotide sequence of GenBank Accession No. NR_117374.1. In some embodiments, bacteria of the taxon *Parvibacter caecicola* are detected as having a 16S rRNA nucleotide sequence shown in SEQ ID NO: 9.

*Lactobacillus casei* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_075032.1. In some embodiments, bacteria of the taxon *Lactobacillus casei* are detected as having a 16S rRNA nucleotide sequence with 100% sequence identity to the nucleotide sequence of GenBank Accession No. NR_075032.1.

*Veillonella montpellierensis* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_028839.1. In some embodiments, bacteria of the taxon *Veillonella montpellierensis* are detected as having a 16S rRNA nucleotide sequence with 100% sequence identity to the nucleotide sequence of GenBank Accession No. NR_028839.1.

*Anaerococcus senegalensis* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_118220.1. In some embodiments, bacteria of the taxon *Anaerococcus senegalensis* are detected as having a 16S rRNA nucleotide sequence with 100% sequence identity to the nucleotide sequence of GenBank Accession No. NR_118220.1.

*Bulleidia extructa* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_028773.1. In some embodiments, bacteria of the taxon *Bulleidia extructa* are detected as having 16S rRNA nucleotide sequence with 97% sequence identity to the nucleotide sequence of GenBank Accession No. NR_028773.1.

*Mycoplasma hominis* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_113679.1. In some embodiments, bacteria of the taxon *Mycoplasma hominis* are detected as having a 16S rRNA genomic sequence with 100% sequence identity to the nucleotide sequence of GenBank Accession No. NR_113679.1.

*Propionimicrobium lymphophilum* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_114337.1. In some embodiments, bacteria of the taxon *Propionimicrobium lymphophilum* are detected as having a 16S rRNA nucleotide sequence with 100% sequence identity to the nucleotide sequence of GenBank Accession No. NR_114337.1.

One class of uncultured bacteria relevant to the present disclosure can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. JQ781443.1. In some embodiments, bacteria of this taxon have a 16S rRNA nucleotide sequence with 92% sequence identity to the nucleotide sequence of GenBank Accession No. JQ781443.1.

*Corynebacterium pyruviciproducens* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_116569.1. In some embodiments, bacteria of the taxon *Corynebacterium pyruviciproducens* are detected as having a 16S rRNA nucleotide sequence with 100% sequence identity to the nucleotide sequence of GenBank Accession No. NR_116569.1.

Another class of *Megasphaera cerevisiae* can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_113307.1. In some embodiments, bacteria of the taxon *Megasphaera cerevisiae* are detected as having 16S rRNA nucleotide sequence with at least 93% or 94% sequence identity to the sequence of GenBank Accession No. NR_113307.1. In some embodiments, bacteria of the taxon *Megasphaera cerevisiae* are detected as having 16S rRNA nucleotide sequence shown in SEQ ID NO: 29.

*Acidipila rosea* bacteria can be identified as having a 16S rRNA nucleotide sequence with at least 90%, e.g., 90%, 91%, 92%, 93%, 94%, 95%, 96%, 97%, 98%, 99% or 100% sequence identity to the 16S rRNA nucleotide sequence of GenBank Accession No. NR_113179.1. In some embodiments, bacteria of the taxon *Acidipila rosea* are detected as having a 16S rRNA nucleotide sequence with 97% sequence identity to the nucleotide sequence of GenBank Accession No. NR_113179.1.

*Murdochiella asaccharolytica* bacteria can be identified as having a 16S rRNA nucleotide sequence with at least 90%, e.g., 90%, 91%, 92%, 93%, 94%, 95%, 96%, 97%, 98%, 99% or 100% sequence identity to the 16S rRNA nucleotide sequence of GenBank Accession No. NR_116331.1. In some embodiments, bacteria of the taxon *Murdochiella asaccharolytica* are detected as having a 16S rRNA nucleotide sequence with 99% sequence identity to the nucleotide sequence of GenBank Accession No. NR_116331.1.

Another class of uncultured bacteria relevant to the present disclosure can be identified as having a 16S rRNA nucleotide sequence with at least 90%, e.g., 90%, 91%, 92%, 93%, 94%, 95%, 96%, 97%, 98%, 99% or 100% sequence identity to the 16S rRNA nucleotide sequence of GenBank Accession No. JF295520.1. In some embodiments, bacteria of this taxon are detected as having a 16S rRNA nucleotide sequence with 90% sequence identity to the nucleotide sequence of GenBank Accession No. JF295520.1.

*Howardella ureilytica* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_044022.2. In some embodiments, bacteria of the taxon *Howardella ureilytica* are detected as having a 16S rRNA nucleotide sequence with 93% sequence identity to the nucleotide sequence of GenBank Accession No. NR_044022.2.

*Actinobaculum schaalii* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_116869.1. In some embodiments, bacteria of the taxon *Actinobaculum schaalii* are detected as having a 16S rRNA nucleotide sequence with 100% sequence identity to the nucleotide sequence of GenBank Accession No. NR_116869.1.

*Peptoniphilus duerdenii* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_116346.1. In some embodiments, bacteria of the taxon *Peptoniphilus duerdenii* are detected as having a 16S rRNA nucleotide sequence with 100% sequence identity to the nucleotide sequence of GenBank Accession No. NR_116346.1.

*Fastidiosipila sanguinis* bacteria can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_042186.1. In some embodiments, bacteria of the taxon *Fastidiosipila sanguinis* are detected as having a 16S rRNA nucleotide sequence with 100% sequence identity to the nucleotide sequence of GenBank Accession No. NR_042186.1.

*Sneathia sanguinegens* can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. AJ344093.1. In some embodiments, bacteria of the taxon *Sneathia sanguinegens* are detected as having 16S rRNA nucleotide sequence with at least 93% or 94% sequence identity to the sequence of GenBank Accession No. AJ344093.1.

*Parvimonas micra* can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession No. NR_114338.1. In some embodiments, bacteria of the taxon *Parvimonas micra* are detected as having 16S rRNA nucleotide sequence with at least 93%, e.g., 93%, 94%, 95%, 96%, 975 or more, sequence identity to the sequence of GenBank Accession No. NR_114338.1. In some embodiments, bacteria of the taxon *Parvimonas micra* are detected as having 16S rRNA nucleotide sequence shown in SEQ ID NO: 43.

*Peptoniphilus lacrimalis* can be identified as having a 16S rRNA nucleotide sequence with at least 90%, e.g., at least 90%, 91%, 92%, 93%, 94%, 95%, 96%, 97%, 98%, 99% or 100% sequence identity to the 16S rRNA nucleotide sequence of GenBank Accession Nos. AB971812.1 and NR_041938.1. In some embodiments, bacteria of the taxon *Peptoniphilus lacrimalis* are detected as having 16S rRNA nucleotide sequence with 100% sequence identity to the sequence of GenBank Accession Nos. AB971812.1 and NR_041938.1. In some embodiments, bacteria of the taxon *Peptoniphilus lacrimalis* are detected as having 16S rRNA nucleotide sequence shown in SEQ ID NO: 44. In some embodiments, the method includes detecting at least 2, 3, 4, 5, 6, 7, 8, 9, 10, 11, 12, 13, 14, 15, 16, 17, 18, 19 or 20 different bacterial taxa.

In some embodiments, the subject is a pregnant woman at about 13 weeks to about 37 weeks of gestation. In other embodiments, the pregnant woman is between about 13 to about 25 gestational weeks. In some cases, the pregnant woman has a prematurely opened cervix. The woman may be at risk of having an infection in the amniotic cavity, uterine cavity, cervix or vagina. In other embodiments, the subject is a non-pregnant woman. In some embodiments, the non-pregnant woman is planning for her future pregnancy. In some cases, the subject has a history of preterm birth, stillbirth or miscarriage. In some cases, the subject is planning to receive clinical intervention, such as cerlclage intervention or progesterone supplementation before or after pregnancy.

In some embodiments, the method also includes extracting nucleic acids from the biological sample taken from the subject prior to performing step (a). In some embodiments, the sample is a cervical swab (including swab sample of the external os), a vaginal swab (including swab sample of the fornix), a urine sample, an amniotic fluid sample, a maternal blood sample (maternal whole blood sample), a maternal serum sample, a maternal plasma sample, or a cervical mucus sample. In some embodiments, the sample is a placental swab, an umbilical swab, or any sample taken directly or indirectly from the reproductive system. This includes any sampling from the surface of the female reproductive tract via scraping, cutting, flushing, douching, applying a stream of gas, a liquid, a vacuum, a suction force, a form of energy (e.g., electrostatic field, LASER) or a gradient of chemicals (e.g., chemoattractants to induce chemotaxis). In some embodiment, the sample is taken directly or indirectly from the gastrointestinal system of the pregnant subject, including a buccal swab, a throat swab, an anal swab, a rectal swab or stool sample.

In some embodiments, the step of detecting includes a polynucleotide amplification assay. In some instances, the amplification assay is a polymerase chain reaction (PCR) assay. Optionally, the PCR assay can be a quantitative PCR assay. In some cases, the step of detecting includes sequence-specific probe/primer hybridization, which can occur in the absence of polynucleotide amplification. In other embodiments, the step of detecting includes polynucleotide sequence determination, such as but not limited to, massive parallel sequencing.

For instance, if the level of bacteria belonging a bacterial taxa including *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA genomic sequence in Tables 4A, 4C and 8, a bacterial taxon specified by the nearest species classification based on BLAST nucleotide alignment in Tables 4E, 4G and 9, or any combination thereof is elevated compared to a standard control, the pregnant subject is at risk of having an adverse pregnancy or neonatal outcome. When an increase in the level of bacteria of one or more of the selected bacterial taxa compared to the standard control is determined, it indicates that the woman has an increased risk of premature birth or delivering a child with a neonatal complication. For example, when the level of bacteria from one or more of the taxa, such as *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA genomic sequence in Tables 4A, 4C and 8, and a bacterial taxon specified by the nearest species classification based on BLAST nucleotide alignment in Tables 4E, 4G and 9, in a cervical or vaginal swab sample from a pregnant woman is detected to be higher compared to the standard control, the woman has an increased likelihood of having an adverse pregnancy and/or neonatal outcome. Possible adverse pregnancy or neonatal outcomes include, but are not limited to, preterm birth at <34 weeks, preterm birth at <37 weeks, an Apgar score at 1 minute of <7, an Apgar score at 5 minutes of <7, chorioamnionitis, respiratory distress syndrome, bronchopulmonary dysplasia, intraventricular hemorrhage, neonatal death within 7 days after birth, and/or neonatal sepsis. Furthermore, if the subject is a pregnant woman, the possible adverse pregnancy or neonatal outcomes further include delivery within a period of about 1-196 days (e.g., 1 day, 7 days, 14 days, 21 days, 28 days, 56 days, 84 days, 112 days, 140 days, 168 days, or 196 days) after the biological sample is taken, delivery within a period of about 1-196 days (e.g., 1 day, 7 days, 14 days, 21 days, 28 days, 56 days, 84 days, 112 days, 140 days, 168 days, or 196 days) after the clinical intervention is performed.

The method provided herein can be used to determine that the pregnant woman has a risk of having advanced cervical dilation or advanced cervical shortening. For instance, if the level of bacteria from at least one bacterial taxon, such as *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria as having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8, and a bacterial taxon specified by the nearest species classification based on BLAST nucleotide alignment in Tables 4E, 4G and 9 is greater than that of a standard control level, the woman has an increased likelihood of having advanced cervical dilation or premature cervical shortening. Such a subject is predicted to exhibit cervical dilation of, for example, ≥2 cm, without active labor between 13 weeks to up to 37 weeks of gestation, or cervical shortening prior to full-term labor and delivery.

In some instances, the method can further include detecting in the biological sample the level of bacteria from at least one bacterial taxon selected from the group consisting of *Jonquetella anthropi, Aerococcus urinae*, a bacterial taxon specified by a 16S rRNA nucleotide sequence in Tables 4B and 4D, and a bacterial taxon specified by the nearest species classification based on BLAST nucleotide alignment in Tables 4F and 4H; and determining that the subject has an increased risk for an adverse pregnancy outcome if the level of bacteria from the at least one bacterial taxon is lower than that of a standard control level.

If the pregnant woman is predicted of having an adverse pregnancy or neonatal outcome, the method can include repeating steps (a) and (b) at a later time using a sample type of the biological sample from the subject, wherein an increase in the level of bacteria from the at least one bacterial taxon at the later time as compared to the level determined in the original step (a) indicates an increased risk of having an adverse pregnancy or neonatal outcome. Furthermore, once a pregnant woman is indicated as having increased risk of experiencing an adverse pregnancy or neonatal outcome, a physician may provide treatment for the woman to minimize the risk of such adverse outcome. For example, the woman may be closely monitored throughout pregnancy or be timely transferred to a tertiary unit with neonatal intensive care.

In another aspect, the present invention provides a kit for determining the risk of having an adverse pregnancy or neonatal outcome in a subject. The kit can include (a) a standard control that provides a biological sample taken from a pregnant female and containing bacteria belonging to at least one bacterial taxon selected from the group consisting of *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8; and a bacterial taxon specified by the nearest species classification based on BLAST nucleotide alignment in Tables 4E, 4G and S and (b) one or more agents that specifically and quantitatively identify at least one bacterial taxon selected from the group consisting of *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, and a bacterial taxon specified by a 16S rRNA nucleotide sequence in Tables 4A, 4C and 8, and a bacterial taxon specified by the nearest species classification based on BLAST nucleotide alignment in Tables 4E, 4G and 9. In some embodiments, the one or more agent may include one or more pairs of oligonucleotide primers that specifically hybridize to and amplify a polynucleotide of the at least one bacterial genus in an amplification assay. In some embodiments, the one or more agents may further include a polynucleotide probe that specifically hybridizes to a polynucleotide sequence of the at least one bacterial taxon. In some instances, the kit includes an instruction manual.

In another aspect, the present invention provides a method for determining whether a pregnant subject has an increased risk of having advanced cervical dilation or premature cervical shortening. The method includes the steps of (a) extracting nucleic acids from a biological sample taken from the subject; (b) detecting in the nucleic acids the level of at least one bacterial taxon selected from the group consisting of *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8, and a bacterial taxon specified by the nearest species classification based on BLAST nucleotide alignment in Tables 4E, 4G and 9; and (c) determining that the subject has an increased risk of having advanced cervical dilation or premature cervical shortening if the level of the at least one bacterial taxon is greater than that of a standard control level. For example, a pregnant woman is predicted to be at risk of having a prematurely dilated cervix and/or a prematurely shortened cervix, if it is determined that she has an increased level of bacteria from one or more of the selected bacterial taxa in her cervix or vagina. If she has more bacteria from the group, such as *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having a 16S rRNA nucleotide sequence with at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having a 16S rRNA nucleotide sequence with at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8, a bacterial taxon specified by the nearest species classification based on BLAST nucleotide alignment in Tables 4E, 4G and 9, or any combination thereof in her cervix or vagina at, for example, about 13 to about 25 gestational weeks, she is likely to have a dilated cervix or shortened cervix prior to about 34 to about 37 gestational weeks. At least 2, 3, 4, 5, 6, 7, 8, 9, 10, 11, 12, 13, 14, 15, 16, 17, 18, 19 or 20 different bacterial taxa can be detected in the sample.

In some embodiments, the biological sample is a cervical swab, a vaginal swab, a urine sample, an amniotic fluid sample, a maternal blood sample, a maternal serum sample, a maternal plasma sample, a cervical mucus sample, a placental swab, an umbilical cord swab or any sample taken directly or indirectly from the reproductive system or the gastrointestinal system. The detecting step can be a polynucleotide amplification assay, an assay involving polynucleotide sequence determination, or an assay involving sequence-specific probe/primer hybridization. In some instances, the amplification assay is a polymerase chain reaction (PCR) assay. Optionally, the PCR assay is a quantitative PCR assay or a reverse-transcriptase PCR assay.

BRIEF DESCRIPTION OF DRAWINGS

FIGS. 1A-1E show the association between clinical outcomes, such as spontaneous preterm birth (sPTB) after intervention and term birth (TB) after intervention, and bacterial taxa. FIG. 1A shows the clinical outcomes of 25 cervical insufficiency (CI) patients after intervention. Each column represents a patient (P1-P25) in ascending order of gestational age (GA) at delivery. Black rectangles: P1-P10 resulting in "spontaneous preterm birth (sPTB)<34 weeks after intervention". White rectangles: P11-P25 resulting in "term birth (TB)≥37 weeks after intervention". Latency, the interval between treatment and delivery. RDS, respiratory distress syndrome. BPD, bronchopulmonary dysplasia. IVH, intraventricular haemorrhage. ROP, retinopathy of prematurity. Neonatal death, death within 28 days after delivery. Y, Yes; n, no; –, not determined. FIGS. 1B and 1C show the 10 most abundant bacterial taxa in the "sPTB after intervention" and "TB after intervention" CI cervices, respectively. Shown values are the log 10 of the abundance values (normalized sequencing read counts, the Cumulative Sum Scaling (CSS) method) of each bacterial taxon (row) in the cervical swab sample of each patient (column). Normalized read counts are transformed into log (abundance) as noted in FIG. 1E. Each row represents an operational taxonomic unit (Otu) formed by clustering sequences of ≥97% identity. Each Otu is taxonomically classified at the genus level using the Ribosomal Database Project (RDP) Naïve Bayesian rRNA Classifier (Version 2.9, September 2014, RDP 16S rRNA training set 10). *Lactobacillus* are further matched against the 16S rRNA database (GenBank) using BLAST (highest score) and MOLE-BLAST (best multiple-alignment of BLAST matches) for deriving the species information. FIG. 1D shows the differentially abundant bacterial taxa between the "sPTB after intervention" (n=10) and the "TB after intervention" (n=15) groups (Mann-Whitney rank sum test). Seven taxa remain as differentially abundant after adjustment for multiple testing by the False Discovery Rate (FDR) method ($p<0.05$ and q-value $<0.05$, i.e. FDR<5%, in asterisk). The latter 6 taxa with $p<0.01$ are further selected for calculating a summary score, namely the log (base 10) total abundance of 6 selected taxa (LA6) value, for each cervical swab sample. Total abundance is the arithmetic sum of abundances of the selected taxa in common (linear) scale.

FIG. 2A provides LA6 values (the total abundance of the 6 selected bacterial taxa in logarithmic (base 10) scale) in two groups of cervical insufficiency (CI) patients both receiving clinical intervention but resulting in different outcomes. Cervical swab samples for measuring the LA6 were collected from CI patients before cerclage/pessary intervention. After the treatment, 10 patients resulted in spontaneous preterm birth <34 weeks (the "sPTB after intervention" group, circles), and 15 patients resulted in term birth ≥37 weeks (the "TB after treatment" group, triangles). The 6 taxa were selected based on their significantly different abundances ($p<0.01$) between these two groups in the massively parallel sequencing data (FIG. 1D). The long and short horizontal lines of the error bar are drawn to the median and interquartile range, respectively. FIG. 2B shows the proportion of undelivered pregnancies at different gestational period in CI patients with LA6>1.15 (LA6-positive) vs. those with LA6<1.15 (LA6-negative). LA6-positive patients delivered earlier after clinical intervention than the LA6-positive patients (median gestational age at delivery of 23.7 weeks vs. 38.4 weeks; 95% confidence interval, 20.6 weeks-25.4 weeks vs. 38.0 weeks-38.7 weeks; Chi-squared, 32.352; df, 1; Logrank test, $p<0.0001$; hazard ratio, 6.24; 95% confidence interval, 1.50 to 25.9). The 95% confidence intervals of the percentages of undelivered pregnancies for LA6-positive and LA6-negative patients are shown as hairlines around the bold solid line and the bold dotted line, respectively. FIG. 2C shows the proportion of undelivered pregnancies at different days after treatment in LA6-positive vs. LA6-negative CI patients. LA6-positive patients delivered for a shorter period after intervention than their LA6-negative counterparts (median number days between intervention and delivery, 10 days vs. 126 days; 95% confidence interval, 8 days-32 days vs. 112 days-134 days; Chi-squared, 32.520; df, 1; Logrank test, $p<0.00001$; hazard ratio, 6.34; 95% confidence interval, 1.51 to 26.6).

DEFINITIONS

Figure 2A:
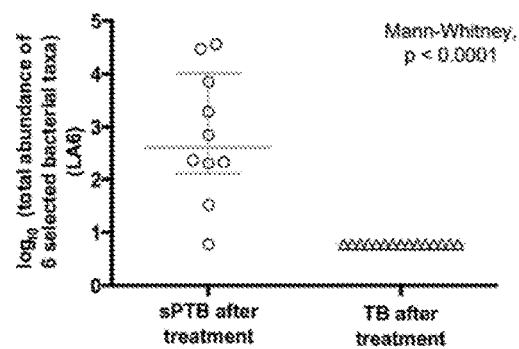
FIGS. 2A-2C provides statistical analysis and LA6 values for the two groups, e.g., patients with spontaneous preterm birth (sPTB) after intervention and patients with term birth (TB) after intervention.

In this disclosure the term "or" is generally employed in its sense including "and/or" unless the content clearly dictates otherwise.

The term "adverse pregnancy or neonatal outcome" refers to a condition that reduces the chance of delivering/birthing a healthy baby. Non-limiting examples of an adverse pregnancy outcome includes multiple first trimester miscarriages, a second trimester pregnancy loss, preterm birth (e.g., spontaneous or indicated), preterm pre-clampsia, preterm clampsia, fetal growth restriction, abruption placenta, fetal death/stillbirth, birth defects, Apgar score at 1 minute of <7, Apgar score at 5 minute of <7, clinical chorioamnioitis, pathological chorioamnioitis, neonatal respiratory distress syndrome, neonatal bronchopulmonary dysplasia, neonatal sepsis, neonatal intraventricular hemorrhage, etc.

The term "cervical insufficiency" refers to a condition of the cervix, such as weakening or advanced dilation of the cervix that can lead to second-trimester pregnancy loss or birth. Cervical weakness, premature cervical shortening, premature or advanced cervical dilation, cervical trauma, a structural abnormality of the cervix, or any combination thereof can contribute to cervical insufficiency. Clinical interventions to manage cervical insufficiency include, but are not limited to, progesterone supplementation, cervical cerclage, and cervical pessary.

The term "bacterial taxon" refers to the taxonomy, i.e., the rank-based classification of bacteria. The hierarchical biological classification includes life, domain, kingdom, phylum, class, order, family, genus and species.

The term "biological sample" or "sample" includes sections of tissues such as biopsy and autopsy samples, and frozen sections taken for histologic purposes, or processed forms of any of such samples. Biological samples include a cervical swab, a vaginal swab, a uterine swab, blood and blood fractions or products (e.g., serum, plasma, platelets, red blood cells, and the like), sputum or saliva, lymph and tongue tissue, cultured cells, e.g., primary cultures, explants, and transformed cells, stool, urine, a biopsy tissue etc. A biological sample is typically obtained from a eukaryotic organism, which may be a mammal, may be a primate and may be a human subject.

The term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., cervix, vagina, tongue, colon, prostate, kidney, bladder, lymph node, liver, bone marrow, blood cell, stomach tissue, etc.) among other factors. Representative biopsy techniques include, but are not limited to, a swab biopsy, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule can be introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamide) containing restriction-digested genomic DNA, is not an "isolated" nucleic acid.

The term "nucleic acid," "nucleotide or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The terms "identical" or percent "identity," in the context of describing two or more polynucleotide or amino acid sequences, refer to two or more sequences or subsequences that are the same or have a specified percentage of amino acid residues or nucleotides that are the same (for example, a variant of a bacterial protein or interest used in the method of this invention (e.g., for predicting adverse pregnancy outcomes) has at least 80% sequence identity, preferably 85%, 90%, 91%, 92%, 93, 94%, 95%, 96%, 97%, 98%, 99%, or 100% identity, to a reference sequence, e.g., a corresponding wild-type bacterial protein of interest), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

The phrase "specifically binds" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of a bacterial mRNA or protein found in normal cervical or vaginal tissue from a pregnant control subject). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for a specific bacterial gene or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of bacteria belonging to a specific bacterial genus, a bacterial polynucleotide or a bacterial polypeptide that is present in an established normal tissue sample, e.g., a normal cervical tissue sample. The standard control value is suitable for the use of a method of the present invention, to serve as a basis for comparing the amount of a specific bacterial genus, mRNA or protein that is present in a test sample. An established sample serving as a standard control provides an average amount of the bacterial genus, mRNA or protein that is typical for a cervical tissue sample of an average, healthy pregnant human with, for example, a closed cervix or normal-length cervix, as conventionally defined. A standard control value may vary depending on the nature of the sample, the manner of sample collection, as well as other factors such as the gender, age, ethnicity of the subjects (and in the case of pregnant women, gestational age) based on whom such a control value is established.

The term "average," as used in the context of describing a human who is pregnant and not at risk of having an adverse pregnancy or neonatal outcome, as conventionally defined, refers to certain characteristics, especially the amount of bacteria of one or more specific bacterial taxa, found in the person's cervix that are representative of a randomly selected group of pregnant humans who are free of any risk of having an adverse pregnancy or neonatal outcome. This selected group should comprise a sufficient number of humans such that the average amount of bacteria of the specific taxa in the cervix among these individuals reflects, with reasonable accuracy, the corresponding amount of bacteria of the taxa in the general population of healthy, normal, pregnant humans. In addition, the selected group of pregnant humans generally have a similar gestational-age to that of a subject whose cervical tissue sample is tested for indication of a risk of having an adverse pregnancy or neonatal outcome. Moreover, other factors such as age, the status of receiving the same or similar kind of intervention (e.g., pessary/cerclage intervention), ethnicity, medical history are also considered and preferably closely matching between the profiles of the test subject and the selected group of individuals establishing the "average" value.

The term "amount" or "level" as used in this application refers to the quantity of a bacterial taxon of interest, a bacterial polynucleotide of interest or a bacterial polypeptide of interest present in a sample. Such quantity may be expressed in the absolute terms, i.e., the total quantity of the bacterial taxon, polynucleotide or polypeptide in the sample, or in the relative terms, i.e., the concentration of the bacterial taxon, polynucleotide or polypeptide in the sample.

The term "subject" includes individuals who seek medical attention due to a potential risk of having an adverse pregnancy outcome or neonatal outcome, e.g., any pregnant individual. Subjects also include individuals who have had an adverse pregnancy or neonatal outcome during a prior pregnancy.

DETAILED DESCRIPTION OF THE INVENTION

I. Introduction

The invention is based, in part, on the discovery of differentially abundant bacterial taxa in the cervical swab samples of women with advanced cervical dilation/cervical shortening, compared with those in appropriately-controlled samples from appropriately-matched women without the corresponding condition. The increased level of bacteria from particular bacterial taxa (e.g., *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8, and a bacterial taxon specified by the nearest species classification based on BLAST nucleotide alignment in Tables 4E, 4G and 9) is also predictive of a risk of having an adverse pregnancy or neonatal outcome, such as preterm birth (e.g., spontaneous preterm birth)<34 weeks, preterm birth (e.g., spontaneous preterm birth)<37 weeks, delivery within a period after the biological sample is taken (e.g., 1 day, 7 days, 14 days, 21 days, 28 days, 56 days, 84 days, 112 days, 140 days, 168 days, 196 days), delivery within a period after the clinical intervention is performed (e.g., 1 day, 7 days, 14 days, 21 days, 28 days, 56 days, 84 days, 112 days, 140 days, 168 days, 196 days), an Apgar score at 1 minute <7, an Apgar score at 5 minutes <7, chorioamnionitis (e.g., clinical or pathological), respiratory distress syndrome, bronchopulmonary dysplasia, intraventricular hemorrhage, neonatal death within 7 days after birth and neonatal sepsis.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, Gene *Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

III. Acquisition of Tissue Samples and Analysis of Bacterial Taxa

The present invention relates to measuring the amount of bacteria of a specific bacteria taxon found in a pregnant woman's cervix or vagina, especially in a cervical swab or vaginal swab sample, as a means to assess the risk of having an adverse pregnancy outcome or neonatal outcome, such as preterm labor and preterm delivery. Thus, the first steps of practicing this invention are to obtain a cervical or vaginal tissue sample from a test subject, such that the nucleic acids, e.g., RNA or DNA, contained in the sample may be analyzed. In some embodiments, the amount of bacteria of a specific bacteria taxon found in a pregnant woman's cervix or vagina can be represented by the amount of the specific bacteria in a biological sample that is not from the cervix or the vagina.

A. Acquisition and Preparation of Biological Samples

A biological sample, such as cervical or vaginal tissue, cervical mucus, amniotic fluid or maternal blood is obtained from a person to be tested or monitored using a method of the present invention. Collection of cervical or vaginal epithelial cells, cervical mucus, amniotic fluid or maternal blood (e.g., material whole blood, maternal serum and/or maternal plasma) from an individual is performed in accordance with the standard protocol hospitals or clinics generally follow, such as during a cervical screening. An appropriate amount of cervical or vaginal epithelium, scraped cells, mucus, and/or biological fluid is collected and may be stored according to standard procedures prior to further preparation.

The analysis of the bacteria found in a pregnant patient's sample according to the present invention may be performed using, e.g., cells, tissue, mucosa, or fluids found in the sample. The methods for preparing cell, tissue or fluid samples for nucleic acid extraction are well known among those of skill in the art. For example, a subject's cervical or vaginal mucosa sample can be treated to such that bacterial DNA or RNA in the sample can be analyzed.

B. Extraction and Quantitation of DNA

There are numerous methods for extracting bacterial DNA from a biological sample. Methods for extracting DNA from a biological sample are well known and routinely practiced in the art of molecular biology, see, e.g., Sambrook and Russell, supra. RNA contamination should be eliminated to avoid interference with DNA analysis. Pretreatment of the biological sample with lysis buffer and enzymes, including mutanolysin and proteinase K, can also be used before the extraction. Methods for detecting target DNA include either PCR analysis, quantitative analysis with fluorescence labelling or Southern blot analysis. The target DNA can be the gene encoding the 16S ribosomal RNA (the 16S rRNA gene), or other genes or genomic sequences of interest possessed by a specific bacterial taxon.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of specific bacterial mRNA markers. For a detailed description of branched-DNA signal amplification for direct quantitation of nucleic acid sequences in clinical samples, see, for example, Nolte, *Adv. Clin. Chem.* 33:201-235, 1998.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting a polynucleotide sequence for practicing the methods of the present invention include but are not limited to mass spectrometry, primer extension, polynucleotide hybridization, real-time PCR, melting curve analysis, high resolution melting analysis, heteroduplex analysis, massively parallel sequencing (e.g., next-gen sequencing), and electrophoresis.

C. Extraction and Quantitation of RNA

One skilled in the art recognizes that there are numerous methods for extracting bacterial RNA from a biological sample. The general methods of RNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

D. PCR-Based Quantitative Determination of RNA Level

Once RNA is extracted from a sample, the amount of any RNA transcripts of interest that is expressed by bacteria of a specific bacterial taxon may be quantified. For example, the amount of 16S ribosomal RNA (rRNA) for a particular bacterial taxon, such as, but not limited to, *Megasphaera cerevisiae, Alloscardovia omnicolens, Ureaplasma urealyticum* or *Ureaplasma parvum, Atopobium vaginae, Parvibacter caecicola, Lactobacillus casei, Veillonella montpellierensis, Anaerococcus senegalensis, Bulleidia extructa, Mycoplasma hominis, Propionimicrobium lymphophilum*, uncultured bacteria having at least 92% sequence identity to the nucleotide sequence of GenBank Accession No. JQ781443.1, *Corynebacterium pyruviciproducens, Megasphaera cerevisiae, Acidipila rosea, Murdochiella asaccharolytica*, uncultured bacteria having at least 90% sequence identity to the nucleotide sequence of GenBank Accession No. JF295520.1, *Howardella ureilytica, Actinobaculum schaalii, Peptoniphilus duerdenii, Fastidiosipila sanguinis, Sneathia sanguinegens, Parvimonas micra, Peptoniphilus lacrimalis*, a bacterial taxon specified by a 16S rRNA nucleotide sequence in Tables 4A, 4C and 8, and a bacterial taxon specified by the nearest species classification based on BLAST nucleotide alignment in Tables 4E, 4G and 9 may be detected and measured. The preferred method for determining the RNA transcript level is an amplification-based method, e.g., by polymerase chain reaction (PCR), especially reverse transcription-polymerase chain reaction (RT-PCR).

Prior to the amplification step, a DNA copy (cDNA) of a bacterial RNA transcript of interest must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target RNA is typically used in practicing the present invention. One of skill in the art will recognize, however, that amplification of these bacterial RNA species in the sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of specific bacterial RNA markers. For a review of branched-DNA signal amplification for direct quantitation of nucleic acid sequences in clinical samples, see Nolte, *Adv. Clin. Chem.* 33:201-235, 1998.

E. Other Quantitative Methods for DNA and RNA

The bacterial DNA or RNA transcripts of interest can also be detected using other standard techniques, well-known to those of skill in the art. Although the detection step is typically preceded by an amplification step, amplification is not required in the methods of the invention. For instance, the DNA or RNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target DNA or RNA, the amount of which may then be compared to the control based on the intensity of the band. Alternatively, oligonucleotide probes specific to the DNA or RNA of interest can be used to detect the presence of such DNA or RNA species and indicate the amount of DNA or RNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques*, 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the RNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half-lives of the selected isotopes. Other labels include compounds (e.g., biotin and digoxigenin), which bind to anti-ligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

F. Amplification and Sequence Analysis

An amplification reaction may performed prior to the sequence analysis. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting a polynucleotide sequence for practicing the methods of the present invention include but are not limited to mass spectrometry, primer extension, polynucleotide hybridization, real-time PCR, melting curve analysis, high resolution melting analysis, heteroduplex analysis, massively parallel sequencing, and electrophoresis.

IV. Establishing a Standard Control

In order to establish a standard control for a particular sample type (e.g., cervical swab or vaginal swab) for practicing the method of this invention, a group of healthy pregnant women, pregnant women who are not at risk of having an adverse pregnancy outcome or neonatal outcome, or pregnant women who are later confirmed to deliver within the normal time frame of their pregnancy, as conventionally defined is first selected. For example, the group may include a group of pregnant women who have had a full-term labor and delivery. In some embodiments, the group of pregnant women may have had a full-term labor and delivery after clinical intervention, such as cerclage or pessary. These individuals are within the appropriate parameters, if applicable, for the purpose of screening for and/or monitoring risk of adverse pregnancy outcomes using the methods of the present invention. For instance, the individuals may be of a similar gestational age and comparable health status. Optionally, the individuals are of similar age, or similar ethnic background.

The normal delivery time of the selected individuals will be confirmed later on, and anyone among the selected individuals who turn out to give birth sooner or later than the normal delivery time frame will be excluded from the group to provide data as a "standard control."

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of bacteria of one or more bacterial taxa in the cervical tissue sample obtained from the group can be reasonably regarded as representative of the normal or average level among the general population of healthy pregnant women. Preferably, the selected group comprises at least 10 pregnant human subjects.

Once an average value for the bacteria of one or more taxa is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gestational age, or ethnic background.

V. Predicting Risk of Adverse Pregnancy or Neonatal Outcome Based on Cervical Microbe Score Using the methods described herein, it can be predicted whether a pregnant subject has a likelihood of having an adverse pregnancy outcome, e.g., spontaneous preterm birth or birth prior to 34 weeks in the current pregnancy. Likewise, it can be predicted whether a non-pregnant subject has a likelihood of having an adverse pregnancy outcome in the future pregnancy. In some embodiments, for each subject, the abundance levels of bacteria belonging to at least 1, e.g., 1, 2, 3, 4, 5, 6, 7, 8, 9, 10, 11, 12, 13, 14, 15, 16, 17, 18, 19, 20 or more bacterial taxa can be used to calculate a cervical microbe score. The subject's score can be compared to a cut-off value established by the scores of the standard control group, and used to determine if the pregnant subject is likely to have an adverse pregnancy outcome. In some embodiments, the bacteria belong to at least 3, e.g., 1, 2, 3, 4, 5, 6, 7, 8, 9, 10, 11, 12, 13, 14, 15, 16, 17, 18, 19, 20 or more bacteria taxa. In some cases, the bacteria include *Sneathia sanguinegens*, *Parvimonas micra*, *Ureaplasma urealyticum* (or *Ureaplasma parvum*), *Atopobium vaginae*, *Peptoniphilus lacrimalis*, *Megasphaera cerevisiae*, and *Paravibacter caecicola*. In other cases, the abundance levels of *Parvimonas micra*, *Ureaplasma urealyticum* (or *Ureaplasma parvum*), *Atopobium vaginae*, *Peptoniphilus lacrimalis*, *Megasphaera cerevisiae*, and *Paravibacter caecicola* is used to calculate the cervical microbe score for the subject. In some embodiments, each $\log_{10}$(abundance) value for the selected bacteria taxon can be transformed into the linear scale and then added together, after which the total value is log-transformed and expressed as a cervical microbe score in the $\log_{10}$ scale. In some instances, a cervical microbe score of greater than 1.15 can indicate that the pregnant subject is at risk of having a spontaneous preterm birth. In some cases, the pregnant subject is at risk of having a spontaneous preterm birth after intervention, such as cerclage or pessary. In some embodiments, a cervical score of greater than 1.15 can indicate that the pregnant subject has an increased likelihood of delivering at less than about 37.0 weeks, e.g., about 36.5 weeks, about 36.0 weeks, about 35.0 weeks, about 34.0 weeks, about 33.0 weeks, about 32.0 weeks, about 31.0 weeks, about 30.0 weeks, about 29.0 weeks, about 28.0 weeks, about 27.0 weeks, about 26.0 weeks, about 25.0 weeks, about 24.0 weeks, about 23.0 weeks, about 22.0 weeks, about 21.0 weeks, or less.

In some embodiments, for each biological sample, the abundance level of a bacterial taxon is determined by quantitative PCR assay or sequence-specific hybridization assay targeting polynucleotide sequences specific to the concerned taxon. In other embodiments, for each biological sample, the abundance level of a bacterial taxon is determined by massive parallel sequencing of the marker gene sequences which serve as proxy of the respective taxon. In some instances, the abundance level of a bacterial taxon in a sample is the normalized read counts of the 16S ribosomal RNA (rRNA) gene sequence representing the concerned taxon. In some cases, the normalized read counts are calculated from the raw read counts using established normalization methods to minimize the technical variation between samples, such as different sequencing depth per sample or different library size per sample. In some cases, the abundance level of a bacterial taxon is expressed in the $\log_{10}$ scale.

In some embodiments, the abundance of a selected group of bacterial taxa (e.g., taxa that are significantly more abundant in the dilated cervices than the closed cervices) are combined by addition or multiplication to give the cervical microbe score, as illustrated in the LA6 value in Example 2. In other embodiments, the score is calculated in 3 steps: (a) the abundance levels of one sub-selected group of bacterial taxa (e.g., taxa that are significantly more abundant in the dilated cervices than the closed cervices) are combined by addition or multiplication; (b) the abundance levels of another sub-selected group of taxa (e.g., taxa that are significantly more abundant in the closed cervices than the dilated cervices) are also combined by addition or multiplication; and (c) the cervical microbe score is calculated by subtracting or dividing between the sum or product of the first selected group of taxa and the sum or product of the second sub-selected group of taxa. In other embodiments, the cervical microbe score is calculated based on the number of kinds of selected bacterial taxa that are present in a sample, as illustrated in the DIBT1 test, DIBT2 test and DIBT3 test in Example 1. In the DIBT1, DIBT2 and DIBT3 tests, the cervical microbe score is the number of selected bacterial taxa, and a subject with score greater than or equal to 1 indicates increased risk of adverse pregnancy or neonatal outcome. In other embodiments, the cervical microbiome score is calculated based on the ranking of selected bacterial taxa among all taxa detected in a sample.

VI. Kits

The invention provides compositions and kits for practicing the methods described herein to assess the level of bacteria from one or more specific taxa in a pregnant subject, which can be used for various purposes such as determining the risk of having an adverse pregnancy or neonatal outcome.

Kits for carrying out assays for determining the RNA level of bacteria of a bacterial taxon of interest typically include at least one oligonucleotide useful for specific hybridization with at least one segment of a coding sequence of interest or its complementary sequence. Optionally, this oligonucleotide is labeled with a detectable moiety. In some cases, the kits may include at least two oligonucleotide primers that can be used in the amplification of at least one segment of a bacterial DNA or RNA transcript of interest by PCR, particularly by RT-PCR.

Kits for carrying out assays for determining the protein level of bacteria of a bacterial taxon of interest typically include at least one antibody useful for specific binding to the target protein amino acid sequence. Optionally, this antibody is labeled with a detectable moiety. The antibody can be either a monoclonal antibody or a polyclonal antibody. In some cases, the kits may include at least two different antibodies, one for specific binding to the target protein (i.e., the primary antibody) and the other for detection of the primary antibody (i.e., the secondary antibody), which is often attached to a detectable moiety.

Typically, the kits also include an appropriate standard control. The standard controls indicate the average value of a target protein or a target mRNA expressed by bacteria from a specific bacterial taxon in the cervical epithelium of healthy, pregnant subjects who are not at risk of having an adverse pregnancy or neonatal outcome. In some cases such standard control may be provided in the form of a set value. In addition, the kits of this invention may provide instruction manuals to guide users in analyzing test samples and assessing the risk of having an adverse pregnancy event, such as preterm delivery, in a test subject.

EXAMPLES

The following examples are provided by way of illustration only and not by way of limitation. Those of skill in the art will readily recognize a variety of non-critical parameters that could be changed or modified to yield essentially the same or similar results.

Example 1. Differentially Abundant Bacterial Taxa in the Cervix of Women with Pregnancy-Associated Complications Background To support the cervix in an attempt to prolong pregnancy of women with advanced cervical dilation or premature cervical shortening, the clinicians may place a cerclage (Owen, Hankins et al. 2009) or a cervical pessary. However, it was shown that women with infection, such as intra-amniotic infection, despite placement of cerclage, were associated with adverse pregnancy outcomes, including pregnancy loss, preterm birth, rupture of membrane (Romero, Gonzalez et al., 1992). Specifically, among 33 women with cervical dilation > or =2 cm, intact membrane, and without active labor between 14 and 24 weeks of gestation, 17 (51.5%) were found to have microbial invasion of the amniotic cavity. All patients with microbial invasion of the amniotic cavity had complications. Patients who underwent cervical cerclage in the presence of a positive amniotic fluid culture had rupture of membranes, clinical chorioamnionitis or pregnancy loss (Romero, Gonzalez et al., 1992). Hence, cerclage may not be beneficial to this subset of patients with advanced cervical dilation. Based primarily on consensus and expert opinion, it has been recommended that cerclage placement may be beneficial only if intraamniotic infection is ruled out (American College of Obstetricians and Gynecologists. 2014. Cerclage for the management of cervical insufficiency. Practice Bulletin No. 142. *Obstet Gynecol* 2014; 123:372-9). Similarly, it has also been suggested to rule out infection before pessary placement, because trapping the fetus inside a highly infectious or inflammatory environment may lead to adverse neonatal outcomes, including cerebral palsy or brain damage of the fetus.

Currently, the detection of bacteria in a sample relies on culture, microscopy and bacterial species-specific polymerase chain reaction (PCR) assays, which only offer low to moderate sensitivity and hence are not good at ruling out infection. For example, using amniotic fluid culture for aerobic and anaerobic bacteria as well as genital mycoplasmas and PCR targeting *Ureaplasma urealyticum* and *Ureaplasma parvum*, 44 patients (76%) of all 58 patients with advanced cervical dilation were tested negative of bacteria for both culture and PCR (Oh, Lee et al., 2010). However, eventually, among these women tested negative of bacteria, 63% ($^{15}/_{24}$) were tested positive for choriodeciduitis, 30% ($^{7}/_{23}$) positive for amnionitis, 25% ($^{6}/_{24}$) positive for funisitis, 62% ($^{24}/_{39}$) delivered a neonate with 1 min Apgar score <4, 41% ($^{18}/_{44}$) delivered a neonate who died within 1 day of birth (Oh, Lee et al., 2010). The prevalence of inflammation and poor neonatal outcome in these 44 patients with negative culture and PCR results suggested that many of these negative test results for bacteria might be falsely negative.

Furthermore, *Ureaplasmas* were also detected in pregnancies of normal uncomplicated outcomes (Gray, Robinson et al., 1992, Gerber, Vial et al., 2003, Perni, Vardhana et al., 2004). It is possible that *Ureaplasmas* are just part of the commensal bacteria, or normal flora, residing also in the reproductive tract of women resulting in a term pregnancy and normal neonate. This highlights the limitation of detecting for only a few bacterial species, selected by a candidate approach, in many of the previous studies.

In contrast, we have systematically profiled the presence and relative abundance of essentially all (>9,500 kinds/taxa of bacteria with known genomic sequences) in each of the cervical swab samples, obtained from women with advanced cervical dilation/shortening and without those conditions, using 16S ribosomal RNA (rRNA)-based massively parallel genomic sequencing. Our approach has overcome several limitation of those previous studies. First, our approach can universally detect essentially all bacterial taxa, but not only a selected list of candidates. Second, our approach is independent from culture, and thus fastidious bacteria may also be detected. Third, our approach does not require live bacteria, since it is based on PCR which can amplify the genomic DNA fragments from dead or live bacteria. Fourth, our approach investigates a non-invasive sample type, the cervical swab, which is readily obtainable from any pregnant women with or without complications. This facilitates appropriate matching with a normal control group and data comparison between the disease and control groups, unlike amniotic fluid which requires invasive procedures risking fetal loss and not recommended for normal pregnancy unless there is an indication. Fifth, our approach investigates the cervical swab, which is readily obtainable from any pregnant women at any gestational age. This facilitates not only matching with a control group but also a possibly early sampling and hence detection and treatment, unlike amniotic fluid or the placenta, which are usually obtained after 14 weeks or 37 weeks of gestation, respectively.

There are many publications utilizing 16S ribosomal RNA (rRNA)-based massively parallel genomic sequencing to profile bacterial communities in many anatomical sites from "normal and healthy" humans with no complications. These include publications on the bacterial communities in vaginal swab samples of nonpregnant women or "normal and healthy" pregnant women (Ravel, Gajer et al., 2011; Aagaard, Riehle et al., 2012, Gajer, Brotman et al., 2012). However, few have analyzed samples of women with pregnancy complications (Hummelen, Fernandes et al., 2010).

Specifically, one was a study on the bacterial communities in the vagina of HIV-positive women, which did not provide a dataset applicable to the major obstetric population without HIV (Hummelen, Fernandes et al., 2010). Another was a study on the bacterial communities in the placental samples delivered sooner than 37 weeks or after 37 weeks, which obviously did not facilitate a gestational age-matched comparison and thus involved a dataset confounded by gestational age difference (Aagaard, Ma et al., 2014). Thus, to-date, there is no publication on the systematic profiling of bacterial taxa in the cervix of women with such adverse outcomes and comparison with those in the cervix of gestational age-matched women without such complications.

Our current study provides the first systematic and relatively comprehensive profile on the bacterial communities in the cervical swab samples of pregnant women with complications (advanced cervical dilation or shortening). Moreover, for the first time, we systematically compare that profile of bacterial communities in the women with complications, with gestational age-matched women without such complications. Furthermore, for the first time, we provide a list of bacterial taxa which are differentially abundant in the cervix of women with such complications, compared with that of women without such complications. The provision of this list is an important groundwork for designing PCR assays to specifically target the "abnormal flora" in a gravid cervix, but not the "normal flora." Hence, we reason that our study provides data for improving the detection of advanced cervical dilation-associated bacteria.

Notably, the presence of selected members of this list of bacterial taxa between 13 to 25 gestational weeks is associated or predictive of adverse outcomes, including birth sooner 34 weeks, and intraventricular hemorrhage. Hence, we also reason that our list of bacterial taxa may also provide early prognosis of these adverse outcomes, so as to facilitate an early close-monitoring or transfer to a tertiary hospital with the proper neonatal care.

The purpose of the study described herein was to systematically profile all bacteria and identify a list of bacterial taxa and their partial genomic sequences that are differentially abundant in the cervix of women with advanced cervical dilation or cervical shortening.

Specifically, the study was designed to (i) systematically profile the bacterial taxa in the cervix of women with advanced cervical dilation ("the dilated cervix"), and compare with those in the cervix of appropriately-matched women without this condition ("the closed cervix"); (ii) to systematically profile the bacterial taxa in the cervix of women with cervical shortening ("the shortened cervix"), and compare with those in the cervix of appropriately-matched women without this condition ("the normal-length cervix"); (iii) to systematically identify a list of differentially abundant bacterial taxa in the dilated cervix, relative to those in the closed cervix using the data in (i); and (iv) to systematically identify a list of differentially abundant bacterial taxa in the shortened cervix, relative to those in the normal-length cervix using the data in (ii).

We have hypothesized that the bacterial communities colonizing the dilated cervix are different from those colonizing the normally closed cervix. To test this hypothesis, we have systematically profiled the bacterial taxa in the advanced dilated cervix ("the dilated cervix", n=19) and those in the normally closed cervix ("the closed cervix", n=13) using 16S ribosomal RNA (rRNA)-based massively parallel genomic sequencing. To systematically test for differentially abundant taxa between the two groups, we have compared the relative abundance of all the profiled taxa in the dilated cervix group and those in the closed cervix group using appropriate statistical procedures. To test if members of this list of bacterial taxa can predict any adverse pregnancy or neonatal outcomes, we have followed up these pregnancies from recruitment for this study till 28 days after birth, and calculated the sensitivity, specificity, positive predictive values, negative predictive values for predicting those outcomes whenever they were available.

Similarly, we have also systematically profiled the bacterial taxa in the shortened cervix (n=11), and compared with those from gestational age-matched controls with a normal-length cervix (n=11). We have also identified a list of differentially abundant taxa between the shortened cervix and the normal-length groups using statistical procedures and followed up the clinical outcomes. Whenever the outcomes were available, we have also assessed for predictive performance by selected members of that list.

Methods and Results

Recruitment of Participants.

This study was conducted with ethics approval from the respective institutional review board and samples were collected from pregnant women with informed consent. In the test group (the dilated cervix group, n=19), only pregnant women with painless advanced cervical dilation >0.8 cm were recruited.

Whereas, in the reference group (the closed cervix group, n=13), only pregnant women with no painless advanced cervical dilation >0.8 cm were recruited. Furthermore, to allow for fair comparison of results and clinical outcomes, in both the test and reference groups, only women (i) with no regular and frequent before 34 gestational weeks and (ii) with an indication to undergo cervical cerclage placement were recruited. The key characteristics of these 32 participants (19 in the dilated cervix group and 13 in the closed cervix group) are listed in Table 1.

To avoid complicating the phenotype (i.e., advanced cervical dilation), in both the test and the reference groups, pregnancies involving preeclampsia, multiple pregnancies, fetal distress, growth restriction, chromosomal or structural abnormalities at the time of sample collection were excluded. To minimize some major confounding factors affecting the bacterial communities in the cervix, participants who had sexual activities or applied any used any other vaginal applications (e.g., vaginal medication or suppositories, douche) 48 hours before sample collection or on antibiotic or antimycotic drugs 30 days before sample collection, or ovarian tumor were also excluded. Participants who had previous miscarriage or birth between 14 to 36 weeks (n=3, all in the dilated cervix group, Fisher exact test, p=0.253), previous surgical evacuation for miscarriage or termination of pregnancy (n=16, 9 dilated and 7 closed, p=1.00), cervical surgery (n=6, 2 dilated and 4 closed, p=0.194), uterine abnormality (n=6, 3 dilated and 3 closed, p=0.666), recent abnormal vaginal discharge (n=5, 4 dilated cervix and 1 closed, p=0.625) were clearly documented in our database. These factors were not statistically different between the two groups, but would be included for interpreting the data.

Collection and DNA extraction of cervical swab samples: To minimize the chance of contamination by the environment, the clinical staff or other parts of the female reproductive tract, the cervical swab sample was collected using a Calgiswab Type III (Puritan, Guilford, Me., USA) before any other procedures immediately upon opening up of the female reproductive tract by the speculum. To ensure the same anatomical locations were sampled and compared, each cervical swab sample was collected from a fixed position on the peripheral side (the 12 o'clock position facing the clinician) of the external os. To maintain consistency for fair comparison across all samples, a single clinician collected all samples from the dilated cervix and the closed cervix groups. To minimize variations in collection, each swab was collected by rotating 360 degrees once. To minimize any increased risk of infecting the participants or her fetus in the uterus, the swabs were collected without touching the cervical mucus plug and were sterile. During the collection of swab sample, extra care was also taken not to touch the labia or any parts of the female reproductive tract other than the external os. To monitor for contamination of bacteria in the operation room, the reagents and collection procedures, another negative control swab was collected in parallel with each cervical swab but without touching the patients.

The cervical swab and the negative control swabs were immersed in sterile and nuclease-free water and stored at −80° C. until extraction. The swabs were extracted for genomic DNA using an established method (Method 1 in Yuan, Cohen et al., 2012), which would ensure fair representation of bacterial communities commonly found in the female reproductive tracts. This method involved the pretreatment of the sample by the mutanolysin (Sigma-Aldrich) and a column-based DNA extraction method (QiaAmp DNA Mini Kit, Qiagen). To minimize any batch variation, all samples were extracted on the same day.

PCR amplification and massively parallel sequencing: Since the cervical swab samples inevitably would comprise human genomic DNA among the bacterial genomic DNA, we have specifically amplified the 16S rRNA gene, which is commonly possessed by all bacteria, but not by human. To facilitate the amplification of genomic DNA sequences of essentially all bacteria, we have chosen to use a pair of PCR primers, namely V4 and V5, which were complementary to the highly conserved regions 16S rRNA gene (Claesson, Wang et al. 2010). We have checked using the Ribosomal Database Project (RDP) (Wang, Garrity et al. 2007), the largest public database containing 16S rRNA sequences, that our chosen pair of PCR primers could theoretically amplified >97% of >9,200 typed (established) bacterial taxa of known 16S rRNA genomic sequences. Therefore, this pair of PCR primers is applicable for a systematic and non-biased profiling of bacterial communities in this study.

We amplified the genomic DNA extracted from each swab sample using the V4-V5 PCR primer pair (Claesson, Wang et al. 2010), which flanks the hypervariable regions V4 and V5 of the 16S rRNA gene. The sequences of the forward and reverse primers are 5'-[Primer A Key sequence] [MID sequence] AYT GGG YDT AAA GNG-3' (SEQ NO ID:1), and 5'-[Primer B-Key] CCG TCA ATT YYT TTR AGT TT-3'(SEQ ID NO: 2), respectively, where Primer A Key sequence, Primer B Key sequence and MID sequence are described in the "454 Sequencing System Guidelines for Amplicon Experimental Design July 2011" for the massively parallel sequencing platform GX-FLX 454 Titanium (Roche). Each PCR was performed as a 50-µL reaction with 2.5 units of the FastStart Taq DNA polymerase (FastStart HiFi PCR System dNTPack, Roche), 4 mM $MgCl_2$, 100 nM of each primer and 200 µM dNTPs. All PCR were run on a PTC-100 thermal cycler (Bio-Rad) using the following thermocycling conditions: 95° C. for 2 minutes, followed by 33 cycles of 95° C. for 30 seconds, 40° C. for 30 seconds, and 72° C. for 1 minute, with a final extension at 72° C. for 5 minutes and 25° C. for 5 minutes. We then subjected the PCR product to electrophoresis. We confirmed a single PCR amplicon of the expected size for all 32 cervical swab samples, and no PCR amplicon for all the 32 corresponding negative reagent controls. Thus, the environment, reagents and procedures were free from any contamination of unwanted bacterial 16S rRNA genomic sequences.

Subsequently, we purified all the 32 PCR products, which were derived from the 32 cervical swab samples and which were attached with the multiplex identifier (MID) sequences and adaptor sequences incorporated through the 5' ends of the PCR primers above, according to Roche's recommended instructions. The purified products were subjected to massively parallel genomic sequencing on using the GX-FLX 454 Titanium (Roche), according to manufacturer's instructions, targeting at an average of around 10,000 raw sequencing reads per sample.

For each samples, raw sequencing data were denoised at the flowgram level, using an implementation of Pyronoise (Quince, Lanzen et al., 2011) on mothur (Schloss, Westcott et al., 2009). Raw reads were flowgram-denoised, quality- and length-filtered, chimera-removed, aligned, pre-clustered and clustered into operational taxonomic units, which were then taxonomically classified, based on the Ribosomal Database Project (RDP) training set (v9, 2012).

Systematic identification of differentially abundant bacterial taxa between the dilated cervix group (n=19) and the closed cervix group (n=13): After all the above analytical steps, we have observed 342 bacterial taxa in the 32 cervical swab samples. To normalize the varying read counts across different samples, we performed random subsampling using mothur (Schloss, Westcott et al. 2009) so that each of the 32 samples contained 7,594 processed reads for further analysis. Alternatively, we have also normalized by representing the read counts of each taxon in a sample as a ratio of the total read counts from that sample.

To identify the differentially abundant taxa between the dilated cervix group and the closed cervix group, we performed a statistical test, namely Metastats, which is specially designed for this type of sequencing data (White, Nagarajan et al. 2009). In essence, Metastats features a non-parametric T-test and a heuristic to use Fisher exact test if a certain taxon appears at an average of less than 1 read per sample (the so-called sparse count problem which poses challenge for detecting significant changes in this type of data).

After removal of sequences of taxon that appeared only once (singleton sequences) and adjustment for multiple testing using the False Discovery Rate (FDR) method at FDR <5% (Storey and Tibshirani, 2003), 16 taxa remained as statistically significantly different (q<0.05). Among them, 9 taxa (Table 2A) were significantly increased and 7 taxa (Table 2B) were significantly decreased in the dilated cervix group, relative to the closed cervix group. The nearest taxonomic classification of these 16 genomic sequences at the level from kingdom to genus are listed in Tables 3A and 3B. The 16S rRNA genomic sequences are listed in Tables 4A and 4B. The nearest species classification of these 16 genomic sequences based on the BLAST nucleotide alignment against the 16S ribosomal RNA database (performed using the NCBI BLAST website in June 2014) are listed in Tables 4E and 4F.

Systematic identification of differentially abundant bacterial taxa between the dilated cervix group (n=10) and the closed cervix group (n=10) that were matched at 1:1 by the nearest gestational week at sample collection: The gestational age at sample collection between the two groups are not statistically significantly different. However, to minimize any effect of gestational age on our analysis, we have matched each woman in the dilated cervix group with another women in the closed cervix group by the nearest gestational week (within 2 weeks) at sample collection. Moreover, to minimize any effect of different sample sizes of the two groups, we have performed the above matching at a 1:1 ratio. Finally, we were able to match 10 women in the dilated cervix group with 10 women in the closed cervix group for the gestational week at sample collection.

After adjustment for multiple testing using the False Discovery Rate (FDR) method at FDR <5% (Storey and Tibshirani, 2003), 20 taxa remained as statistically significantly different (q<0.05). Among them, 15 taxa (Table 2C) were significantly increased and 5 taxa (Table 2D) were significantly decreased in the dilated cervix group, relative to the closed cervix group. The nearest taxonomic classification of these 20 genomic sequences at the level from kingdom to genus are listed in Tables 3D and 3C. The 16S rRNA genomic sequences are listed in Tables 4C and 4D. The nearest species classification of these 16 genomic sequences based on the BLAST nucleotide alignment against the 16S ribosomal RNA database (performed using the NCBI BLAST website in June 2014) are listed in Tables 4G and 4H.

Predictive performance by selected members of the lists of differentially abundant bacterial taxa on various outcomes. We selected all 9 taxa from Table 2A and all 15 taxa with from Table 2C to construct two tests, namely the Differentially Increased Bacteria Test (DIBT) 1 and DIBT2, respectively.

DIBT1 and DIBT2 may use massively parallel genomic sequencing data or, more preferably, data from species-specific PCR for detecting the presence of a given bacterial taxon. If any of these 9 or 15 differentially increased taxa was present in that sample, we defined it as DIBT1 positive or DIBT2 positive, respectively. Otherwise, if all of these 9 or 15 taxa are absent in a sample, we defined it as DIBT1 negative or DIBT2 negative, respectively To explore the association between DIBT1 or DIBT2 and adverse pregnancy or neonatal outcomes, we performed the Fisher exact test. To explore the potential of DIBT1 or DIBT2 in predicting key pregnancy and neonatal outcomes, we calculated the true positives, false positives, false negatives and true negatives of DIBT1 or DIBT2 in predicting these outcomes (Tables 5A and 5B, respectively). Also, we calculated the sensitivity, specificity, positive and negative predictive values of DIBT1 and DIBT2 in predicting these outcomes (Tables 5A and 5B, respectively).

There are significant associations between DIBT1 and advanced cervical dilation (Fisher exact test, p=0.028), spontaneous preterm birth <28 weeks (p=0.0023), spontaneous preterm birth <34 weeks (p=0.00065), preterm birth <28 weeks (p=0.0057), preterm birth <34 weeks (p=3.2× $10^{-6}$) and intraventricular hemorrhage (p=0.01). Of note, all 7 cases of spontaneous preterm birth were detected as DIBT1 positive (no false negatives). Also of note, among all 13 cases classified as DIBT1 positives, all underwent preterm birth <34 weeks (no false positives). All these preterm births were not due to preeclampsia, intrauterine growth restriction, fetal chromosomal abnormality). Thus, we speculate these 13 preterm births may be triggered by infection of one or more of these "abnormal flora" we identified by in this study and selected for inclusion in the DIBT1.

As for DIBT2, significant associations are observed between it and spontaneous preterm birth <28 weeks (p=0.0023), spontaneous preterm birth <34 weeks (p=0.00065), preterm birth <28 weeks (p=0.0057), preterm birth <34 weeks (p=0.0032). Of note, all 7 cases of spontaneous preterm birth <34 weeks were detected by DIBT2 as positive (no false negatives).

In another study (study B), we have performed a similar analysis on cervical swab samples collected at matched gestational age, but from women with a short cervix or with a normal length cervix (Table 6). For each sample, DNA was extracted and PCR-amplified by the V4V5 primers and subjected to GS-FLX 454 analysis. After adjustment for multiple testing using the False Discovery Rate (FDR) method at FDR <5% (Storey and Tibshirani, 2003), 24 taxa remained as statistically significantly different (q<0.05). Among them, 17 taxa (Table 7) were significantly increased and 7 taxa (not shown) were significantly decreased in the short cervix group, relative to the normal-length cervix group. The 16S rRNA genomic sequences are listed in Table 8. The nearest species classification of these 17 genomic sequences based on the BLAST nucleotide alignment against the 16S ribosomal RNA database (performed using the NCBI BLAST website in June 2014) are listed in Table 9.

Predictive performance by selected members of the lists of differentially abundant bacterial taxa on various outcomes. We selected all 17 taxa from Table 7 to construct another test, namely the Differentially Increased Bacteria Test (DIBT) 3.

DIBT3 may use massively parallel genomic sequencing data or, more preferably, data from species-specific PCR for detecting the presence of a given bacterial taxon. If any of these 17 differentially increased taxa was present in that sample, we defined it as DIBT3 positive. Otherwise, if all of these 17 taxa are absent in a sample, we defined it as DIBT3 negative, respectively. The association of the DIBT3 positive results and adverse pregnancy or neonatal outcome is tabulated in Table 10.

There are significant associations between DIBT3 and premature cervical dilation (Fisher exact test, p=0.00022), spontaneous preterm birth <34 weeks (p=0.049), preterm birth <34 weeks (p=0.049). Of note, all 3 cases of spontaneous preterm birth were detected as DIBT3 positive (no false negatives).

The bacterial markers provided herein were used to accurately predict adverse pregnancy outcomes and neonatal outcomes based on a molecular test performed as early as 13 weeks of gestation (Tables 5A, 5B and 10). The method described herein facilitates early intervention, such as close monitoring or timely transfer to a tertiary treatment unit with neonatal intensive care.

Example 2: Cervical Microbiome Signature for the Identification of Cervical Insufficiency Patients Resulting in Spontaneous Preterm Birth after Clinical Intervention Bacterial taxa colonizing the cervices of cervical insufficiency (CI) patients responding differently to clinical intervention (cerclage/pessary) have not been systematically investigated. Using massively parallel sequencing, we interrogated the abundances of over 9,600 taxa per cervical swab sample obtained before intervention from serially-recruited singleton-pregnancy CI patients and appropriately-matched women without CI. We observed that the cervical microbiomes were altered in the CI patients, compared with those of the non-CI controls. Notably, we identified 6 differentially abundant taxa in patients resulting in "spontaneous preterm birth (<34 weeks, sPTB) after intervention", compared with those resulting in "term birth (≥37 weeks) after intervention". Using the $\log_{10}$ (total abundance of these 6 taxa), LA6, >1.15 to define a positive result, we correctly classified all but one patients resulting in "sPTB after intervention" (9/10=90%), with no false positive (0/15=0%). LA6-positive patients, remained undelivered for a shorter period after intervention [median number days between intervention and delivery, 10 days vs. 126 days; Logrank test, p<0.00001; hazard ratio, 6.34; 95% confidence interval, 1.51 to 26.6], compared with LA6-negative patients. Moreover, LA6-positive patients delivered earlier than their LA6-negative counterparts [median gestational age at delivery of 23.7 weeks vs. 38.4 weeks; Logrank test, p<0.0001; hazard ratio, 6.24; 95% confidence interval, 1.50 to 25.9]. Our study highlights the potential use of the pre-intervention cervical microbiome to provide prognostic information of the pregnancy after the cerclage/pessary intervention.

Introduction

Cervical insufficiency (CI) is a risk factor for preterm birth (PTB), which is associated with neonatal morbidity and perinatal death. It is manifested in the affected women as having a prematurely dilated (cervical dilation, 1 cm-5 cm) or shortened cervix (cervical length <25 mm) in the second, instead of the third, trimester. Clinical intervention by the placement of surgical cerclage or cervical pessary (Shirodkar, Antiseptic, 52, 299-300 (1955); Cross, Lancet, 274, 127 (1959)) on the weakened cervix of CI patients has been shown to decrease the rate of PTB<28 weeks (Pereira et al., Am J Obstet Gynecol 197, 483 e481-488 (2007)) or PTB<34 weeks (Althuisius et al., Am J Obstet Gynecol 189, 907-910 (2003); Goya et al., Lancet 379, 1800-1806 (2012)), increase the rate of neonatal survival (3), and the interval between presentation and delivery (Pereira et al., Am J Obstet Gynecol 197, 483 e481-488 (2007)).

Nevertheless, the cervical intervention does not benefit every CI patient. In particular, CI patients with intraamniotic infection (IAI) resulted in a 4-fold higher rate of PTB<34 weeks after cerclage intervention (Romero et al., Am J Obstet Gynecol 167, 1086-1091 (1992)), compared with those receiving the same intervention but with no IAI. Patients who received cerclage intervention only if IAI was ruled out resulted in a lower rate of PTB<34 weeks, compared to those who received the intervention without testing for IAI (Mays et al., Obstet Gynecol 95, 652-655 (2000)). Since IAI is highly prevalent (38%-51%) in CI patients (Romero et al., Am J Obstet Gynecol 167, 1086-1091 (1992); Mays et al., Obstet Gynecol 95, 652-655 (2000)), experts have suggested clinicians to consider ruling out IAI using pre-cerclage amniocentesis to detect for microorganisms (Berghella et al., Am J Obstet Gynecol 209, 181-192 (2013); Airoldi et al., Am J Perinatol 26, 63-68 (2009)). However, amniocentesis is invasive and associated with a small but finite chance of fetal loss. Thus, we investigated the cervical colonization in CI patients and correlated the expression of the microbiome with outcomes of the cervical intervention. The results show that cervical swab sampling may be a relatively non-invasive alternative to amniocentesis on CI patients.

Massively parallel sequencing (MPS) has facilitated a culture-independent and hence provided more sensitive and comprehensive view of microorganisms colonizing different body sites. Conventionally, the placenta which is located inside the amniotic cavity has been thought to be sterile. Contrary to this, a MPS-based microbiome and metagenomic study published in this journal has revealed that the placenta harbors a low biomass microbiome that varies in association with a remote history of maternal antenatal infection and preterm birth (Aagaard et al., Sci Transl Med 6, 237ra265 (2014)). The present study was performed to investigate the association between the antenatal cervical microbiome and the outcome of preterm birth from CI patients.

The high-resolution data generated by MPS and the quantitative information that can be inferred from them have also broadened our knowledge on microorganisms in women's health. Five major classes of bacterial communities (community groups) have been observed in the vaginal tract of reproductive-age non-pregnant women. In women whose vaginal proportion of non-*Lactobacillus* sp. increased as commonly seen in community group IV, their Nugent scores, a diagnostic factor commonly used to identify women with bacterial vaginosis, also increased (Ravel et al., Proc Natl Acad Sci USA 108, 4680-4687 (2011)). Notably, women with bacterial vaginosis were more likely to have a dilated cervix (adjusted odds ratio, 4.9; 95% confidence interval 2.2-10.9) (Kilpatrick et al., Am J Obstet Gynecol 194, 1168-1176 (2006)). Longitudinal study of the vaginal microbiome in non-pregnant women has revealed that some bacterial communities change markedly over short time periods, whereas others are relatively stable (Gajer et al., Sci Transl Med 4, 132ra152 (2012)). It is reasoned from ecological theory that less stable communities are more susceptible to invasion by pathogenic organisms (Dunstan et al., Ecology 87, 2842-2850 (2006)). In this study the cervical microbiomes in CI patients were compared with those of appropriately-matched women without CI.

Results

We recruited 34 cervical insufficiency (CI) patients and obtained a cervical swab sample from each before cerclage/pessary treatment. The second-trimester singleton-pregnancy women participating in this study all had: (i) painless advanced cervical dilation (1.5 cm-5.0 cm) and/or cervical shortening (cervical length <25 mm), and; (ii) intact membrane, and; (iii) no labour contractions; during the time of cervical swab sampling.

All these CI patients received cerclage/pessary intervention due to the prematurely dilated/shortened cervix, respectively. The patients were followed up until one month after delivery. Nine pregnancies complicated by iatrogenic PTB due to preeclampsia, fetal distress, growth restriction, fetal chromosomal or structural abnormalities were excluded. Among the 25 remaining CI patients, 15 women resulted in term births (TB, delivered on or after 37 weeks of gestation) after intervention and 10 resulted in spontaneous preterm births (sPTB, delivered at less than 34 weeks) after intervention (FIG. 1A). Of these, 7 involved neonatal morbidity including respiratory distress syndrome (RDS), bronchopulmonary dysplasia (BPD), intraventricular haemorrhage (IVH) and retinopathy of prematurity (ROP) or perinatal mortality (FIG. 1A).

Profiling Bacterial Taxa by Massively Parallel

Each cervical swab sample collected before the clinical intervention was subjected to extraction of bacterial DNA, PCR amplification of the 16S ribosomal RNA (rRNA) gene and massively parallel sequencing of the amplicon (Titanium, GS-FLX 454, Roche). The PCR primers targeting the V4 and V5 regions of the 16S rRNA gene could amplify over 9,600 well-established bacteria of known 16S rRNA sequences for analysis (Claesson et al., Nucleic Acids Res 38, e200 (2010)). This scope was wider than most of the published microbiome studies of the female reproductive tract.

To minimize spurious detection of "new" taxa arising from sequencing errors, the raw sequencing reads (0.68 million reads) were denoised and quality-filtered into processed reads (0.54 million reads) using well-established methods (Schloss et al., Appl Environ Microbiol 75, 7537-7541 (2009); Quince et al., Nat Methods 6, 639-641 (2009)). On average, each of the 25 samples was sequenced at a depth of 22,000 processed high-quality reads. Such a sequencing depth was greater than most of the published microbiome studies of the female reproductive tract.

Further, the processed reads from all samples with at least 97% sequence identity were clustered as one operational taxonomic unit (Otu, i.e., a bacterial taxon). Totally, 152 bacterial taxa were detected in all 25 cervices. To allow fairer comparison across samples sequenced at different read counts, we have performed the Cumulative Sum Scaling (CSS) normalization (Paulson et al., Nat Methods 10, 1200-1202 (2013)) and expressed the abundance value (unit: read counts) for each taxon as its CSS-normalised read count in the $\log_{10}$ scale (i.e., the log(abundance) value).

Highly Abundant Bacterial Taxa in Cervical Insufficiency Patients

FIG. 1B shows the 10 most abundant bacterial taxa observed in the 10 "sPTB after intervention" cervices. Contrary to a healthy female reproductive tract predominated by Lactobacilli, a member of the *Gardnerella* genus (Otu 4) has been identified as the most abundant bacterial taxa in the "sPTB after treatment" cervices [FIG. 1B, row #1, i.e., the taxon with the greatest total log(abundance) values in the 10 "sPTB after intervention" cervices]. In fact, 7 of the 10 most abundant bacterial taxa in this group have been classified as non-*Lactobacillus* genera: *Gardnerella*, two *Sneathias*, *Aerococcus*, *Megasphaera*, *Pseudomonas* and *Anaerococcus* (FIG. 1B, rows #1 to #10 and columns under "sPTB").

In comparison, only 5 of the 10 most abundant bacterial taxa in the "TB after treatment" cervices have been classified as non-*Lactobacillus* genera (FIG. 1C, rows #1 to #10 and columns under "TB"). Notably, the 3 most abundant bacteria have been identified as *Lactobacillus crispatus*, *L. iners*, and *L. jensenii*, which are known to predominate the healthy female reproductive tract (Ravel et al., *Proc Natl Acad Sci USA* 108, 4680-4687 (2011)).

Differentially Abundant Taxa in Patients with Different Responses to Intervention Importantly, we have identified 7 bacterial taxa to be differentially abundant between the "sPTB after treatment" and the "TB after treatment" groups (FIG. 1D). The log (abundance) values of the 7 taxa, namely *Sneathia* (Otu 11), *Parvimonas* (Otu 16), *Ureaplasma* (Otu 56), *Atopobium* (Otu 42), *Peptoniphilus* (Otu 28), *Megasphaera* (Otu 47) and *Paraeggerthella* (Otu 40), were higher in the former group (Mann-Whitney rank sum test, p<0.05; multiple testing correction was performed using the False Discovery Rate (FDR) method, FDR<5%) (FIG. 1D, rows #1 to #7, last column). Strikingly, of these, the latter 6 taxa were exclusively observed only in the "sPTB after treatment", but not the "TB after treatment", group [FIG. 1D, rows #2 to #7, many log(abundance) values under the "sPTB" columns are >0, but all log(abundance) values under the "TB" columns are 0].

Differentially Abundant Taxa and Outcome after Intervention

To summarize the abundances of the latter 6 differentially abundant taxa (Mann-Whitney, p<0.01; Table 11), we have calculated for each cervical swab sample a LA6 value, which refers to the log 10(total abundance of the 6 differentially abundant taxa). Briefly, for each sample, we transformed each of its log(abundance) values for *Parvimonas* (Otu 16), *Ureaplasma* (Otu 56), *Atopobium* (Otu 42), *Peptoniphilus* (Otu 28), *Megasphaera* (Otu 47) and *Paraeggerthella* (Otu 40) back into the common linear scale. After adding those 6 abundance values in the common scale, we log-transformed that total abundance and expressed the LA6 value in the $\log_{10}$ scale.

The median values of LA6 were 2.61 and 0.78 in the "sPTB after treatment" and the "TB after treatment" groups, respectively (FIG. 2A). The median LA6 values are shown to be increased by 3.36-fold in the former group (Mann-Whitney, p<0.0001). To find the optimal threshold in identifying the "sPTB after treatment" group among CI patients receiving treatment, we have plotted the receiver-operating characteristics (ROC) curve [area under ROC curve (95% confidence interval), 0.95 (0.84-1.06); p=0.0002]. Using the LA6>1.15 as a threshold in defining a positive result, we could identify all but one "sPTB after intervention" CI patients (9/10=90% sensitivity) with no false positive (1-0/15=100% specificity).

Figure 2B:
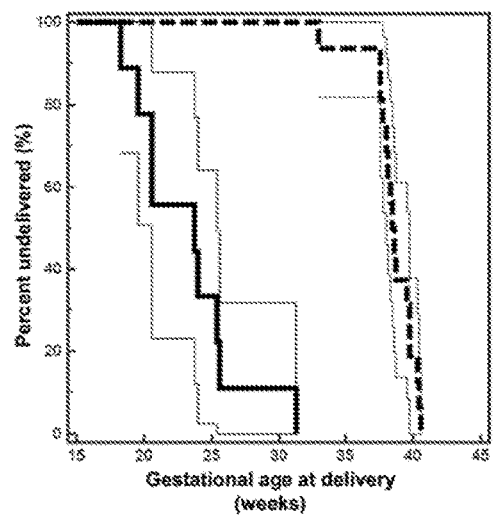
Figure 2C:
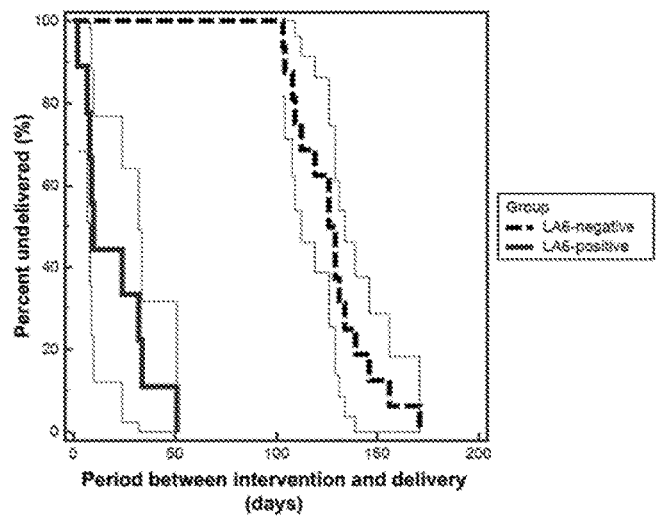

Importantly, LA6-positive patients delivered earlier after clinical intervention than the LA6-positive patients (FIG. 2B, median gestational age at delivery of 23.7 weeks vs. 38.4 weeks; 95% confidence interval, 20.6 weeks-25.4 weeks vs. 38.0 weeks-38.7 weeks; Chi-squared, 32.352; df, 1; Logrank test, p<0.0001; hazard ratio, 6.24; 95% confidence interval, 1.50 to 25.9; MedCalc, version 14.12). Also importantly, LA6-positive patients delivered for a shorter period after intervention than their LA6-negative counterparts (FIG. 2C median number days between intervention and delivery, 10 days vs. 126 days; 95% confidence interval, 8 days-32 days vs. 112 days-134 days; Chi-squared, 32.520; df, 1; Logrank test, p<0.00001; hazard ratio, 6.34; 95% confidence interval, 1.51 to 26.6)

Discussion

Cervical Microbiome Signature Identified in this Study

We have shown that the abundances of 7 bacterial taxa in CI patients were significantly increased in the women resulting in "sPTB after clinical intervention", compared with those resulting in "TB after clinical intervention". Further, we have calculated the LA6 value, which represents the total abundance values of the 6 most significantly increased taxa, for each CI patient. Based on the LA6 values of the 25 cervical swab samples obtained before cerclage/pessary intervention, we correctly identified 10 out of 11 "sPTB after intervention" CI patients (9/10=90% sensitivity) without any false positive in the 15 "TB after intervention" patients (1-0/15=100% specificity).

This study was limited by its sample size of Asian pregnant women and involved a retrospective design. Nevertheless, it has provided a non-obvious, focused, panel of bacterial taxa which is associated with CI, an important risk for preterm birth. The cervical microbiome signature identified in this study, namely LA6, has been illustrated to provide prognostic information after cerclage/pessary intervention. Apparently, CI patients tested positive for LA6 are at an increased risk to deliver at a significantly earlier gestational age after clinical intervention than those tested negative (23.7 weeks vs. 38.4 weeks; hazard ratio, 6.24; 95% confidence interval, 1.50 to 25.9). Not only so, LA6-positive patients are also at an increased risk to deliver much sooner after intervention than their LA6-negative counterparts (10 days vs. 126 days; hazard ratio, 6.34; 95% confidence interval, 1.51 to 26.6).

Materials and Methods

Recruitment of Participants

Ethics approval for conducting this study was obtained from the respective Institutional Review Board. Informed consent were obtained from Asian pregnant women attending the Department of Obstetrics and Gynaecology, Prince of Wales Hospital, The Chinese University of Hong Kong or the Department of Obstetrics and Gynaecology, Hallym University, Seoul, South Korea and fulfilling the following inclusion criteria: (i) painless cervical dilation (1.0 cm-5.0 cm) in the second trimester; and (ii) intact membrane and; (iii) no labour contractions (once per 10 minutes). Women were excluded from this study if they had: (a) a multiple pregnancy (≥2 fetuses); or (b) coitus or applied any vaginal applications 48 hours before collection of the cervical swab sample; or (c) used antibiotic/antimycotic drugs 30 days before collection of the cervical swab sample.

Cervical Swab Collection

Before the cerclage treatment, a cervical swab sample was collected from the CI patient by rotating a sterile Dacron swab 360° once on the external os. For dilated cervix, the swab was obtained from the os at the 12 o'clock position facing the clinician. The swab sample was collected immediately upon opening up of the reproductive tract by speculum, and before any other procedures. Antiseptic techniques were applied. Special care was taken to avoid the swab to come into contact with any part of the reproductive tract (e.g., vagina, labia), other than that designated location of the cervix.

Bacterial DNA Extraction

We extracted for bacterial genomic DNA in each sample according to a published protocol, which was optimized to maintain good representation of bacterial taxa in a sample (Yuan et al., *PLoS One* 7, e33865 (2012)).

Taxonomic Classification

Each Otu is taxonomically classified at the genus level using the Ribosomal Database Project (RDP) Naïve Bayesian rRNA Classifier (Version 2.9, September 2014, RDP 16S rRNA training set 10). *Lactobacillus* are further matched against the 16S rRNA database (GenBank) using BLAST (highest score) and MOLE-BLAST (best multiple-alignment of BLAST matches) for deriving the species information.

REFERENCES

Aagaard. K., J. Ma, K. M. Antony, R Ganu. J. Petrosino and J. Versalovic (2014). "The placenta harbors a unique microbiome." Sci Transl Med, 6(237): 237-265.

Aagaard, K., K. Riehle, J. Ma, N. Segata, T. A Mistretta, C. Coarfa, S Raza, S. Rosenbaum, I. Van den Veyver, A. Milosavljevic, D Gevers, C. Huttenhower, J Petrosino and J. Versalovic (2012). "A metagenomic approach to characterization of the vaginal microbiome signature in pregnancy." PLoS One 7(6): e36466.

Claesson, M. J., Q. Wang, O. O'Sullivan, R Greene-Diniz, J. R Cole, R P. Ross and P. W O'Toole (2010). "Comparison of two next-generation sequencing technologies for resolving highly complex microbiota composition using tandem variable 16S rRNA gene regions." Nucleic Acids Res 38(22): e200.

Gajer. P., R M. Brotman, G. Bai, J. Sakamoto, U M. Schutte, X. Zhong, S. S. Koenig, L. Fu, Z. S. Ma, X. Zhou, Z Abdo, L. J. Forney and J. Ravel (2012). "Temporal dynamics of the human vaginal microbiota." Sci Trans Med 4(132): 132-152.

Gerber, S., Y. Vial, P. Hohlfeld and S. S. Witkin (2003). "Detection of *Ureaplasma urealyticum* in second-trimester amniotic fluid by polymerase chain reaction correlates with subsequent preterm labor and delivery." J Infect Dis 187(3): 518-521.

Gray, D. J., H. B. Robinson, J. Malone and R. B Thomson, Jr. (1992). "Adverse outcome in pregnancy following amniotic fluid isolation of *Ureaplasma urealyticum*." Prenat Diagn 12(2): 111-117.

Hummelen, R, A. D. Fernandes, J. M. Macklaim, R J. Dickson, J. Changalucha, G. B. Gloor and G. Reid (2010). "Deep sequencing of the vaginal microbiota of women with HIV." PLoS One 5(8): e12078.

Oh, K. J., S. E. Lee, H. Jung, G. Kim, R. Romero and B. H. Yoon (2010). "Detection of *ureaplasmas* by the polymerase chain reaction in the amniotic fluid of patients with cervical insufficiency." J Perinat Med 38(3): 261-268.

Owen, J., G. Hankins, J. D. Iams, V. Berghella, J. S. Sheffield. A. Perez-Delboy, R S. Egennan, D. A. Wing, M. Tomlinson. R Silver, S. M. Ramin, E. R Guzman, M. Gordon, H. Y. How, E. J. Knudtson, J. M Szvchowski. S. Cliver and J. C. Hauth (2009). "Multicenter randomized trial of cerclage for preterm birth prevention in high-risk women with shortened midtrimester cervical length." Am J Obstet Gynecol 201(4): 375 e371-378.

Perni, S. C., S. Vardhana, I. Korneeva, S. L Tuttle, L. R Paraskevas, S. T. Chasen, R. B. Kalish and S. S. Witkin (2004). "*Mycoplasma hominis* and *Ureaplasma urealyticum* in midtrimester amniotic fluid: association with amniotic fluid cytokine levels and pregnancy outcome." Am J Obstet Gynecol 191(4): 1382-1386.

Quince, C., A. Lanzen, R J. Davenport and P J. Turnbaugh (2011). "Removing noise from pyrosequenced amplicons." BMC Bioinformatics 12: 38.

Ravel, J., P. Gajer, Z. Abdo, G. M. Schneider, S S. Koenig, S. L. McCulle, S. Karlebach, R Gorle, J. Russell, C. O. Tacket, R. M. Brotman, C. C. Davis, K. Ault, L. Peralta and L. J. Forney (2011). "Vaginal microbiome of reproductive-age women." Proc Natl Acad Sci USA 108 Suppl 1: 4680-4687.

Romero, R, R Gonzalez, W. Sepulveda. F. Brandt, M Ramirez, Y. Sorokin. M. Mazor, M. C. Treadwell and D. B. Cotton (1992). "Infection and labor. VII. Microbial invasion of the amniotic cavity in patients with suspected cervical incompetence: prevalence and clinical significance." Am J Obstet Gynecol 167(4 Pt 1): 1086-1091.

Schloss, P. D., S. L. Westcott, T. Ryabin, J. R. Hall, M. Hartmann, E. B. Hollister, R A. Lesnmewski, B. B. Oakley, D. H. Parks, C. J. Robinson, J. W. Sahl, B. Stres, G. G., Thallinger, D. J. Van Horn and C. F. Weber (2009). "Introducing mothur: open-source, platform-independent, community-supported software for describing and comparing microbial communities." Appl Environ Microbiol 75(23); 7537-7541.

Storey, J. D. and R. Tibshirani (2003). "Statistical significance for genomewide studies." Proc Natl Acad Sci USA 100(16): 9440-9445.

Wang, Q., G. M. Garrity, J M. Tiedje and J. R Cole (2007). "Naive Bayesian classifier for rapid assignment of rRNA sequences into the new bacterial taxonomy." Appl Environ Microbiol 73(16): 5261-5267.

White, J. R, N. Nagarajan and M. Pop. (2009) "Statistical methods for detecting differentially abundant features in clinical metagenomic samples." PLoS Comput Biol 5(4): e1000352.

Yuan, S., D. B. Cohen, J. Ravel, Z. Abdo and L. J. Forney (2012). "Evaluation of methods for the extraction and purification of DNA from the human microbiome." PLoS One 7(3): e33865.

All patents, patent applications, and other publications including sequences referred to by GenBank Accession Numbers cited in this application are incorporated by reference in the entirety for all purposes.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

TABLE 1

Key characteristics of all participants.

| | Dilated cervix (n = 19) | Closed cervix (n = 13) | p-value* |
|---|---|---|---|
| Gestational age at swab collection (weeks) [mean ± SD] | 20.7 ± 3.3 | 18.8 ± 3.8 | p = 0.283 |
| Previous history of miscarriage or preterm birth (n, %) | 3 (16%) | 0 (0%) | p = 0.253 |
| Cervical length at swab collection (mm) [mean ± SD] | 7.9 ± 11.9 | 23.9 ± 6.6 | p < 0.001 |
| Number of women with cervix dilated (n, %) [mean dilation ± SD] | 19 (100%) [1.9 cm ± 1.25 cm] | 0 (0%) | p < 0.001 |
| Number of women underwent cervical cerciage (n, %) | 19 (100%) | 13 (100%) | p = 1.00 |
| Number of women with basic pregnancy outcomes** (n, %) | 18 (95%) | 13 (100%) | p = 1.00 |

*Mann-Whitney rank sum test for continuous variables. Fisher exact test for categorical variables.
**Gestational age at delivery, mode of delivery and birthweight.

TABLE 2A

Sequencing data of the differentially abundant (significantly increased) bacterial taxa identified by comparing all 342 taxa in the 19 dilated vs. the 13 closed cervices (normalized by random subsampling).

| Taxon | Mean relative abundance (dilated) | Standard error (dilated) | Mean relative abundance (closed) | Standard error (closed) | Fold-change (increased) | p-value | Adjusted p-value * |
|---|---|---|---|---|---|---|---|
| d-c-019 | 1.10E−03 | 1.10E−03 | 0.00E+00 | 0.00E+00 | 33.2 | 9.99E−04 | 6.85E−03 |
| d-c-030 | 3.67E−04 | 3.67E−04 | 0.00E+00 | 0.00E+00 | 11.1 | 9.99E−04 | 6.85E−03 |
| d-c-037 | 1.25E−04 | 8.10E−05 | 0.00E+00 | 0.00E+00 | 3.8 | 1.16E−04 | 2.65E−03 |
| d-c-040 | 1.25E−04 | 1.25E−04 | 0.00E+00 | 0.00E+00 | 3.8 | 1.16E−04 | 2.65E−03 |
| d-c-043 | 1.25E−04 | 8.50E−05 | 0.00E+00 | 0.00E+00 | 3.8 | 1.16E−04 | 2.65E−03 |
| d-c-045 | 1.11E−04 | 7.80E−05 | 0.00E+00 | 0.00E+00 | 3.4 | 3.93E−04 | 6.74E−03 |
| d-c-038 | 1.04E−04 | 9.00E−05 | 0.00E+00 | 0.00E+00 | 3.1 | 7.37E−04 | 6.85E−03 |
| d-c-047 | 8.30E−05 | 7.00E−05 | 0.00E+00 | 0.00E+00 | 2.5 | 2.29E−03 | 1.21E−02 |
| d-c-054 | 8.30E−05 | 8.30E−05 | 0.00E+00 | 0.00E+00 | 2.5 | 2.29E−03 | 1.21E−02 |

* Adjusted for multiple testing by the False Discovery Rate method.

TABLE 2B

Sequencing data of the differentially abundant (significantly decreased) bacterial taxa identified by comparing all 342 taxa in the 19 dilated vs. the 13 closed cervices (normalized by random subsampling).

| Taxon | Mean relative abundance (dilated) | Standard error (dilated) | Mean relative abundance (closed) | Standard error (closed) | Fold-change (decreased) | p-value | Adjusted p-value * |
|---|---|---|---|---|---|---|---|
| d-c-067 | 7.00E−06 | 7.00E−06 | 9.10E−05 | 6.20E−05 | 13.0 | 1.91E−03 | 1.19E−02 |
| d-c-039 | 0.00E+00 | 0.00E+00 | 2.43E−04 | 2.43E−04 | 7.4 | 9.99E−04 | 6.85E−03 |
| d-c-052 | 0.00E+00 | 0.00E+00 | 1.82E−04 | 1.82E−04 | 5.5 | 9.99E−04 | 6.85E−03 |
| d-c-074 | 0.00E+00 | 0.00E+00 | 8.10E−05 | 8.10E−05 | 2.5 | 7.42E−04 | 6.85E−03 |
| d-c-082 | 0.00E+00 | 0.00E+00 | 6.10E−05 | 6.10E−05 | 1.8 | 4.50E−03 | 2.20E−02 |
| d-c-092 | 0.00E+00 | 0.00E+00 | 5.10E−05 | 5.10E−05 | 1.5 | 1.11E−02 | 4.74E−02 |
| d-c-098 | 0.00E+00 | 0.00E+00 | 5.10E−05 | 5.10E−05 | 1.5 | 1.11E−02 | 4.74E−02 |

* Adjusted for multiple testing by the False Discovery Rate method.

TABLE 2C

Sequencing data of the differentially abundant (significantly increased) bacterial taxa identified by comparing all 349 taxa in the 10 dilated vs. the 10 closed cervices (1:1 matched by gestational age at sample collection, matched to <2 weeks, normalized as ratio of total read count for each sample.).

| Taxon | Mean relative abundance (dilated) | Standard error (dilated) | Mean relative abundance (closed) | Standard error (closed) | Fold-change (increased) | p-value | Adjusted p-value * |
|---|---|---|---|---|---|---|---|
| d-c-012 | 1.75E−03 | 1.75E−03 | 0.00E+00 | 0.00E+00 | 53.0 | 9.99E−04 | 7.38E−03 |
| d-c-030 | 5.93E−04 | 5.93E−04 | 0.00E+00 | 0.00E+00 | 18.0 | 9.99E−04 | 7.38E−03 |
| d-c-040 | 1.49E−04 | 1.49E−04 | 0.00E+00 | 0.00E+00 | 4.5 | 9.99E−04 | 7.38E−03 |
| d-c-047 | 1.20E−04 | 8.50E−05 | 0.00E+00 | 0.00E+00 | 3.6 | 9.99E−04 | 7.38E−03 |
| d-c-050 | 1.07E−04 | 8.50E−05 | 0.00E+00 | 0.00E+00 | 3.2 | 9.99E−04 | 7.38E−03 |
| d-c-081 | 7.80E−05 | 7.80E−05 | 0.00E+00 | 0.00E+00 | 2.4 | 6.09E−04 | 7.38E−03 |
| d-c-053 | 7.40E−05 | 6.70E−05 | 0.00E+00 | 0.00E+00 | 2.2 | 9.99E−04 | 7.38E−03 |
| d-c-015 | 7.00E−05 | 7.00E−05 | 0.00E+00 | 0.00E+00 | 2.1 | 1.39E−03 | 7.68E−03 |
| d-c-088 | 7.00E−05 | 7.00E−05 | 0.00E+00 | 0.00E+00 | 2.1 | 1.39E−03 | 7.68E−03 |
| d-c-072 | 5.60E−05 | 4.40E−05 | 0.00E+00 | 0.00E+00 | 1.7 | 9.99E−04 | 7.38E−03 |
| d-c-105 | 5.20E−05 | 5.20E−05 | 0.00E+00 | 0.00E+00 | 1.6 | 7.19E−03 | 3.35E−02 |
| d-c-068 | 3.60E−05 | 3.60E−05 | 0.00E+00 | 0.00E+00 | 1.1 | 9.99E−04 | 7.38E−03 |
| d-c-071 | 3.60E−05 | 3.60E−05 | 0.00E+00 | 0.00E+00 | 1.1 | 9.99E−04 | 7.38E−03 |
| d-c-083 | 2.60E−05 | 2.60E−05 | 0.00E+00 | 0.00E+00 | 0.8 | 1.39E−03 | 7.68E−03 |
| d-c-087 | 2.60E−05 | 2.60E−05 | 0.00E+00 | 0.00E+00 | 0.8 | 1.39E−03 | 7.68E−03 |

* Adjusted for multiple testing by the False Discovery Rate method.

TABLE 3A

Genus level classification of the differentially abundant (significantly increased) bacterial taxa identified by comparing all 342 taxa in the 19 dilated vs. the 13 closed cervices (normalized by random subsampling).

| Taxon | Taxonomic classification of the identified taxon at the level of kingdom, phylum, class, family, order and genus with classification score (in brackets.) |
|---|---|
| d-c-019 | Bacteria(100); Firmicutes(100); Bacilli(100); Lactobacillales(100); Lactobacillaceae(100); *Lactobacillus*(100); |
| d-c-030 | Bacteria(100); Firmicutes(100); Negativicutes(100); Selenomonadales(100); Veillonellaceae(100); Veillonella(100); |
| d-c-037 | Bacteria(100); Firmicutes(100); Negativicutes(100); Selenomonadales(100); Veillonellaceae(100); unclassified(93); |
| d-c-040 | Bacteria(100); "Actinobacteria"(100); Actinobacteria(100); Bifidobacteriales (100); Bifidobacteriaceae(100); Alloscardovia(100); |
| d-c-043 | Bacteria(100); "Tenericutes"(100); Mollicutes(100); Mycoplasmatales(100); Mycoplasmataceae(100); Ureaplasma(100); |
| d-c-045 | Bacteria(100); "Actinobacteria"(100); Actinobacteria(100); Coriobacteriales (100); Coriobacteriaceae(100); Atopobium (100); |
| d-c-038 | Bacteria(100); "Actinobacteria"(100); Actinobacteria(100); Coriobacteriales (100); Coriobacteriaceae(100); unclassified(100); |
| d-c-047 | Bacteria(100); Firmicutes(100); Clostridia(100); Clostridiales(100); Clostridiales_Incertae_Sedis_XI(100); Anaerococcus(100); |
| d-c-054 | Bacteria(100); Firmicutes(100); Erysipelotrichia(100); Erysipelotrichales(100); Erysipelotrichaceae(100); Bulleidia(100); |

Note:
"Unclassified" genus represent novel genus not previously recorded in the database used for taxonomic classification, but newly identified by sequencing in this study.

TABLE 3B

Genus level classification of the differentially abundant (significantly decreased) bacterial taxa identified by comparing all 342 taxa in the 19 dilated vs. the 13 closed

| Taxon | Taxonomic classification of the identified taxon at the level of kingdom, phylum, class, family, order and genus with classification score (in brackets.) |
|---|---|
| d-c-067 | Bacteria(100); unclassified(100); unclassified(100); unclassified(100); unclassified(100); unclassified(100); |

TABLE 3B-continued

Genus level classification of the differentially abundant (significantly decreased) bacterial taxa identified by comparing all 342 taxa in the 19 dilated vs. the 13 closed

| Taxon | Taxonomic classification of the identified taxon at the level of kingdom, phylum, class, family, order and genus with classification score (in brackets.) |
|---|---|
| d-c-039 | Bacteria(100); "Synergistetes"(100); Synergistia(100); Synergistales(100); Synergistaceae(100); Jonquetella(100); |
| d-c-052 | Bacteria(100); Firmicutes(100); Bacilli(100); Lactobacillales(100); Aerococcaceae(100); Aerococcus(100); |
| d-c-074 | Bacteria(100); Firmicutes(100); Clostridia(100); Clostridiales(100); Clostridiales_Incertae_Sedis_XI(100); unclassified(100); |
| d-c-082 | Bacteria(100); "Actinobacteria"(100); Actinobacteria(100); Actinomycetales(100); Corynebacteriaceae(100); Corynebacterium(100); |
| d-c-092 | Bacteria(100); unclassified(100); unclassified(100); unclassified(100); unclassified(100); unclassified(100); |
| d-c-098 | Bacteria(100); unclassified(100); unclassified(100); unclassified(100); unclassified(100); unclassified(100); |

Note:
"Unclassified" genus represent novel genus not previously recorded in the database used for taxonomic classification, but newly identified by sequencing in this study.

TABLE 3C

Genus level classification data of the differentially abundant (significantly increased) bacterial taxa identified by comparing all 349 taxa in the 10 dilated vs. the 10 closed cervices (1:1 matched by gestational age at sample collection, matched to <2 weeks, normalized as ratio of total read count for each sample.).

| Taxon | Taxonomic classification of the identified taxon at the level of kingdom, phylum, class, family, order and genus with classification score (in brackets.) |
|---|---|
| d-c-012 | Bacteria(100); "Tenericutes"(100); Mollicutes(100); Mycoplasmatales(100); Mycoplasmataceae(100); Mycoplasma(100); |
| d-c-030 | Bacteria(100); Firmicutes(100); Negativicutes(100); Selenomonadales(100); Veillonellaceae(100); Veillonella(100); |
| d-c-040 | Bacteria(100); "Actinobacteria"(100); Actinobacteria(100); Bifidobacteriales(100); Bifidobacteriaceae(100); Alloscardovia(100); |
| d-c-047 | Bacteria(100); Firmicutes(100); Clostridia(100); Clostridiales(100); Clostridiales_Incertae_Sedis_XI(100); Anaerococcus(100); |
| d-c-050 | Bacteria(100); "Actinobacteria"(100); Actinobacteria(100); Actinomycetales(100); Propionibacteriaceae(100); Propionimicrobium(100); |
| d-c-053 | Bacteria(100); "Actinobacteria"(100); Actinobacteria(100); Actinomycetales(100); Corynebacteriaceae(100); Corynebacterium(100); |
| d-c-068 | Bacteria(100); Firmicutes(100); Clostridia(91); Clostridiales(91); unclassified(91); unclassified(91); |
| d-c-071 | Bacteria(100); "Actinobacteria"(100); Actinobacteria(100); Actinomycetales(100); Actinomycetaceae(100); Actinobaculum(100); |
| d-c-072 | Bacteria(100); Firmicutes(100); Clostridia(100); Clostridiales(100); Incertae_Sedis_XI(100); Murdochiella(100); |
| d-c-081 | Bacteria(100); unclassified(100); unclassified(100); unclassified(100); unclassified(100); unclassified(100); |
| d-c-015 | Bacteria(100); Firmicutes(100); Negativicutes(100); Selenomonadales(100); Veillonellaceae(100); Megasphaera(98); |
| d-c-083 | Bacteria(100); Firmicutes(100); Clostridia(100); Clostridiales(100); unclassified(100); unclassified(100); |
| d-c-087 | Bacteria(100); Firmicutes(100); Clostridia(100); Clostridiales(100); Ruminococcaceae(100); Fastidiosipila(100); |
| d-c-088 | Bacteria(100); "Acidobacteria"(100); Acidobacteria_Gp1(100); Gp1(100); unclassified(100); unclassified(100); |
| d-c-105 | Bacteria(100); unclassified(100); unclassified(100); unclassified(100); unclassified(100); unclassified(100); |

Note:
"Unclassified" genus represent novel genus not previously recorded in the database used for taxonomic classification, but newly identified by sequencing in this study.

TABLE 3D

Genus level classification of the differentially abundant (significantly decreased) bacterial taxa identified by comparing all 349 taxa in the 10 dilated vs. the 10 closed cervices (1:1 matched by gestational age at sample collection, matched to <2 weeks, normalized as ratio of total read count for each sample.).

| Taxon | Taxonomic classification of the identified taxon at the level of kingdom, phylum, class, family, order and genus with classification score (in brackets.) |
|---|---|
| d-c-018 | Bacteria(100); Firmicutes(100); Bacilli(100); Lactobacillales(100); Lactobacillaceae(100); *Lactobacillus*(99); |
| d-c-052 | Bacteria(100); Firmicutes(100); Bacilli(100); Lactobacillales(100); Aerococcaceae(100); Aerococcus(100); |
| d-c-074 | Bacteria(100); Firmicutes(100); Clostridia(100); Clostridiales(100); Clostridiales_Incertae_Sedis_XI(100); unclassified(100); |
| d-c-076 | Bacteria(100); Firmicutes(100); Bacilli(100); Lactobacillales(100); Lactobacillaceae(100); *Lactobacillus*(100); |
| d-c-082 | Bacteria(100); "Actinobacteria"(100); Actinobacteria(100); Actinomycetales (100); Corynebacteriaceae(100); Corynebacterium(100); |

Note:
"Unclassified" genus represent novel genus not previously recorded in the database used for taxonomic classification, but newly identified by sequencing in this study.

TABLE 4A

Sequences of the 16S rRNA gene of bacterial taxa of the differentially abundant (significantly increased) bacterial taxa identified by comparing all 342 taxa in the 19 dilated vs. the 13 closed cervices (normalized by random subsampling).

| Taxon | 16S ribosomal RNA genomic sequence |
|---|---|
| d-c-019 | GGAGCGCAGGCGGTTTTTTAAGTCTGATGTGAAAGCCCTCGGCTTAACCGAGGAAGCGCATCGGAAACTGGGAAACTTGAGTGCAGAAGAGGACAGTGGAACTCCATGTGTAGCGGTGAAATGCGTAGATATATGGAAGAACACCAGTGGCGAAGGCGGCTGTCTGGTCTGTAACTGACGCT |
| d-c-030 | CGCGCGCAGGCGGACTAGCCAGTCAGTCTTAAAAGTTCGGGGCTTAACCCCGTGATGGGATTGAAACTACTAGTCTAGAGTATCGGAGAGGAAAGTGGAATTCCTAGTGTAGCGGTGAAATGCGTAGATATTAGGAAGAACACCAGTGGCGAAGGCGACTTTCTGGACGAACACTGACGCT |
| d-c-037 | GGCGCGCAGGCGGTTCGGTAAGTCTGTCTTAAAGTGCGGGCTTAACCCCGTGAGGGACGGAAACTGTCGAACTTGAGTGTCGGAGAGGAAAGCGGAATTCCTAGTGTAGCGGTGAAATGCGTAGATATTAGGAGGAACACCGGTGGCGAAAGCGGCTTTCTGGACGACAACTGACGCT |
| d-c-040 | AGATGAGATGGCGGTTTGTCGCGTCTGGTGTGAAAGTCCATCGCTTAACGGTGGATTGGCGCTGGGTACGGGCAGGCTAGAGTGTAGTAGGGGAGACTGGAATTCTCGGTGTAACGGTGGAATGTGTAGATATCGGGAAGAACACCAATGGCGAAGGCAGGTCTCTGGGCTATTACTGACGCT |
| d-c-043 | CGAGCGCAGGCGGGTTTGTAAGTTTGGTATTAAATCTAGATGCTTAACGTCTAGCTGTATCAAAAACTGTAAACCTAGAGTGTAGTAGGGAGTTGGGGAACTCCATGTGGAGCGGTAAAATGCGTAGATATATGGAAGAACACCGGTGGCGAAGGCGCCAACTTGGACTATCACTGACGCT |
| d-c-045 | CGCGCGTAGGCGGTCTGTTAGGTCAGGAGTCAAATCTGGGGGCTCAACCCCTATCCGCTCCTGATACCGGCAGGCTTGAGTCTGGTATGGGAAGGTGGAATTCCAAGTGTAGCGGTGAAATGCGCAGATATTTGGAAGAACACCAGTGGCGAAGGCGGCCTTCTGGGCCATGACTGACGCT |
| d-c-038 | CGCGCGCAGGCGGTTGCTCAAGCGGAACCTCTAATCTCGGGGCTTAACCTCGAGCCGGGTTCCGAACTGGACGACTCGAGTGCGGTAGAGGCAGATGGAATTCCCGGTGTAGCGGTGGAATGCGCAGATATCGGGAAGAACACCAACGGCGAAGGCAGTCTGCTGGGCCGTCACTGACGCT |
| d-c-047 | AGTACGTAGGCGGCCTAGTAAGTTAGAAGTGAAAGAATATAGCTCAACTATATAAAGCTTTTAAAACTGTTAGGCTTGAGAGATGAAAGGGAAAGTGGAATTCCTAGTGTAGCGGTGAAATGCGCAGATATTAGGAAGAATACCGGTGGCGAAGGCGACTTTCTGGTCATCATCTGACGCT |
| d-c-054 | GGTGCGTAGGCGGTCTGTTAAGTTCATGGTTAAATTTTGGGGCTCAACCCCATTGAGCCATGGATACTGGCAGACTAGAGTATTGGAGAGGCAAGCGGAATTCCATGTGTAGCGGTAAAATGCGTAGATATATGGAGGAACACCGGTGGCGAAGGCGGCTTGCTAGCCAAAGACTGACGCT | d-c-019 (SEQ ID NO: 3); d-c-030 (SEQ ID NO: 4); d-c-037 (SEQ ID NO: 5); d-c-040 (SEQ ID NO: 6); d-c-043 (SEQ ID NO: 7); d-c-045 (SEQ ID NO: 8); d-c-038 (SEQ ID NO: 9); d-c-047 (SEQ ID NO: 10); d-c-054 (SEQ ID NO: 11).

TABLE 4B

Sequences of the 16S rRNA gene of bacterial taxa of the differentially abundant (significantly decreased) bacterial taxa identified by comparing all 342 taxa in the 19 dilated vs. the 13 closed cervices.

| Taxon | 16S ribosomal RNA genomic sequence |
|---|---|
| d-c-067 | GGTGCGCAGGCGGCTTTACAAGTTGGATGTGAAATATTGTGGCTCAACCACAAACGTGCAT<br>CCAAAACTGCAAAGCTTGAGTTAAGGAGAGGTAAGTGGAATTCCTGGTGTAGCGGTGGAAT<br>GCGTAGATATCAGGAGGAATACCGGTGGCGAAGGCGACTTACTGGACTTAAACTGACGCT |
| d-c-039 | GGCGCGTAGGCGGAATGGCAAGTCAGCAAGTGAAAGCGTGGGGCTCAACCCCATGATGCG<br>GCTGAAACTGTTATTCTAGAGGCATGGAGAGGCAAACGGAATTCCCGGTGTAGCGGTGAAA<br>TGCGTAGATATCGGGAAGAACACCAGTGGCGAAGGCGGTTTGCTGGCCATGAACTGACGC<br>T |
| d-c-052 | TGGGCGCAGGCGGTTTCTTAAGTCTGATGTGAAAGCCCACGGCTTAACCGTGGAAGTGCAT<br>TGGAAACTGGGGAACTTGAGTACAGAAGAGGAAAGTGGAACTCCATGTGTAGCGGTGAAT<br>GCGTAGATATATGGAAGAACACCAGTGGCGAAGGCGACTTTCTGGTCTGTCACTGACGCT |
| d-c-074 | CGTTCGCAGGCGGCAATGCAAGTCTCGTGTGAAAGGCAAGGGCTCAACCCTTGTAAGCAC<br>AAGAAACTGCATAGCTTGAGTAGTGGAGAGGCAAGTGGAATTCCTAGTGTAGCGGTGAAAT<br>GCGTAGATATTAGGAGGAATACCGGTGGCGAAGGCGACTTGCTGGACACAAACTGACGCT |
| d-c-082 | GGCTCGTAGGTGGTTTGTCGCGTCGTCTGTGAAATTCCGGGGCTTAACTCCGGGCGTGCA<br>GGCGATACGGGCATAACTTGAGTACTGTAGGGGAGACTGGAATTCCTGGTGTAGCGGTGA<br>AATGCGCAGATATCAGGAGGAACACCGGTGGCGAAGGCGGGTCTCTGGGCAGTAACTGAC<br>GCT |
| d-c-092 | CGCGTGTAGGCGGATTCTCAAGTTGGATGTGAAACCCCTTGGCTAAACTGAGGGCTTGCAT<br>TCAAAACTGAGGACCTTGAGTATCAGAGGGGAAAGTGGAATTCCTGGTGGAGCGGTAAAAT<br>GCGTAGAGATCAGGAGGAACACCGGTGGCGAAGGCGACTTTCTGGCTGACAACTGACGCT |
| d-c-098 | TGTGTGTAGGTGGCGTGATTAGTCGTTTGTGAAAGATCCGAGCTTAACTTGGAAAACGCGA<br>ACGAAACGGTCATGCTTGAGTATGTGAGAGGTAAGCAGAACTCATGGTGTAGGGGTGAAAT<br>CCGTTGATATCATGGGGAATACCAAAAGCGAAGGCAGCTTACTGGCACATTACTGACACT | d-c-067 (SEQ ID NO: 12); d-c-039 (SEQ ID NO: 13); d-c-052 (SEQ ID NO: 14); d-c-074 (SEQ ID NO: 15); d-c-082 (SEQ ID NO: 16); d-c-092 (SEQ ID NO: 17); d-c-098 (SEQ ID NO: 18).

TABLE 4C

Sequence of the 16S rRNA gene of bacterial taxa of the differentially abundant (significantly increased bacterial taxa identified by comparing all 349 taxa in the 10 dilated vs. the 10 closed cervices (1:1 matched by gestational age at sample collection, matched to <2 weeks, normalized as ratio of total read count for each sample).

| Taxon | 16S ribosomal RNA genomic sequence |
|---|---|
| d-c-012 | GGTTCGTAGGCTGTTTGTTAAGTCTGGAGTTAAATCCCGGGGCTCAACCCCGGCTCGCTTT<br>GGATACTAGCAAACTAGAGTTAGATAGAGGTAAGCGGAATTCCATGTGAAGCGGTGAAATG<br>CGTAGATATATGGAAGAACACCAAAGGCGAAGGCAGCTTACTGGGTCTATACTGACGCT |
| d-c-030 | CGCGCGCAGGCGGACTAGCCAGTCAGTCTTAAAAGTTCGGGGCTTAACCCCGTGATGGGA<br>TTGAAACTACTAGTCTAGAGTATCGGAGAGGAAAGTGGAATTCCTAGTGTAGCGGTGAAAT<br>GCGTAGATATTAGGAAGAACACCAGTGGCGAAGGCGACTTTCTGGACGAACACTGACGCT |
| d-c-040 | AGATGAGATGGCGGTTTGTCGCGTCTGGTGTGAAAGTCCATCGCTTAACGGTGGATTGGC<br>GCTGGGTACGGGCAGGCTAGAGTGTAGTAGGGGAGACTGGAATTCTCGGTGTAACGGTGG<br>AATGTGTAGATATCGGGAAGAACACCAATGGCGAAGGCAGGTCTCTGGGCTATTACTGACG<br>CT |
| d-c-047 | AGTACGTAGGCGGCCTAGTAAGTTAGAAGTGAAAGAATATAGCTCAACTATATAAAGCTTTT<br>AAAACTGTTAGGCTTGAGAGATGAAAGGGAAAGTGGAATTCCTAGTGTAGCGGTGAAATGC<br>GCAGATATTAGGAAGAATACCGGTGGCGAAGGCGACTTTCTGGTCATCATCTGACGCT |
| d-c-050 | GGCTTGTAGGCGGTTTGTCGCGTCGAAAGTGTAAACTCAGTGCTTAACGCTGAGCCTGCTT<br>TCGATACGGGCTGACTAGAGGAAGGTAGGGGAGAATGGAATTCCCGGTGGAGCGGTGGAA<br>TGCGCAGATATCGGAGGAACACCAGTGGCGAAGGCGGTTCTCTGGACCTTTCCTGACGC |
| d-c-053 | CGCTCGTAGGTGGTGTGTTGCGTCGTCTGTGTAATCCAGGGGCTTAACTTTTGGTTGGCAG<br>GCGATACGGGCATTGCTTGAGTGCTGTAGGGGAGACTGGAATTCCTGGTGTAGCGGTGAA<br>ATGCGCAGATATCAGGAGGAACACCGATGGCGAAGGCAGGTCTCTGGGCAGTTACTGACG |
| d-c-068 | TGAGCGTAGGCGGCAGTACAAGTCGGGAGTGAAAACTCGGGGCTCAACCCCGAGACTGCT<br>CTCGAAACTGTACAGCTAGAGTGCAGGATGGGCAGGCGGAATTCCTGGTGTAGCGGTGAA<br>ATGCGTAGATATCAGGAGGAACACCGGTGGCGAAGGCGGCCTGCTGGACTGTAACTGACG<br>CT |

TABLE 4C-continued

Sequence of the 16S rRNA gene of bacterial taxa of the differentially
abundant (significantly increased bacterial taxa identified by comparing
all 349 taxa in the 10 dilated vs. the 10 closed cervices (1:1 matched by
gestational age at sample collection, matched to <2 weeks, normalized as
ratio of total read count for each sample).

| Taxon | 16S ribosomal RNA genomic sequence |
|---|---|
| d-c-071 | GGCTTGTAGGCGGCTTGTTGCGCCTGCTGTGAAAACGCGGGGCTTAACTTCGCGCGTGCA GTGGGTACGGGCAGGCTTGAGTGTGGTAGGGGTGACTGGAATTCCAGGTGTAGCGGTGG AATGCGCAGATATCTGGAGGAACACCGATGGCGAAGGCAGGTCACTGGGCCATTACTGAC GCT |
| d-c-072 | GGTACGTAGGCGGTTTGTTAAGTTTGGCGTTAAATCACGGGGCTCAACCCCGTTCAGCGTT GAAAACTGGCAAACTTGAGTAGTAGAGGGGACAGTGGAATTCCTAGTGTAGCGGTGAAATG CGTAGAGATTAGGAAGAATACCGGTGGCGAAGGCGACTGTCTGGATACATACTGACGCT |
| d-c-081 | GGTGTGTAGGCGGTTATATTAGTCATTTGTTAAATCCTCGGGCTTAACCCGAGAATCGCGA GCGAAACGGTATAACTAGAAAGTGTGAGGGGTGTACAGAACTCATGGTGTAGGGGTGAAAT CCGTTGATATCATGGGGAATACCAAAAGCGAAGGCAGTACACTGGCACATATTTGACGCT |
| d-c-015 | TGCGCGCAGGCGGTTCGGTAAGTCTGTCTTAAAAGTGCGGGGCTTAACCCCGTGAGGGGA CGGAAACTGTCGAACTTGAGTGTCGGAGAGGAAAGCGGAATTCCTAGTGTAGCGGTGAAAT GCGTAGATATTAGGAGGAACACCGGTGGCGAAAGCGGCTTTCTGGACGACAACTGACGCT |
| d-c-083 | GGTTCGCAGGCGGAATAACAAGTCAGATGTGAAAGGCATGGGCTCAACCCATGTAAGCATT TGAAACTGTAATTCTTGAGAAGTGGAGAGGTAAGTGGAATTCCTAGTGTAGCGGTGAAATG CGTAGATATTAGGAGGAATACCTGTGGCGAAGGCGACTTACTGGACACAAATCTGACGCT |
| d-c-087 | CGCGTGTAGGCGGCACTGTAAGTCAGATGTGAAATCTCCCGGCTCAACCGGGAGCGTGCA TCTGATACTGCAATGCTTGAGTGATAGAGGGGAAAGCGGAATTCCTAGTGTAGCGGTAAAA TGCGTAGATATTAGGAGGAACACCAGTGGCGAAGGCGGCTTTCTGGCTATTAACTGACGCT |
| d-c-088 | GGTGCGTAGGCGGTTCGGTAAGTCTTGTGTGAAATCTTCAGGCTCAACTTGAAGTCTGCAC GAGAAACTGCCGGGCTTGAGTGTGGGAGAGGTGAGTGGAATTTCCGGTGTAGCGGTGAAA TGCGTAGATATCGGAAGGAACACCTGTGGCGAAAGCGGCTCACTGGACCACAACTGACGC T |
| d-c-105 | GGTGTGTAGGTGGTTATGTTAGTCTCCTTTCAAAGCTCCCGGCCTAACCGGGAAAAGGGAG GGGAAACGGCACAACTAGAGGATGCGAGGGGTCTGTGGAACTCATGGAGTAGGGGTGAAA TCCGTTGATATCATGGGGAACACCAAAAAGCGAAGGCAGCAGACTGGCGCATTCCTGACAC T | d-c-012 (SEQ ID NO: 19); d-c-030 (SEQ ID NO: 20); d-c-040 (SEQ ID NO: 21); d-c-047 (SEQ ID NO: 22); d-c-050 (SEQ ID NO: 23); d-c-053 (SEQ ID NO: 24); d-c-068 (SEQ ID NO: 25); d-c-071 (SEQ ID NO: 26); d-c-072 (SEQ ID NO: 27); d-c-081 (SEQ ID NO: 28); d-c-015 (SEQ ID NO: 29); d-c-083 (SEQ ID NO: 30); d-c-087 (SEQ ID NO: 31); d-c-088 (SEQ ID NO: 32); d-c-105 (SEQ ID NO: 33).

TABLE 4D

Sequences of the 16S rRNA gene of bacterial taxa differentially
abundant (significantly decreased) bacterial taxa identified by
comparing all 349 taxa in the 10 dilated vs. the 10 closed cervices
(1:1 matched by gestational age at sample collection, matched to <2
weeks, normalized as ratio of total read count for each sample.).

| Taxon | 16S ribosomal RNA genomic sequence |
|---|---|
| d-c-018 | CGAGTGCAGGCGGTTTTCTAAGTCTGATGTGAAAGCCTTCGGCTTAACCGGAGAAGTGCAT CGGAAACTGGATAACTTGAGTGCAGAAGAGGGTAGTGGAACTCCATGTGTAGCGGTGGAAT GCGTAGATATATGGAAGAACACCAGTGGCGAAGGCGGCTACCTGGTCTGCAACTGACGCT |
| d-c-052 | TGGGCGCAGGCGGTTTCTTAAGTCTGATGTGAAAGCCCACGGCTTAACCGTGGAAGTGCAT TGGAAACTGGGGAACTTGAGTACAGAAGAGGAAAGTGGAACTCCATGTGTAGCGGTGGAAT GCGTAGATATATGGAAGAACACCAGTGGCGAAGGCGACTTTCTGGTCTGTCACTGACGCT |
| d-c-074 | CGTTCGCAGGCGGCAATGCAAGTCTCGTGTGAAAGGCAAGGGCTCAACCCTTGTAAGCAC AAGAAACTGCATAGCTTGAGTAGTGGAGAGGCAAGTGGAATTCCTAGTGTAGCGGTGAAAT GCGTAGATATTAGGAGGAATACCGGTGGCGAAGGCGACTTGCTGGACACAAACTGACGCT |
| d-c-076 | TGAGCGCAGGCGGTTTTTTAAGTCTGATGTGAAAGCCTTCGGCTTAACCGGAGAAGTGCAT CGGAAACTGGGGAGACTTGAGTGCAGAAGAGGACAGTGGAACTCCATGTGTAGCGGTGGAA TGCGTAGATATATGGAAGAACACCAGTGGCGAAGGCGGCTGTCTAGTCTGTAACTGACGCT |

TABLE 4D-continued

Sequences of the 16S rRNA gene of bacterial taxa differentially abundant (significantly decreased) bacterial taxa identified by comparing all 349 taxa in the 10 dilated vs. the 10 closed cervices (1:1 matched by gestational age at sample collection, matched to <2 weeks, normalized as ratio of total read count for each sample.).

| Taxon | 16S ribosomal RNA genomic sequence |
| --- | --- |
| d-c-082 | GGCTCGTAGGTGGTTTGTCGCGTCGTCTGTGAAATTCCGGGGCTTAACTCCGGGCGTGCAGGCGATACGGGCATAACTTGAGTACTGTAGGGGAGACTGGAATTCCTGGTGTAGCGGTGAATGCGCAGATATCAGGAGGAACACCGGTGGCGAAGGCGGGTCTCTGGGCAGTAACTGACGCT | d-c-018 (SEQ ID NO: 34); d-c-052 (SEQ ID NO: 35); d-c-074 (SEQ ID NO: 36); d-c-076 (SEQ ID NO: 37); d-c-082 (SEQ ID NO: 38).

TABLE 4E

Species level classification by BLAST alignment to the 16S rRNA database of NCBI. Differentially abundant (significantly increased) bacterial taxa identified by comparing all 342 taxa in the 19 dilated vs. the 13 closed cervices (normalized by random subsampling) were aligned.

| Taxon | Top BLAST match | NCBI GenBank accession number | BLAST alignment score | Expect value | Identity of aligned sequence | Gaps |
| --- | --- | --- | --- | --- | --- | --- |
| d-c-019 | *Lactobacillus casei* ATCC 334 strain ATCC 334 16S ribosomal RNA, complete sequence | NR_075032.1 | 335 | 4.00E−92 | 181/181(100%) | 0/181(0%) |
| | *Lactobacillus paracasei* subsp. *paracasei* strain NBRC 15889 16S ribosomal RNA gene, partial sequence | NR_113337.1 | 335 | 4.00E−92 | 181/181(100%) | 0/181(0%) |
| | *Lactobacillus casei* strain NBRC 15883 16S ribosomal RNA gene, partial sequence | NR_113333.1 | 335 | 4.00E−92 | 181/181(100%) | 0/181(0%) |
| | *Lactobacillus paracasei* strain ATCC 25302 16S ribosomal RNA gene, partial sequence | NR_117987.1 | 335 | 4.00E−92 | 181/181(100%) | 0/181(0%) |
| | *Lactobacillus paracasei* subsp. *tolerans* strain NBRC 15906 16S ribosomal RNA gene, partial sequence | NR_041054.1 | 335 | 4.00E−92 | 181/181(100%) | 0/181(0%) |
| | *Lactobacillus casei* strain ATCC 393 16S ribosomal RNA gene, partial sequence | NR_041893.1 | 335 | 4.00E−92 | 181/181(100%) | 0/181(0%) |
| | *Lactobacillus casei* strain JCM 1134 16S ribosomal RNA gene, complete sequence | NR_115534.1 | 335 | 4.00E−92 | 181/181(100%) | 0/181(0%) |
| | *Lactobacillus paracasei* subsp. *paracasei* strain R094 16S ribosomal RNA gene, partial sequence | NR_025880.1 | 335 | 4.00E−92 | 181/181(100%) | 0/181(0%) |
| | *Lactobacillus zeae* strain RIA 482 16S ribosomal RNA gene, partial sequence | NR_037122.1 | 335 | 4.00E−92 | 181/181(100%) | 0/181(0%) |
| d-c-030 | *Veillonella montpellierensis* strain ADV 281.99 16S ribosomal RNA gene, partial sequence | NR_028839.1 | 335 | 4.00E−92 | 181/181(100%) | 0/181(0%) |
| d-c-037 * | *Megasphaera cerevisiae* strain DSM 20462 16S ribosomal RNA gene, partial sequence | NR_113307.1 | 265 | 6.00E−71 | 169/181(93%) | 3/181(1%) |
| | *Megasphaera cerevisiae* strain VTT-E-85230 16S ribosomal RNA gene, complete sequence | NR_044650.1 | 265 | 6.00E−71 | 169/181(93%) | 3/181(1%) |
| d-c-040 | *Alloscardovia omnicolens* strain CCUG 31649 16S ribosomal RNA gene, complete sequence | NR_042583.1 | 322 | 3.00E−88 | 174/174(100%) | 0/174(0%) |
| d-c-043 | *Ureaplasma urealyticum* serovar 10 str. ATCC 33699 strain ATCC 33699 16S ribosomal RNA, complete sequence | NR_102836.1 | 335 | 4.00E−92 | 181/181(100%) | 0/181(0%) |
| | *Ureaplasma parvum* serovar 3 str. ATCC 700970 strain ATCC 700970 16S ribosomal RNA, complete sequence | NR_074176.1 | 335 | 4.00E−92 | 181/181(100%) | 0/181(0%) |
| | *Ureaplasma parvum* serovar 3 strain ATCC 27815 16S ribosomal RNA gene, complete sequence | NR_074762.1 | 335 | 4.00E−92 | 181/181(100%) | 0/181(0%) |
| | *Ureaplasma parvum* serovar 3 strain ATCC 27815 16S ribosomal RNA gene, partial sequence | NR_027532.1 | 335 | 4.00E−92 | 181/181(100%) | 0/181(0%) |
| | *Ureaplasma urealyticum* serovar 8 strain ATCC 27618 16S ribosomal RNA gene, partial sequence | NR_041710.1 | 335 | 4.00E−92 | 181/181(100%) | 0/181(0%) |
| d-c-045 | *Atopobium vaginae* strain DSM 15829 16S ribosomal RNA gene, partial sequence | NR_117757.1 | 307 | 1.00E−83 | 176/181(97%) | 0/181(0%) |
| | *Atopobium vaginae* strain 961*00022/98 16S ribosomal RNA gene, partial sequence | NR_029349.1 | 307 | 1.00E−83 | 176/181(97%) | 0/181(0%) |
| d-c-038 * | *Parvibacter caecicola* strain NR06 16S ribosomal RNA gene, partial sequence | NR_117374.1 | 257 | 1.00E−68 | 167/181(92%) | 0/181(0%) |
| d-c-047 | *Anaerococcus senegalensis* strain JC48 16S ribosomal RNA gene, partial sequence | NR_118220.1 | 333 | 2.00E−91 | 180/180(100%) | 0/180(0%) |
| d-c-054 | *Bulleidia extructa* strain W1219 16S ribosomal RNA gene, partial sequence | NR_028773.1 | 302 | 4.00E−82 | 175/181(97%) | 0/181(0%) |

Notes:
* represents taxon with sequence identity <97% as any known species and may represent novel, previously unreported, species, which are now identified by sequencing in this study.

TABLE 4F

Species level classification by BLAST alignment to the 16S rRNA database of NCBI. Differentially abundant (significantly decreased) bacterial taxa identified by comparing all 342 taxa in the 19 dilated vs. the 13 closed cervices.

| Taxon | Top BLAST match | NCBI GenBank accession number | BLAST alignment score | Expect value | Identity of aligned sequence | Gaps |
|---|---|---|---|---|---|---|
| d-c-074 * | *Eubacterium aggregans* strain SR12 16S ribosomal RNA gene, partial sequence | NR_024926.1 | 176 | 3E-44 | 112/120(93%) | 2/120(1%) |
|  | *Acetobacterium bakii* strain DSM 8239 16S ribosomal RNA gene, partial sequence | NR_026329.1 | 176 | 3E-44 | 112/120(93%) | 2/120(1%) |
|  | *Eubacterium barkeri* strain ATCC 25849 16S ribosomal RNA gene, complete sequence | NR_044661.1 | 176 | 3E-44 | 112/120(93%) | 2/120(1%) |
| d-c-039 | *Jonquetella anthropi* strain ADV 126 16S ribosomal RNA gene, partial sequence | NR_044215.1 | 337 | 1E-92 | 182/182(100%) | 0/182(0%) |
| d-c-052 | *Aerococcus urinae* ACS-120-V-Col10a strain ACS-120-V-Col10a 16S ribosomal RNA, complete sequence | NR_074879.1 | 335 | 4E-92 | 181/181(100%) | 0/181(0%) |
| d-c-067 | [*Bacteroides*] *coagulans* strain EUH 581-73 16S ribosomal RNA gene, partial sequence | NR_104900.1 | 337 | 1E-92 | 182/182(100%) | 0/182(0%) |
|  | [*Bacteroides*] *coagulans* strain JCM 12528 16S ribosomal RNA gene, partial sequence | NR_113066.1 | 337 | 1E-92 | 182/182(100%) | 0/182(0%) |
| d-c-082 | *Corynebacterium lactis* strain RW2-5 16S ribosomal RNA gene, partial sequence | NR_104996.1 | 337 | 1E-92 | 182/182(100%) | 0/182(0%) |
|  | *Corynebacterium amycolatum* strain CCUG 35685 16S ribosomal RNA gene, partial sequence | NR_117605.1 | 337 | 1E-92 | 182/182(100%) | 0/182(0%) |
|  | *Corynebacterium amycolatum* 16S ribosomal RNA gene, partial sequence | NR_117030.1 | 337 | 1E-92 | 182/182(100%) | 0/182(0%) |
|  | *Corynebacterium freneyi* strain ISPB 6695110 16S ribosomal RNA gene, partial sequence | NR_042025.1 | 337 | 1E-92 | 182/182(100%) | 0/182(0%) |
|  | *Corynebacterium xerosis* strain DSM 20743 16S ribosomal RNA gene, partial sequence | NR_119180.1 | 337 | 1E-92 | 182/182(100%) | 0/182(0%) |
|  | *Corynebacterium xerosis* strain ATCC 373 16S ribosomal RNA gene, partial sequence | NR_026213.1 | 337 | 1E-92 | 182/182(100%) | 0/182(0%) |
|  | *Corynebacterium amycolatum* strain S160 16S ribosomal RNA gene, complete sequence | NR_026215.1 | 337 | 1E-92 | 182/182(100%) | 0/182(0%) |
| d-c-092 * | *Desulfococcus oleovorans* Hxd3 strain Hxd3 16S ribosomal RNA, complete sequence | NR_075012.1 | 126 | 3E-29 | 84/92(91%) | 0/92(0%) |
|  | *Desulfosalsimonas propionicica* strain PropA 16S ribosomal RNA gene, partial sequence | NR_115678.1 | 126 | 3E-29 | 84/92(91%) | 0/92(0%) |
| d-c-098 * | Uncultured bacterium clone F64Q2U401BWA69 16S ribosomal RNA gene, partial sequence | HQ145117.1 | 252 | 1E-36 | 166/181(92%) | 0/181(0%) |

Notes:
* represents taxon with sequence identity <97% as any known sequences and may represent novel, previously unreported, species, which are now identified by sequencing in this study.

TABLE 4G

Species level classification by BLAST alignment to the 16S rRNA database of NCBI. Differentially abundant (significantly increased) bacterial taxa identified by comparing all 349 taxa in the 10 dilated vs. the 10 closed cervices (1:1 matched by gestational age at sample collection, matched to <2 weeks, normalized as ratio of total read count for each sample.) were aligned.

| Taxon | Top BLAST match | NCBI GenBank accession number | BLAST alignment score | Expect value | Identity of aligned sequence | Gaps |
|---|---|---|---|---|---|---|
| d-c-012 | *Mycoplasma hominis* strain NBRC 14850 16S ribosomal RNA gene, partial sequence | NR_113679.1 | 333 | 2.00E-91 | 180/180(100%) | 0/180(0%) |
|  | *Mycoplasma hominis* strain PG21 16S ribosomal RNA gene, complete sequence | NR_041881.1 | 333 | 2.00E-91 | 180/180(100%) | 0/180(0%) |
| d-c-030 | *Veillonella montpellierensis* strain ADV 281.99 16S ribosomal RNA gene, partial sequence | NR_028839.1 | 335 | 4.00E-92 | 181/181(100%) | 0/180(0%) |
| d-c-040 | *Alloscardovia omnicolens* strain CCUG 31649 16S ribosomal RNA gene, complete sequence | NR_042583.1 | 322 | 3.00E-88 | 174/174(100%) | 0/174(0%) |
| d-c-047 | *Anaerococcus senegalensis* strain JC48 16S ribosomal RNA gene, partial sequence | NR_118220.1 | 333 | 2.00E-91 | 180/180(100%) | 0/180(0%) |
| d-c-050 | *Propionimicrobium lymphophilum* strain JCM 5829 16S ribosomal RNA gene, partial sequence | NR_114337.1 | 335 | 4.00E-92 | 181/181(100%) | 0/180(0%) |
| d-c-081 * | Uncultured bacterium clone MTS53 16S ribosomal RNA gene, partial sequence | JQ781443.1 | 250 | 4.00E-63 | 165/180(92%) | 0/180(0%) |
| d-c-053 | *Corynebacterium pyruviciproducens* strain 06-1773O 16S ribosomal RNA gene, partial sequence | NR_116569.1 | 337 | 1.00E-92 | 182/182(100%) | 0/182(0%) |

TABLE 4G-continued

Species level classification by BLAST alignment to the 16S rRNA database of NCBI. Differentially abundant (significantly increased) bacterial taxa identified by comparing all 349 taxa in the 10 dilated vs. the 10 closed cervices (1:1 matched by gestational age at sample collection, matched to <2 weeks, normalized as ratio of total read count for each sample.) were aligned.

| Taxon | Top BLAST match | NCBI GenBank accession number | BLAST alignment score | Expect value | Identity of aligned sequence | Gaps |
|---|---|---|---|---|---|---|
| d-c-015 * | *Megasphaera cerevisiae* strain DSM 20462 16S ribosomal RNA gene, partial sequence | NR_113307.1 | 278 | 7.00E−75 | 170/180(94%) | 0/180(0%) |
| | *Megasphaera cerevisiae* strain VTT-E-85230 16S ribosomal RNA gene, complete sequence | NR_044650.1 | 278 | 7.00E−75 | 170/180(94%) | 0/180(0%) |
| d-c-088 | *Acidipila rosea* strain AP8 16S ribosomal RNA gene, partial sequence | NR_113179.1 | 309 | 3.00E−84 | 177/182(97%) | 0/182(0%) |
| d-c-072 | *Murdochiella asaccharolytica* strain WAL 1855C 16S ribosomal RNA gene, partial sequence | NR_116331.1 | 331 | 6.00E−91 | 180/181(99%) | 0/181(0%) |
| d-c-105 * | Uncultured bacterium clone Ovdat63c11 16S ribosomal RNA gene, partial sequence | JF295520.1 | 237 | 3.00E−59 | 165/183(90%) | 1/183(0%) |
| | Uncultured bacterium clone GASP-WB2W3_D02 16S ribosomal RNA gene, partial sequence | EF074306.1 | 237 | 3.00E−59 | 165/183(90%) | 1/183(0%) |
| | Uncultured candidate division OD1 bacterium clone AKYH1067 16S ribosomal RNA gene, partial sequence | AY922093.1| | 237 | 3.00E−59 | 163/180(91%) | 1/180(0%) |
| d-c-068 * | *Howardella ureilytica* strain GPC 589 16S ribosomal RNA gene, complete sequence | NR_044022.2 | 268 | 5.00E−72 | 169/181(93%) | 0/181(0%) |
| d-c-071 | *Actinobaculum schaalii* strain CCUG 27420 16S ribosomal RNA gene, partial sequence | NR_116869.1 | 337 | 1.00E−92 | 182/182(100%) | 0/182(0%) |
| | *Actinobaculum schaalii* strain CCUG 27420 16S ribosomal RNA gene, complete sequence | NR_119244.1 | 337 | 1.00E−92 | 182/182(100%) | 0/182(0%) |
| | *Actinobaculum schaalii* strain B 5329 16S ribosomal RNA gene, partial sequence | NR_029339.1 | 337 | 1.00E−92 | 182/182(100%) | 0/182(0%) |
| d-c-083 | *Peptoniphilus duerdenii* strain WAL 18896 16S ribosomal RNA gene, partial sequence | NR_116346.1 | 337 | 1.00E−92 | 182/182(100%) | 0/182(0%) |
| d-c-087 | *Fastidiosipila sanguinis* strain CCUG 47711 16S ribosomal RNA gene, complete sequence | NR_042186.1 | 318 | 4.00E−87 | 179/182(98%) | 1/182(0%) |

Notes:
* represents taxon with sequence identity <97% as any known sequences and may represent novel, previously unreported, species, which are now identified by sequencing in this study.

TABLE 4H

Species level classification by BLAST alignment to the 16S rRNA database of NCBI. Differentially abundant (significantly decreased) bacterial taxa identified by comparing all 349 taxa in the 10 dilated vs. the 10 closed cervices (1:1 matched by gestational age at sample collection, matched to <2 weeks, normalized as ratio of total read count for each sample.) are aligned.

| Taxon | Top BLAST match | NCBI GenBank accession number | BLAST alignment score | Expect value | Identity of aligned sequence | Gaps |
|---|---|---|---|---|---|---|
| d-c-018 | *Lactobacillus fermentum* IFO 3956 strain IFO 3956 16S ribosomal RNA, complete sequence | NR_075033.1 | 335 | 4E−92 | 181/181(100%) | 0/181(0%) |
| | *Lactobacillus fermentum* strain CIP 102980 16S ribosomal RNA gene, complete sequence | NR_104927.1 | 335 | 4E−92 | 181/181(100%) | 0/181(0%) |
| | *Lactobacillus fermentum* strain NBRC 15885 16S ribosomal RNA gene, partial sequence | NR_113335.1 | 335 | 4E−92 | 181/181(100%) | 0/181(0%) |
| d-c-052 | *Aerococcus urinae* ACS-120-V-Col10a strain ACS-120-V-Col10a 16S ribosomal RNA, complete sequence | NR_074879.1 | 335 | 4E−92 | 181/181(100%) | 0/181(0%) |
| d-c-074 | *Eubacterium aggregans* strain SR12 16S ribosomal RNA gene, partial sequence | NR_024926.1| | 176 | 3E−44 | 112/120(93%) | 2/120(1%) |
| | *Acetobacterium bakii* strain DSM 8239 16S ribosomal RNA gene, partial sequence | NR_026329.1 | 176 | 3E−44 | 112/120(93%) | 2/120(1%) |
| | *Eubacterium barkeri* strain ATCC 25849 16S ribosomal RNA gene, complete sequence | NR_044661.1 | 176 | 3E−44 | 112/120(93%) | 2/120(1%) |
| d-c-076 | *Lactobacillus brevis* ATCC 367 strain ATCC 367 16S ribosomal RNA, complete sequence | NR_075024.1 | 335 | 4E−92 | 181/181(100%) | 0/181(0%) |
| | *Lactobacillus senmaizukei* strain NBRC 103853 16S ribosomal RNA gene, partial sequence | NR_114251.1 | 335 | 4E−92 | 181/181(100%) | 0/181(0%) |
| | *Lactobacillus brevis* strain ATCC 14869 16S ribosomal RNA gene, partial sequence | NR_116238.1 | 335 | 4E−92 | 181/181(100%) | 0/181(0%) |

TABLE 4H-continued

Species level classification by BLAST alignment to the 16S rRNA database of NCBI. Differentially abundant (significantly decreased) bacterial taxa identified by comparing all 349 taxa in the 10 dilated vs. the 10 closed cervices (1:1 matched by gestational age at sample collection, matched to <2 weeks, normalized as ratio of total read count for each sample.) are aligned.

| Taxon | Top BLAST match | NCBI GenBank accession number | BLAST alignment score | Expect value | Identity of aligned sequence | Gaps |
|---|---|---|---|---|---|---|
| d-c-082 | Corynebacterium lactis strain RW2-5 16S ribosomal RNA gene, partial sequence | NR_104996.1 | 337 | 1E-92 | 182/182(100%) | 0/182(0%) |
| | Corynebacterium amycolatum strain CCUG 35685 16S ribosomal RNA gene, partial sequence | NR_117605.1 | 337 | 1E-92 | 182/182(100%) | 0/182(0%) |
| | Corynebacterium amycolatum 16S ribosomal RNA gene, partial sequence | NR_117030.1 | 337 | 1E-92 | 182/182(100%) | 0/182(0%) |
| | Corynebacterium freneyi strain ISPB 6695110 16S ribosomal RNA gene, partial sequence | NR_042025.1 | 337 | 1E-92 | 182/182(100%) | 0/182(0%) |
| | Corynebacterium xerosis strain DSM 20743 16S ribosomal RNA gene, partial sequence | NR_119180.1 | 337 | 1E-92 | 182/182(100%) | 0/182(0%) |
| | Corynebacterium xerosis strain ATCC 373 16S ribosomal RN gene, partial sequence | NR_026213.1 | 337 | 1E-92 | 182/182(100%) | 0/182(0%) |
| | Corynebacterium amycolatum strain S160 16S ribosomal RNA gene, complete sequence | NR_026215.1 | 337 | 1E-92 | 182/182(100%) | 0/182(0%) |

Notes:

NA represents no significant BLAST match in the 16S ribosomal RNA database, and may represent novel, previously unreported, species, which are now identified by sequencing in this study.

* represents taxon with identity <97% and may represent novel, previously unreported, species, which are now identified by sequencing in this study.

TABLE 5A

Association between the proposed test, DIBT1, and adverse pregnancy or neonatal outcomes.
Sample with one or more selected taxa in the DIBT1 is considered as tested positive.

| Outcome | True positive | False positive | False negative | True negative | Fisher's exact p-value | Sensitivity | Specificity | Positive predicting value | Negative predicting value |
|---|---|---|---|---|---|---|---|---|---|
| Spontaneous preterm birth <28 wk * | 6 | 7 | 0 | 18 | 2.33E-03 | 100.0% | 72.0% | 46.2% | 100.0% |
| Spontaneous preterm birth <34 wk * | 7 | 6 | 0 | 18 | 6.53E-04 | 100.0% | 75.0% | 53.8% | 100.0% |
| Preterm birth <28 wk * | 8 | 5 | 2 | 16 | 5.72E-03 | 80.0% | 76.2% | 61.5% | 88.9% |
| Preterm birth <34 wk * | 13 | 0 | 3 | 15 | 3.22E-06 | 81.3% | 100.0% | 100.0% | 83.3% |
| Apgar score at 1 minute <7 | 7 | 1 | 2 | 3 | 2.17E-01 | 77.8% | 75.0% | 87.5% | 60.0% |
| Apgar score at 5 minute <7 | 6 | 2 | 1 | 4 | 1.03E-01 | 85.7% | 66.7% | 75.0% | 80.0% |
| Chorioamnioitis (clinical or pathological) | 5 | 3 | 2 | 3 | 5.92E-01 | 71.4% | 50.0% | 62.5% | 60.0% |
| Chorioamnioitis (clinical) | 2 | 6 | 1 | 4 | 1.00E+00 | 66.7% | 40.0% | 25.0% | 80.0% |
| Chorioamnioitis (pathological) | 1 | 7 | 1 | 4 | 1.00E+00 | 50.0% | 36.4% | 12.5% | 80.0% |
| Respiratory distress syndrome | 5 | 3 | 1 | 4 | 2.66E-01 | 83.3% | 57.1% | 62.5% | 80.0% |
| bronchopulmonary dysplasia | 2 | 4 | 1 | 4 | 1.00E+00 | 66.7% | 50.0% | 33.3% | 80.0% |
| Intraventricular hemorrhage * | 7 | 0 | 1 | 4 | 1.01E-02 | 87.5% | 100.0% | 100.0% | 80.0% |
| Neonatal death within 7 days after birth | 2 | 6 | 0 | 5 | 4.87E-01 | 100.0% | 45.5% | 25.0% | 100.0% |
| Neonatal sepsis | 3 | 4 | 1 | 4 | 5.76E-01 | 75.0% | 50.0% | 42.9% | 80.0% |

* $p < 0.05$

TABLE 5B

Association between the proposed test, DIBT2, and adverse pregnancy or neonatal outcomes.
Sample with one or more selected taxa in the DIBT2 is considered as tested positive.

| Outcome | True positive | False positive | False negative | True negative | Fisher's exact p-value | Sensitivity | Specificity | Positive predicting value | Negative predicting value |
|---|---|---|---|---|---|---|---|---|---|
| Spontaneous preterm birth <28 wk * | 6 | 7 | 0 | 18 | 2.3E-03 | 100.0% | 72.0% | 46.2% | 100.0% |
| Spontaneous preterm birth <34 wk * | 7 | 6 | 0 | 18 | 6.5E-04 | 100.0% | 75.0% | 53.8% | 100.0% |
| Preterm birth <28 wk * | 8 | 5 | 2 | 16 | 5.7E-03 | 80.0% | 76.2% | 61.5% | 88.9% |
| Preterm birth <34 wk * | 11 | 2 | 5 | 13 | 3.2E-03 | 68.8% | 86.7% | 84.6% | 72.2% |
| Apgar score at 1 minute <7 | 6 | 1 | 3 | 3 | 2.7E-01 | 66.7% | 75.0% | 85.7% | 50.0% |
| Apgar score at 5 minute <7 | 5 | 2 | 2 | 4 | 2.9E-01 | 71.4% | 66.7% | 71.4% | 66.7% |
| Chorioamnioitis (clinical or pathological) | 5 | 2 | 2 | 4 | 2.9E-01 | 71.4% | 66.7% | 71.4% | 66.7% |
| Chorioamnioitis (clinical) | 2 | 5 | 1 | 5 | 1.0E+00 | 66.7% | 50.0% | 28.6% | 83.3% |
| Chorioamnioitis (pathological) | 1 | 6 | 1 | 5 | 1.0E+00 | 50.0% | 45.5% | 14.3% | 83.3% |
| Respiratory distress syndrome | 5 | 2 | 1 | 5 | 1.0E-01 | 83.3% | 71.4% | 71.4% | 83.3% |
| bronchopulmonary dysplasia | 2 | 3 | 1 | 5 | 5.5E-01 | 66.7% | 62.5% | 40.0% | 83.3% |
| Intraventricular hemorrhage | 6 | 0 | 2 | 4 | 6.1E-02 | 75.0% | 100.0% | 100.0% | 66.7% |
| Neonatal death within 7 days after birth | 2 | 5 | 0 | 6 | 4.6E-01 | 100.0% | 54.5% | 28.6% | 100.0% |
| Neonatal sepsis | 3 | 3 | 1 | 5 | 5.5E-01 | 75.0% | 62.5% | 50.0% | 83.3% |

* P < 0.05

TABLE 6

Characteristics of participants in study B.

| | Short cervix group n = 11 | Normal-length cervix group n = 11 | P-value* |
|---|---|---|---|
| Gestational age at sample collection (weeks) | 20.8 +/- 2.37 | 19.4 +/- 3.07 | 0.2358 |
| Cervical length at sample collection (mm) | 20.2 +/- 9.16 | 34.5 +/- 5.04 | 0.0002 |
| Delivery outcome available | 10 | 10 | |
| Gestational age at delivery (weeks) | 35.8 +/- 6.00 | 39.7 +/- 1.34 | 0.0619 |
| Birthweight (g) | 2421 +/- 1012 | 3231 +/- 348 | 0.0277 |
| Cesarean delivery (n, %) | 1 (10%) | 6 (60%) | 0.0573 |
| Spontanoeus preterm birth <28 weeks (n, %) | 2 (20%) | 0 (0%) | 0.4737 |
| Spontanoeus preterm birth <34 weeks (n, %) | 3 (30%) | 0 (0%) | 0.2105 |
| Preterm birth <28 weeks (n, %) | 2 (20%) | 0 (0%) | 0.4737 |
| Preterm birth <34 weeks (n, %) | 3 (30%) | 0 (0%) | 0.2105 |

* T-test and Fisher exact test for continuous and discontinuous variables, respectively.

TABLE 7

Differentially abundant (significantly increased) bacterial taxa in the short cervix group,
compared with the normal-length cervix group. (normalized by random subsampling.
P-values are adjusted for multiple testing by the False Discovery Rate method

| Taxon | Mean relative abundance (short cervix group) | Standard error (short cervix group) | Mean relative abundance (normal-length cervix group) | Standard error (normal-length cervix group) | Fold-change (increased) | p-value | adjusted p-value* |
|---|---|---|---|---|---|---|---|
| s-n-006 | 4.2E-02 | 4.1E-02 | 6.0E-06 | 6.0E-06 | 6960 | 1.5E-02 | 4.4E-02 |
| s-n-007 | 9.1E-02 | 9.1E-02 | 0 | 0 | 6726 | 1.0E-03 | 4.5E-03 |
| s-n-008 | 4.1E-02 | 4.1E-02 | 0 | 0 | 3064 | 1.0E-03 | 4.5E-03 |
| s-n-012 | 6.2E-03 | 6.2E-03 | 0 | 0 | 462 | 1.0E-03 | 4.5E-03 |
| s-n-014 | 3.9E-03 | 3.9E-03 | 0 | 0 | 289 | 1.0E-03 | 4.5E-03 |
| s-n-022 | 7.9E-04 | 7.7E-04 | 0 | 0 | 58 | 1.0E-03 | 4.5E-03 |
| s-n-024 | 3.5E-04 | 3.5E-04 | 0 | 0 | 26 | 1.0E-03 | 4.5E-03 |
| s-n-025 | 2.0E-04 | 2.0E-04 | 0 | 0 | 15 | 1.0E-03 | 4.5E-03 |
| s-n-027 | 2.5E-04 | 2.3E-04 | 0 | 0 | 18 | 1.0E-03 | 4.5E-03 |
| s-n-028 | 3.4E-04 | 3.4E-04 | 0 | 0 | 25 | 1.0E-03 | 4.5E-03 |
| s-n-029 | 2.0E-04 | 2.0E-04 | 0 | 0 | 15 | 1.0E-03 | 4.5E-03 |
| s-n-030 | 1.3E-04 | 1.3E-04 | 0 | 0 | 10 | 1.0E-03 | 4.5E-03 |
| s-n-046 | 6.8E-05 | 6.8E-05 | 0 | 0 | 5 | 1.0E-03 | 4.5E-03 |
| s-n-054 | 8.0E-05 | 8.0E-05 | 0 | 0 | 6 | 1.0E-03 | 4.5E-03 |
| s-n-063 | 6.1E-05 | 6.1E-05 | 0 | 0 | 5 | 2.0E-03 | 8.2E-03 |

TABLE 7-continued

Differentially abundant (significantly increased) bacterial taxa in the short cervix group, compared with the normal-length cervix group. (normalized by random subsampling. P-values are adjusted for multiple testing by the False Discovery Rate method

| Taxon | Mean relative abundance (short cervix group) | Standard error (short cervix group) | Mean relative abundance (normal-length cervix group) | Standard error (normal-length cervix group) | Fold-change (increased) | p-value | adjusted p-value* |
|---|---|---|---|---|---|---|---|
| s-n-068 | 5.5E−05 | 5.5E−05 | 0 | 0 | 4 | 3.9E−03 | 1.4E−02 |
| s-n-071 | 4.3E−05 | 3.7E−05 | 0 | 0 | 3 | 1.6E−02 | 4.4E−02 |

TABLE 8

Genomic sequence of the 16S rRNA gene in the differentially abundant (significantly increased) bacterial taxa in the short cervix group, compared with the normal-length cervix group. (normalized by random subsampling.

| Taxon | Nucleotide sequence of the 16S ribosomal RNA gene |
|---|---|
| s-n-006 | AGGGCGCAGGCTGTTTCTTAAGTCTGATGTGAAAGCCCACGGCTTAACCGTGGAAGTGCATTGGAAACTGGGAAGCTTGAGTACAGAAGAGGAAAGTGGAACTCCATGTGTAGCGGTGGAATGCGTAGATATATGGAAGAACACCAGTGGCGAAAGCGACTTTCTGGTCTGTCACTGACGCTGA |
| s-n-007 | CGCTCGTAGGCGGTTCGTCGCGTCCGGTGTGAAAGTCCATCGCTTAACGGTGGATCCGCGCGGGTACGGGCGGGCTTGAGTGCGGTAGGGGAGACTGGAATTCCCGGTGTAACGGTGGAATGTGTAGATATCGGGAAGAACACCAATGGCGAAGGCAGGTCTCTGGGCCGTTACTGACGCTGA |
| s-n-008 | CGCGTGTAGGCGGCTAGATAAGTGTGATGTTTAAATCCAAGGCTTAACCTTGGGGTTCATTACAAACTGTTTAGCTTGAGTGCTGGAGAGGATAGTGGAATTCCTAGTGTAGCGGTAAAATGCGTAGATATTAGGAGGAACACCGGTGGCGAAGGCGGCTATCTGGACAGTAACTGACGCTGA |
| s-n-012 | CGAGCGTAGGCTGTTTGTTAAGCGTGTTGTGAAATGTAGGAGCTCAACTTTTAGATTGCAGCGCGAACTGGCAGACTTGAGTGCGCACAACGTAGGCGGAATTCATGGTGTAGCGGTGAAATGCTTAGATATCATGACGAACTCCGATTGCGAAGGCAGCTTACGGGAGCGCAACTGACGCTAA |
| s-n-014 | GGTACGTAGGCGGTTTTTAAGTCAGGTGTCAAAGCGTGGAGCTTAACTCCATTAAGCACTTGAAACTGAAAGACTTGAGTGAAGGAGAGGAAAGTGGAATTCCTAGTGTAGCGGTGAAATGCGTAGATATTAGGAGGAATACCGGTGGCGAAGGCGACTTTCTGACTTTTACTGACGCTCA |
| s-n-022 | TGTTCGCAGGCGGCAATGCAAGTCAGATGTAAAAGGCAAAGGCTCAACCTTTGTAAGCATCTGAAACTGTATAGCTTGAGAAGTGTAGAGGCAAGTGGAATTTTTAGTGTAGCGGTGAAATGCGTAGATATTAAAAAGAATACCGGTGGCGAAGGCGACTTGCTGGGCACAATCTGACGCTGA |
| s-n-024 | AGTACGTAGGCGGATAAGCAAGTTAGAAGTGAAATCCTATAGCTCAACTATAGTAAGCTTTTAAAACTGCTCATCTTGAGGTATGGAAGGGAAAGTGGAATTCCTAGTGTAGCGGTGAAATGCGCAGATATTAGGAGGAATACCGGTGGCGAAGGCGACTTTCTGGCCATAAACTGACGCTGA |
| s-n-025 | GGCGCGCAGGCGGTTTTTAAGTCGGTCTTAAAAGTGCGGGGCTTAACCCCGTGAGGGGACCGAAACTGGAAGACTTGAGTGTCGGAGAGGAAAGCGGAATTCCTAGTGTAGCGGTGAAATGCGTAGATATTAGGAGGAACACCGGTGGCGAAAGCGGCTTTCTGGACGACAACTGACGCTGA |
| s-n-027 | GGCGCGCAGGCGGTCACTTAAGTCCATCTTAGAAGTGCGGGGCTTAACCCCGTGATGGGATGGAAACTGGGAGACTGGAGTATCGGAGAGGAAAGTGGAATTCCTAGTGTAGCGGTGAAATGCGTAGATATTAGGAAGAACACCGGTGGCGAAGGCGACTTTCTGGACGAAAACTGACGCTGA |
| s-n-028 | GGTGCGTAGGTGGTCTTTCAAGTCGGTGGTTAAAGGCTACGGCTCAACCGTAGTTAGCCTCCGAAACTGGAAGACTTGAGTGCAGGAGAGGAAAGTGGAATTCCCAGTGTAGCGGTGAAATGCGTAGATATTGGGAGGAACACCAGTAGCGAAGGCGGCTTTCTGGACTGCAACTGACACTGA |

TABLE 8-continued

Genomic sequence of the 16S rRNA gene in the differentially abundant (significantly increased) bacterial taxa in the short cervix group, compared wtth the normal-length cervix group. (normalized by random subsampling.

| Taxon | Nucleotide sequence of the 16S ribosomal RNA gene |
|---|---|
| s-n-029 | GGCGTGTAGGCGGCTAGATAAGTGTGATGTTTAAATCCAAGGCTTAAACCTTGGG<br>GTTCATTACAAACTGTTTAGCTTGAGTGCTGGAGAGGATAGTGGAATTCCTAGTGT<br>AGCGGTAAAATGCGTAGATATTAGGAGGAACACCGGTGGCGAAGGCGGCTATCT<br>GGACAGTAACTGACGCTGA |
| s-n-030 | GGCGCGTAGGCGGTCTGTTAGGTCAGGAGTCAAATCTGGGGGCTCAACCCCTAT<br>CCGCTCCTGATACCGGCAGGCTTGAGTCTGGTATGGGAAGGTGGAATTCCAAGT<br>GTAGCGGTGAAATGCGCAGATATTTGGAAGAACACCAGTGGCGAAGGCGGCCTT<br>CTGGGCCATGACTGACGCTGA |
| s-n-046 | GATGAGATGGCGGTTCGTCGCGTCCGGTGTGAAAGTCCATCGCTTAACGGTGGA<br>TCCGCGCCGGGTACGGGCGGGCTTGAGTGCGGTAGGGGAGACTGGAATTCCCG<br>GTGTAACGGTGGAATGTGTAGATATCGGGAAGAACACCAATGGCGAAGGCAGGT<br>CTCTGGGCCGTTACTGACGCTGA |
| s-n-054 | GGCAGGTAGGTGGTCTGATTAGTCAATAGGTGAAATCCTCGGGCTTAACCCGAGA<br>AGTGCCTTTGAAACGGTCAGACTGGAGTACTCTAGAGGGTCGTGGAATTCCCGGT<br>GTAGCGGTGAAATGCGTAGAGATCGGGAGGAACACCAGAGGCGAAGGCGGCGA<br>CCTGGGGAGTGACTGACACTCA |
| s-n-063 | CGTGCGTAGGCGGTTCTTTAAGTCAGAGGTGAAAGACGGCAGCTTAACTGTCGCA<br>GTGCCTTTGATACTGAAGAACTTGAATTGGGTTGAGGAATGCGGAATGAGACAAG<br>TAGCGGTGAAATGCATAGATATGTCTCAGAACCCCGATTGCGAAGGCAGCATTCC<br>AAGCCTATATTGACGCTGA |
| s-n-068 | GGCAGGTAGGCTGTTTTGTAAGTCCGGCGTGAAATCCCAGAGCTCAACTCTGGAA<br>CTGCGTTGGAAACTACATGACTTGAGTATCGGAGAGGTTAGGGGAATTCTCGGTG<br>TAAGGGTGAAATCTGTAGATATCGAGAGGAACACCAGTGGCGAAGGCGCCTAACT<br>GGCCGATTACTGACGCTGA |
| s-n-071 | AGAGCGCAGGCGGTTTCTTAAGTCTGATGTGAAAGCCCTCGGCTCAACCGAGGAA<br>GGTCATTGGAAACTGGGGAACTTGAATGCAGAAGAGGAGAGTGGAATTCCATGTG<br>TAGCGGTGAAATGCGTAGATATATGGAGGAACACCAGTGGCGAAGGCGACTCTCT<br>GGTCTGTAATTGACGCTGA | s-n-006 (SEQ ID NO: 39); s-n-007 (SEQ ID NO: 40); s-n-008 (SEQ ID NO: 41); s-n-012 (SEQ ID NO: 42); s-n-014 (SEQ ID NO: 43); s-n-022 (SEQ ID NO: 44); s-n-024 (SEQ ID NO: 45); s-n-025 (SEQ ID NO: 46); s-n-027 (SEQ ID NO: 47); s-n-028 (SEQ ID NO: 48); s-n-029 (SEQ ID NO: 49); s-n-030 (SEQ ID NO: 50); s-n-046 (SEQ ID NO: 51); s-n-054 (SEQ ID NO: 52); s-n-063 (SEQ ID NO: 53); s-n-068 (SEQ ID NO: 54); s-n-071 (SEQ ID NO: 55).

TABLE 9

Species level classification of by BLAST alignment to the 16S rRNA database at NCBI. The 16S rRNA gene in the differentially abundant (significantly increased) bacterial taxa in the short cervix group, compared wtth the normal-length cervix group were aligned.

| Taxon | Description | Accession | Score | Expect | Identity | Gaps |
|---|---|---|---|---|---|---|
| s-n-006 | *Aerococcus christensenii* strain CCUG 28831 1 . . . | NR_044929.2 | 326 | 3E−89 | 180/183(98%) | 0/183(0%) |
| s-n-007 | *Bifidobacterium pseudolongum* subsp. *pseudolo* . . . | NR_043442.2 | 339 | 3E−93 | 183/183(100%) | 0/183(0%) |
|  | *Bifidobacterium pseudolongum* subsp. *globosum* . . . | NR_043441.2 | 339 | 3E−93 | 183/183(100%) | 0/183(0%) |
|  | *Bifidobacterium longum* strain ATCC 15707 16S . . . | NR_044691.2 | 339 | 3E−93 | 183/183(100%) | 0/183(0%) |
|  | *Bifidobacterium breve* ACS-071-V-Sch8b strain . . . | NR_102863.1 | 339 | 3E−93 | 183/183(100%) | 0/183(0%) |
|  | *Bifidobacterium longum* NCC2705 strain NCC270 . . . | NR_074744.1 | 339 | 3E−93 | 183/183(100%) | 0/183(0%) |
|  | *Bifidobacterium longum* subsp. *longum* strain . . . | NR_117506.1 | 339 | 3E−93 | 183/183(100%) | 0/183(0%) |
|  | *Bifidobacterium breve* strain DSM 20213 16S r . . . | NR_040783.1 | 339 | 3E−93 | 183/183(100%) | 0/183(0%) |
|  | *Bifidobacterium choerinum* strain Su 806 16S . . . | NR_037116.1 | 339 | 3E−93 | 183/183(100%) | 0/183(0%) |
|  | *Bifidobacterium longum* subsp. *infantis* strai . . . | NR_043437.1 | 339 | 3E−93 | 183/183(100%) | 0/183(0%) |
| s-n-008 | *Saccharofermentans acetigenes* strain P6 16S . . . | NR_115340.1 | 191 | 1E−48 | 107/109(98%) | 0/109(0%) |
| s-n-012 | *Prevotella amnii* strain CCUG 53648 16S ribos . . . | NR_042587.1 | 335 | 4E−92 | 182/183(99%) | 0/183(0%) |
| s-n-014* | *Parvimonas micra* strain JCM 12970 16S riboso . . . | NR_114338.1 | 298 | 6E−81 | 176/183(96%) | 1/183(0%) |
|  | *Parvimonas micra* strain 3119B 16S ribosomal . . . | NR_036934.1 | 298 | 6E−81 | 176/183(96%) | 1/183(0%) |
|  | *Parvimonas micra* strain ATCC 33270 16S ribos . . . | NR_114675.1 | 298 | 6E−81 | 176/183(96%) | 1/183(0%) |
| s-n-022 | *Peptoniphilus lacrimalis* strain CCUG 31350 1 . . . | NR_041938.1 | 337 | 1E−92 | 182/182(100%) | 0/182(0%) |
| s-n-024 | *Anaerococcus prevotii* strain DSM 20548 16S r . . . | NR_074575.1 | 337 | 1E−92 | 182/182(100%) | 0/182(0%) |
|  | *Anaerococcus tetradius* strain CCUG 46590 16S . . . | NR_041941.1 | 337 | 1E−92 | 182/182(100%) | 0/182(0%) |
|  | *Anaerococcus prevotii* strain CCUG 41932 16S . . . | NR_041939.1 | 337 | 1E−92 | 182/182(100%) | 0/182(0%) |

TABLE 9-continued

Species level classification of by BLAST alignment to the 16S rRNA database at NCBI. The 16S rRNA gene in the differentially abundant (significantly increased) bacterial taxa in the short cervix group, compared with the normal-length cervix group were aligned.

| Taxon | Description | Accession | Score | Expect | Identity | Gaps |
|---|---|---|---|---|---|---|
| s-n-025 * | *Megasphaera elsdenii* strain DSM 20460 16S ri . . . | NR_102980.1 | 283 | 2E-76 | 174/184(95%) | 2/184(1%) |
| | *Megasphaera elsdenii* strain DSM 20460 16S ri . . . | NR_113306.1 | 283 | 2E-76 | 174/184(95%) | 2/184(1%) |
| | *Megasphaera elsdenii* strain DSM 20460 16S ri . . . | NR_113305.1 | 283 | 2E-76 | 174/184(95%) | 2/184(1%) |
| s-n-027 | *Dialister micraerophilus* strain JCM 17567 16 . . . | NR_113356.1 | 337 | 1E-92 | 182/182(100%) | 0/182(0%) |
| | *Dialister micraerophilus* strain ADV 04.01 16 . . . | NR_041895.1 | 337 | 1E-92 | 182/182(100%) | 0/182(0%) |
| s-n-028 | *Peptostreptococcus anaerobius* strain NCTC 11 . . . | NR_042847.1 | 339 | 3E-93 | 183/183(100%) | 0/183(0%) |
| | *Peptostreptococcus anaerobius* strain ATCC 27 . . . | NR_118652.1 | 339 | 3E-93 | 183/183(100%) | 0/183(0%) |
| s-n-029 | *Saccharofermentans acetigenes* strain P6 16S . . . | NR_115340.1 | 191 | 1E-48 | 107/109(98%) | 0/109(0%) |
| s-n-030 | *Atopobium vaginae* strain DSM 15829 16S ribos . . . | NR_117757.1 | 309 | 3E-84 | 177/182(97%) | 0/182(0%) |
| | *Atopobium vaginae* strain 961*00022/98 16S ri . . . | NR_029349.1 | 309 | 3E-84 | 177/182(97%) | 0/182(0%) |
| s-n-046 | *Bifidobacterium pseudolongum* subsp. *pseudolo* . . . | NR_043442.2 | 326 | 3E-89 | 176/176(100%) | 0/176(0%) |
| | *Bifidobacterium pseudolongum* subsp. *globosum* . . . | NR_043441.2 | 326 | 3E-89 | 176/176(100%) | 0/176(0%) |
| | *Bifidobacterium longum* strain ATCC 15707 16S . . . | NR_044691.2 | 326 | 3E-89 | 176/176(100%) | 0/176(0%) |
| | *Bifidobacterium breve* ACS-071-V-Sch8b strain . . . | NR_102863.1 | 326 | 3E-89 | 176/176(100%) | 0/176(0%) |
| | *Bifidobacterium longum* NCC2705 strain NCC270 . . . | NR_074744.1 | 326 | 3E-89 | 176/176(100%) | 0/176(0%) |
| | *Bifidobacterium longum* subsp. *longum* strain . . . | NR_117506.1 | 326 | 3E-89 | 176/176(100%) | 0/176(0%) |
| | *Bifidobacterium breve* strain DSM 20213 16S r . . . | NR_040783.1 | 326 | 3E-89 | 176/176(100%) | 0/176(0%) |
| | *Bifidobacterium choerinum* strain Su 806 16S . . . | NR_037116.1 | 326 | 3E-89 | 176/176(100%) | 0/176(0%) |
| | *Bifidobacterium longum* subsp. *infantis* strai . . . | NR_043437.1 | 326 | 3E-89 | 176/176(100%) | 0/176(0%) |
| s-n-054 * | *Spiribacter salinus* strain M19-40 16S riboso . . . | NR_103952.1 | 167 | 2E-41 | 140/164(85%) | 3/164(1%) |
| s-n-063 | *Sphingobacterium spiritivorum* strain NBRC 14 . . . | NR_113707.1 | 327 | 7E-90 | 181/183(99%) | 0/183(0%) |
| | *Sphingobacterium spiritivorum* strain NCTC 11 . . . | NR_044077.1 | 327 | 7E-90 | 181/183(99%) | 0/183(0%) |
| | *Sphingobacterium spiritivorum* strain JCM 127 . . . | NR_115498.1 | 327 | 7E-90 | 181/183(99%) | 0/183(0%) |
| s-n-068 * | *Ochrobactrum pseudogrignonense* strain CCUG 3 . . . | NR_042589.1 | 172 | 4E-43 | 155/185(84%) | 4/185(2%) |
| s-n-071 | *Vagococcus fluvialis* strain M-29c 16S riboso . . . | NR_026489.1 | 339 | 3E-93 | 183/183(100%) | 0/183(0%) |

* indicates taxon with <97% nucleotide identity with known sequences and may represent novel, previously unreported, taxon.

TABLE 10

Association between the differentially abundant (significantly increased) taxa identified in Study B, and adverse pregnancy or neonatal outcomes. Sample with one or more selected taxa in the DIBT1 is considered as tested positive.

| Outcome | True positive | False positive | False negative | True negative | Fisher's exact p-value | Sensitivity | Specificity | Positive predicting value | Negative predicting value |
|---|---|---|---|---|---|---|---|---|---|
| Cervical length <29 mm | 9 | 0 | 2 | 11 | 0.00022 | 82% | 100% | 100% | 85% |
| Spontaneous preterm birth <28 wk | 2 | 6 | 0 | 12 | 0.15 | 100% | 67% | 25% | 100% |
| Spontaneous preterm birth <34 wk * | 3 | 5 | 0 | 12 | 0.049 | 100% | 71% | 38% | 100% |
| Preterm birth <28 wk | 2 | 6 | 0 | 12 | 0.15 | 100% | 67% | 25% | 100% |
| Preterm birth <34 wk * | 3 | 5 | 0 | 12 | 0.049 | 100% | 71% | 38% | 100% |

* P < 0.05

TABLE 11

Bacteria taxa comprising LA6

| taxon ID | taxon ID | SEQ ID NO. | Sequence | Abundance data | Taxonomic classification data | Species level classification by BLAST alignment to the 16S rRNA database | NCBI GenBank accession number | Percent Identity | |
|---|---|---|---|---|---|---|---|---|---|
| OTU #16 | sn-014 | 43 | Table 8 | Table 7 | Table 9 | *Parvimonas micra* | NR_114338.1 | 176/183 | 96% |
| OTU #56 | d-c-043 | 7 | Table 4A | Table 2A | Table 4E | *Ureaplasma urealyticum* or *Ureaplasma parvum* | NR_102836.1 or NR_074176.1 | 181/181 | 100% |
| OTU #42 | d-c-045 | 8 | Table 4A | Table 2A | Table 4E | *Atopobium vaginae* | NR_117757.1 | 176/181 | 97% |
| OTU #28 | sn-022 | 44 | Table 8 | Table 7 | Table 9 | *Peptoniphilus lacrimalis* | NR_041938.1 | 182/182 | 100% |
| OTU #47 | d-c-037 | 5 | Table 4A | Table 2A | Table 4E | *Megasphaera cerevisiae* | NR_113307.1 | 169/181 | 93% |
| OTU #40 | d-c-038 | 9 | Table 4A | Table 2A | Table 4E | *Parvibacter caecicola* | NR_117374.1 | 167/181 | 92% |

* Percent identity between the 16S rRNA gene nucleotide sequence of the bacterial taxon identified in our study and that of the nearest BLAST match as represented by the NCBI GenBank accession number.

Informal Sequence Listing

SEQ ID NO: 1
V4-V5 PCR forward primer (without Primer A Key sequence and MID
sequence at the 5' end of the primer)
AYT GGG YDT AAA GNG SEQ ID NO: 2
V4-V5 PCR reverse primer (without Primer B Key sequence at the 5'
end of the primer)
CCG TCA ATT YYT TTR AGT TT SEQ ID NO: 3
d-c-019 taxon from Table 4A-16S rRNA sequence.
GGAGCGCAGGCGGTTTTTTAAGTCTGATGTGAAAGCCCTCGGCTTAACCGAGGAAGCGCA
TCGGAAACTGGGAAACTTGAGTGCAGAAGAGGACAGTGGAACTCCATGTGTAGCGGTGAAA
TGCGTAGATATATGGAAGAACACCAGTGGCGAAGGCGGCTGTCTGGTCTGTAACTGACGCT SEQ ID NO: 4
d-c-030 taxon from Table 4A-16S rRNA sequence.
CGCGCGCAGGCGGACTAGCCAGTCAGTCTTAAAAGTTCGGGGCTTAACCCCGTGATGGGA
TTGAAACTACTAGTCTAGAGTATCGGAGAGGAAAGTGGAATTCCTAGTGTAGCGGTGAAAT
GCGTAGATATTAGGAAGAACACCAGTGGCGAAGGCGACTTTCTGGACGAACACTGACGCT SEQ ID NO: 5
d-c-037 taxon (OTU 47 taxon) from Table 4A-16S rRNA sequence.
GGCGCGCAGGCGGTTCGGTAAGTCTGTCTTAAAGTGCGGGCTTAACCCCGTGAGGGACGG
AAACTGTCGAACTTGAGTGTCGGAGAGGAAAGCGGAATTCCTAGTGTAGCGGTGAAATGCG
TAGATATTAGGAGGAACACCGGTGGCGAAAGCGGCTTTCTGGACGACAACTGACGCT SEQ ID NO: 6
d-c-040 taxon from Table 4A-16S rRNA sequence.
AGATGAGATGGCGGTTTGTCGCGTCTGGTGTGAAAGTCCATCGCTTAACGGTGGATTGGC
GCTGGGTACGGGCAGGCTAGAGTGTAGTAGGGGAGACTGGAATTCTCGGTGTAACGGTGG
AATGTGTAGATATCGGGAAGAACACCAATGGCGAAGGCAGGTCTCTGGGCTATTACTGACG
CT SEQ ID NO: 7
d-c-043 taxon (OTU 56 taxon) from Table 4A-16S rRNA sequence.
CGAGCGCAGGCGGGTTTGTAAGTTTGGTATTAAATCTAGATGCTTAACGTCTAGCTGTATCA
AAAACTGTAAACCTAGAGTGTAGTAGGGAGTTGGGGAACTCCATGTGGAGCGGTAAAATGC
GTAGATATATGGAAGAACACCGGTGGCGAAGGCGCCAACTTGGACTATCACTGACGCT SEQ ID NO: 8
d-c-045 taxon (OTU 42 taxon) from Table 4A-16S rRNA sequence.
CGCGCGTAGGCGGTCTGTTAGGTCAGGAGTCAAATCTGGGGGCTCAACCCCTATCCGCTC
CTGATACCGGCAGGCTTGAGTCTGGTATGGGAAGGTGGAATTCCAAGTGTAGCGGTGAAAT
GCGCAGATATTTGGAAGAACACCAGTGGCGAAGGCGGCCTTCTGGGCCATGACTGACGCT SEQ ID NO: 9
d-c-038 taxon (OTU 40 taxon) from Table 4A-16S rRNA sequence.
CGCGCGCAGGCGGTTGCTCAAGCGGAACCTCTAATCTCGGGGCTTAACCTCGAGCCGGGT
TCCGAACTGGACGACTCGAGTGCGGTAGAGGCAGATGGAATTCCCGGTGTAGCGGTGGAA
TGCGCAGATATCGGGAAGAACACCAACGGCGAAGGCAGTCTGCTGGGCCGTCACTGACGC
T SEQ ID NO: 10
d-c-047 taxon from Table 4A-16S rRNA sequence.
AGTACGTAGGCGGCCTAGTAAGTTAGAAGTGAAAGAATATAGCTCAACTATATAAAGCTTTT
AAAACTGTTAGGCTTGAGAGATGAAAGGGAAAGTGGAATTCCTAGTGTAGCGGTGAAATGC
GCAGATATTAGGAAGAATACCGGTGGCGAAGGCGACTTTCTGGTCATCATCTGACGCT SEQ ID NO: 11
d-c-054 taxon from Table 4A-16S rRNA sequence.
GGTGCGTAGGCGGTCTGTTAAGTTCATGGTTAAATTTTGGGGCTCAACCCCATTGAGCCAT
GGATACTGGCAGACTAGAGTATTGGAGAGGCAAGCGGAATTCCATGTGTAGCGGTAAAATG
CGTAGATATATGGAGGAACACCGGTGGCGAAGGCGGCTTGCTAGCCAAAGACTGACGCT SEQ ID NO: 12
d-c-067 taxon from Table 4B-16S rRNA sequence.
GGTGCGCAGGCGGCTTTACAAGTTGGATGTGAAATATTGTGGCTCAACCACAAACGTGCAT
CCAAAACTGCAAAGCTTGAGTTAAGGAGAGGTAAGTGGAATTCCTGGTGTAGCGGTGGAAT
GCGTAGATATCAGGAGGAATACCGGTGGCGAAGGCGACTTACTGGACTTAAACTGACGC SEQ ID NO: 13
d-c-039 taxon from Table 4B-16S rRNA sequence.
GGCGCGTAGGCGGAATGGCAAGTCAGCAAGTGAAAGCGTGGGGCTCAACCCCATGATGCG
GCTGAAACTGTTATTCTAGAGGCATGGAGAGGCAAACGGAATTCCCGGTGTAGCGGTGAAA
TGCGTAGATATCGGGAAGAACACCAGTGGCGAAGGCGGTTTGCTGGCCATGAACTGACGC
T -continued

```
Informal Sequence Listing

SEQ ID NO: 14
d-c-052 taxon from Table 4B-16S rRNA sequence.
TGGGCGCAGGCGGTTTCTTAAGTCTGATGTGAAAGCCCACGGCTTAACCGTGGAAGTGCAT
TGGAAACTGGGGAACTTGAGTACAGAAGAGGAAAGTGGAACTCCATGTGTAGCGGTGGAAT
GCGTAGATATATGGAAGAACACCAGTGGCGAAGGCGACTTTCTGGTCTGTCACTGACGCT SEQ ID NO: 15
d-c-074 taxon from Table 4B-16S rRNA sequence.
CGTTCGCAGGCGGCAATGCAAGTCTCGTGTGAAAGGCAAGGGCTCAACCCTTGTAAGCAC
AAGAAACTGCATAGCTTGAGTAGTGGAGAGGCAAGTGGAATTCCTAGTGTAGCGGTGAAAT
GCGTAGATATTAGGAGGAATACCGGTGGCGAAGGCGACTTGCTGGACACAAACTGACGCT SEQ ID NO: 16
d-c-082 taxon from Table 4B-16S rRNA sequence.
GGCTCGTAGGTGGTTTGTCGCGTCGTCTGTGAAATTCCGGGGCTTAACTCCGGGCGTGCA
GGCGATACGGGCATAACTTGAGTACTGTAGGGGAGACTGGAATTCCTGGTGTAGCGGTGA
AATGCGCAGATATCAGGAGGAACACCGGTGGCGAAGGCGGGTCTCTGGGCAGTAACTGAC
GCT SEQ ID NO: 17
d-c-092 taxon from Table 4B-16S rRNA sequence.
CGCGTGTAGGCGGATTCTCAAGTTGGATGTGAAACCCCTTGGCTAAACTGAGGGCTTGCAT
TCAAAACTGAGGACCTTGAGTATCAGAGGGGAAAGTGGAATTCCTGGTGGAGCGGTAAAAT
GCGTAGAGATCAGGAGGAACACCGGTGGCGAAGGCGACTTTCTGGCTGACAACTGACGCT SEQ ID NO: 18
d-c-098 taxon from Table 4B-16S rRNA sequence.
TGTGTGTAGGTGGCGTGATTAGTCGTTTGTGAAAGATCCGAGCTTAACTTGGAAAACGCGA
ACGAAACGGTCATGCTTGAGTATGTGAGAGGTAAGCAGAACTCATGGTGTAGGGGTGAAAT
CCGTTGATATCATGGGGAATACCAAAAGCGAAGGCAGCTTACTGGCACATTACTGACACT SEQ ID NO: 19
d-c-012 taxon from Table 4C-16S rRNA sequence.
GGTTCGTAGGCTGTTTGTTAAGTCTGGAGTTAAATCCCGGGGCTCAACCCCGGCTCGCTTT
GGATACTAGCAAACTAGAGTTAGATAGAGGTAAGCGGAATTCCATGTGAAGCGGTGAAATG
CGTAGATATATGGAAGAACACCAAAGGCGAAGGCAGCTTACTGGGTCTATACTGACGCT SEQ ID NO: 20
d-c-030 taxon from Table 4C-16S rRNA sequence.
CGCGCGCAGGCGGACTAGCCAGTCAGTCTTAAAAGTTCGGGGCTTAACCCCGTGATGGGA
TTGAAACTACTAGTCTAGAGTATCGGAGAGGAAAGTGGAATTCCTAGTGTAGCGGTGAAAT
GCGTAGATATTAGGAAGAACACCAGTGGCGAAGGCGACTTTCTGGACGAACACTGACGCT SEQ ID NO: 21
d-c-040 taxon from Table 4C-16S rRNA sequence.
AGATGAGATGGCGGTTTGTCGCGTCTGGTGTGAAAGTCCATCGCTTAACGGTGGATTGGC
GCTGGGTACGGGCAGGCTAGAGTGTAGTAGGGGAGACTGGAATTCTCGGTGTAACGGTGG
AATGTGTAGATATCGGGAAGAACACCAATGGCGAAGGCAGGTCTCTGGGCTATTACTGACG
CT SEQ ID NO: 22
d-c-047 taxon from Table 4C-16S rRNA sequence.
AGTACGTAGGCGGCCTAGTAAGTTAGAAGTGAAAGAATATAGCTCAACTATATAAAGCTTTT
AAAACTGTTAGGCTTGAGAGATGAAAGGGAAAGTGGAATTCCTAGTGTAGCGGTGAAATGC
GCAGATATTAGGAAGAATACCGGTGGCGAAGGCGACTTTCTGGTCATCATCTGACGCT SEQ ID NO: 23
d-c-050 taxon from Table 4C-16S rRNA sequence.
GGCTTGTAGGCGGTTTGTCGCGTCGAAAGTGTAAACTCAGTGCTTAACGCTGAGCCTGCTT
TCGATACGGGCTGACTAGAGGAAGGTAGGGGAGAATGGAATTCCCGGTGGAGCGGTGGAA
TGCGCAGATATCGGGAGGAACACCAGTGGCGAAGGCGGTTCTCTGGACCTTTCCTGACGC SEQ ID NO: 24
d-c-053 taxon from Table 4C-16S rRNA sequence.
CGCTCGTAGGTGGTGTGTTGCGTCGTCTGTGTAATCCAGGGGCTTAACTTTTGGTTGGCAG
GCGATACGGGCATTGCTTGAGTGCTGTAGGGGAGACTGGAATTCCTGGTGTAGCGGTGAA
ATGCGCAGATATCAGGAGGAACACCGATGGCGAAGGCAGGTCTCTGGGCAGTTACTGACG SEQ ID NO: 25
d-c-068 taxon from Table 4C-16S rRNA sequence.
TGAGCGTAGGCGGCAGTACAAGTCGGGAGTGAAAACTCGGGGCTCAACCCCGAGACTGCT
CTCGAAACTGTACAGCTAGAGTGCAGGATGGGCAGGCGGAATTCCTGGTGTAGCGGTGAA
ATGCGTAGATATCAGGAGGAACACCGGTGGCGAAGGCGGCCTGCTGGACTGTAACTGACG
CT
```

-continued

| Informal Sequence Listing |
|---|

SEQ ID NO: 26
d-c-071 taxon from Table 4C-16S rRNA sequence.
GGCTTGTAGGCGGCTTGTTGCGCCTGCTGTGAAAACGCGGGCTTAACTTCGCGCGTGCA
GTGGGTACGGGCAGGCTTGAGTGTGGTAGGGGTGACTGGAATTCCAGGTGTAGCGGTGG
AATGCGCAGATATCTGGAGGAACACCGATGGCGAAGGCAGGTCACTGGGCCATTACTGAC
GCT SEQ ID NO: 27
d-c-072 taxon from Table 4C-16S rRNA sequence.
GGTACGTAGGCGGTTTGTTAAGTTTGGCGTTAAATCACGGGGCTCAACCCCGTTCAGCGTT
GAAAACTGGCAAACTTGAGTAGTAGAGGGGACAGTGGAATTCCTAGTGTAGCGGTGAAATG
CGTAGAGATTAGGAAGAATACCGGTGGCGAAGGCGACTGTCTGGATACATACTGACGCT SEQ ID NO: 28
d-c-081 taxon from Table 4C-16S rRNA sequence.
GGTGTGTAGGCGGTTATATTAGTCATTTGTTAAATCCTCGGGCTTAACCCGAGAATCGCGA
GCGAAACGGTATAACTAGAAAGTGTGAGGGGTGTACAGAACTCATGGTGTAGGGGTGAAAT
CCGTTGATATCATGGGGAATACCAAAAGCGAAGGCAGTACACTGGCACATATTTGACGCT SEQ ID NO: 29
d-c-015 taxon from Table 4C-16S rRNA sequence.
TGCGCGCAGGCGGTTCGGTAAGTCTGTCTTAAAAGTGCGGGGCTTAACCCCGTGAGGGGA
CGGAAACTGTCGAACTTGAGTGTCGGAGAGGAAAGCGGAATTCCTAGTGTAGCGGTGAAAT
GCGTAGATATTAGGAGGAACACCGGTGGCGAAAGCGGCTTTCTGGACGACAACTGACGCT SEQ ID NO: 30
d-c-083 taxon from Table 4C-16S rRNA sequence.
GGTTCGCAGGCGGAATAACAAGTCAGATGTGAAAGGCATGGCTCAACCCATGTAAGCATT
TGAAACTGTAATTCTTGAGAAGTGGAGAGGTAAGTGGAATTCCTAGTGTAGCGGTGAAATG
CGTAGATATTAGGAGGAATACCTGTGGCGAAGGCGACTTACTGGACACAAATCTGACGCT SEQ ID NO: 31
d-c-087 taxon from Table 4C-16S rRNA sequence.
CGCGTGTAGGCGGCACTGTAAGTCAGATGTGAAATCTCCCGGCTCAACCGGGAGCGTGCA
TCTGATACTGCAATGCTTGAGTGATAGAGGGGAAAGCGGAATTCCTAGTGTAGCGGTAAAA
TGCGTAGATATTAGGAGGAACACCAGTGGCGAAGGCGGCTTTCTGGCTATTAACTGACGCT SEQ ID NO: 32
d-c-088 taxon from Table 4C-16S rRNA sequence.
GGTGCGTAGGCGGTTCGGTAAGTCTTGTGTGAAATCTTCAGGCTCAACTTGAAGTCTGCAC
GAGAAACTGCCGGGCTTGAGTGTGGGAGAGGTGAGTGGAATTTCCGGTGTAGCGGTGAAA
TGCGTAGATATCGGAAGGAACACCTGTGGCGAAAGCGGCTCACTGGACCACAACTGACGC
T SEQ ID NO: 33
d-c-105 taxon from Table 4C-16S rRNA sequence.
GGTGTGTAGGTGGTTATGTTAGTCTCCTTTCAAAGCTCCCGGCCTAACCGGGAAAAGGGAG
GGGAAACGGCACAACTAGAGGATGCGAGGGGTCTGTGGAACTCATGGAGTAGGGGTGAAA
TCCGTTGATATCATGGGGAACACCAAAAAGCGAAGGCAGCAGACTGGCGCATTCCTGACAC
T SEQ ID NO: 34
d-c-018 taxon from Table 4D-16S rRNA sequence.
CGAGTGCAGGCGGTTTTCTAAGTCTGATGTGAAAGCCTTCGGCTTAACCGGAGAAGTGCAT
CGGAAACTGGATAACTTGAGTGCAGAAGAGGGTAGTGGAACTCCATGTGTAGCGGTGGAAT
GCGTAGATATATGGAAGAACACCAGTGGCGAAGGCGGCTACCTGGTCTGCAACTGACGCT SEQ ID NO: 35
d-c-052 taxon from Table 4D-16S rRNA sequence.
TGGGCGCAGGCGGTTTCTTAAGTCTGATGTGAAAGCCCACGGCTTAACCGTGGAAGTGCAT
TGGAAACTGGGGAACTTGAGTACAGAAGAGGAAAGTGGAACTCCATGTGTAGCGGTGGAAT
GCGTAGATATATGGAAGAACACCAGTGGCGAAGGCGACTTTCTGGTCTGTCACTGACGCT SEQ ID NO: 36
d-c-074 taxon from Table 4D-16S rRNA sequence.
CGTTCGCAGGCGGCAATGCAAGTCTCGTGTGAAAGGCAAGGGCTCAACCCTTGTAAGCAC
AAGAAACTGCATAGCTTGAGTAGTGGAGAGGCAAGTGGAATTCCTAGTGTAGCGGTGAAAT
GCGTAGATATTAGGAGGAATACCGGTGGCGAAGGCGACTTGCTGGACACAAACTGACGCT SEQ ID NO: 37
d-c-076 taxon from Table 4D-16S rRNA sequence.
TGAGCGCAGGCGGTTTTTTAAGTCTGATGTGAAAGCCTTCGGCTTAACCGGAGAAGTGCAT
CGGAAACTGGGAGACTTGAGTGCAGAAGAGGACAGTGGAACTCCATGTGTAGCGGTGGAA
TGCGTAGATATATGGAAGAACACCAGTGGCGAAGGCGGCTGTCTAGTCTGTAACTGACGCT SEQ ID NO: 38
d-c-082 taxon from Table 4D-16S rRNA sequence.
GGCTCGTAGGTGGTTTGTCGCGTCGTCTGTGAAATTCCGGGGCTTAACTCCGGGCGTGCA
GGCGATACGGGCATAACTTGAGTACTGTAGGGGAGACTGGAATTCCTGGTGTAGCGGTGA
AATGCGCAGATATCAGGAGGAACACCGGTGGCGAAGGCGGGTCTCTGGGCAGTAACTGAC
GCT SEQ ID NO: 39
s-n-006 taxon from Table 8-nucleotide sequence of the 16S rRNA
gene.
AGGGCGCAGGCTGTTTCTTAAGTCTGATGTGAAAGCCCACGGCTTAACCGTGGAA
GTGCATTGGAAACTGGGAAGCTTGAGTACAGAAGAGGAAAGTGGAACTCCATGTG
TAGCGGTGGAATGCGTAGATATATGGAAGAACACCAGTGGCGAAAGCGACTTTCT
GGTCTGTCACTGACGCTGA SEQ ID NO: 40
s-n-007 taxon from Table 8-nucleotide sequence of the 16S rRNA
gene.
CGCTCGTAGGCGGTTCGTCGCGTCCGGTGTGAAAGTCCATCGCTTAACGGTGGA
TCCGCGCCGGGTACGGGCGGGCTTGAGTGCGGTAGGGGAGACTGGAATTCCCG
GTGTAACGGTGGAATGTGTAGATATCGGGAAGAACACCAATGGCGAAGGCAGGT
CTCTGGGCCGTTACTGACGCTGA SEQ ID NO: 41
s-n-008 taxon from Table 8-nucleotide sequence of the 16S rRNA
gene.
CGCGTGTAGGCGGCTAGATAAGTGTGATGTTTAAATCCAAGGCTTAACCTTGGGG
TTCATTACAAACTGTTTAGCTTGAGTGCTGGAGAGGATAGTGGAATTCCTAGTGTA
GCGGTAAAATGCGTAGATATTAGGAGGAACACCGGTGGCGAAGGCGGCTATCTG
GACAGTAACTGACGCTGA SEQ ID NO: 42
sn-012 taxon from Table 8-nucleotide sequence of the 16S rRNA
gene.
CGAGCGTAGGCTGTTTGTTAAGCGTGTTGTGAAATGTAGGAGCTCAACTTTTAGAT
TGCAGCGCGAACTGGCAGACTTGAGTGCGCACAACGTAGGCGGAATTCATGGTG
TAGCGGTGAAATGCTTAGATATCATGACGAACTCCGATTGCGAAGGCAGCTTACG
GGAGCGCAACTGACGCTAA SEQ ID NO: 43
s-n-014 taxon (OTU 16 taxon) from Table 8-nucleotide sequence of
the 16S rRNA gene.
GGTACGTAGGCGGTTTTTAAGTCAGGTGTCAAAGCGTGGAGCTTAACTCCATTAA
GCACTTGAAACTGAAAGACTTGAGTGAAGGAGAGGAAAGTGGAATTCCTAGTGTA
GCGGTGAAATGCGTAGATATTAGGAGGAATACCGGTGGCGAAGGCGACTTTCTG
GACTTTTACTGACGCTCA SEQ ID NO: 44
s-n-022 taxon (OTU 28 taxon) from Table 8-nucleotide sequence of
the 16S rRNA gene.
TGTTCGCAGGCGGCAATGCAAGTCAGATGTAAAAGGCAAAGGCTCAACCTTTGTA
AGCATCTGAAACTGTATAGCTTGAGAAGTGTAGAGGCAAGTGGAATTTTTAGTGTA
GCGGTGAAATGCGTAGATATTAAAAAGAATACCGGTGGCGAAGGCGACTTGCTGG
GCACAATCTGACGCTGA SEQ ID NO: 45
s-n-024 taxon from Table 8-nucleotide sequence of the 16S rRNA
gene.
AGTACGTAGGCGGATAAGCAAGTTAGAAGTGAAATCCTATAGCTCAACTATAGTAA
GCTTTTAAAACTGCTCATCTTGAGGTATGGAAGGGAAAGTGGAATTCCTAGTGTAG
CGGTGAAATGCGCAGATATTAGGAGGAATACCGGTGGCGAAGGCGACTTTCTGG
CCATAAACTGACGCTGA SEQ ID NO: 46
s-n-025 taxon from Table 8-nucleotide sequence of the 16S rRNA
gene.
GGCGCGCAGGCGGTTTTTTAAGTCGGTCTTAAAAGTGCGGGGCTTAACCCCGTG
AGGGGACCGAAACTGGAAGACTTGAGTGTCGGAGAGGAAAGCGGAATTCCTAGT
GTAGCGGTGAAATGCGTAGATATTAGGAGGAACACCGGTGGCGAAAGCGGCTTT
CTGGACGACAACTGACGCTGA

| Informal Sequence Listing |
|---|

SEQ ID NO: 47
s-n-027 taxon from Table 8-nucleotide sequence of the 16S rRNA
gene.
GGCGCGCAGGCGGTCACTTAAGTCCATCTTAGAAGTGCGGGGCTTAACCCCGTG
ATGGGATGGAAACTGGGAGACTGGAGTATCGGAGAGGAAAGTGGAATTCCTAGT
GTAGCGGTGAAATGCGTAGATATTAGGAAGAACACCGGTGGCGAAGGCGACTTTC
TGGACGAAAACTGACGCTGA SEQ ID NO: 48
s-n-028 taxon from Table 8-nucleotide sequence of the 16S rRNA
gene.
GGTGCGTAGGTGGTCTTTCAAGTCGGTGGTTAAAGGCTACGGCTCAACCGTAGTT
AGCCTCCGAAACTGGAAGACTTGAGTGCAGGAGAGGAAAGTGGAATTCCCAGTGT
AGCGGTGAAATGCGTAGATATTGGGAGGAACACCAGTAGCGAAGGCGGCTTTCT
GGACTGCAACTGACACTGA SEQ ID NO: 49
s-n-029 taxon from Table 8-nucleotide sequence of the 16S rRNA
gene.
GGCGTGTAGGCGGCTAGATAAGTGTGATGTTTAAATCCAAGGCTTAAACCTTGGG
GTTCATTACAAACTGTTTAGCTTGAGTGCTGGAGAGGATAGTGGAATTCCTAGTGT
AGCGGTAAAATGCGTAGATATTAGGAGGAACACCGGTGGCGAAGGCGGCTATCT
GGACAGTAACTGACGCTGA SEQ ID NO: 50
s-n-030 taxon from Table 8-nucleotide sequence of the 16S rRNA
gene.
GGCGCGTAGGCGGTCTGTTAGGTCAGGAGTCAAATCTGGGGGCTCAACCCCTAT
CCGCTCCTGATACCGGCAGGCTTGAGTCTGGTATGGGAAGGTGGAATTCCAAGT
GTAGCGGTGAAATGCGCAGATATTTGGAAGAACACCAGTGGCGAAGGCGGCCTT
CTGGGCCATGACTGACGCTGA SEQ ID NO: 51
s-n-046 taxon from Table 8-nucleotide sequence of the 16S rRNA
gene.
GATGAGATGGCGGTTCGTCGCGTCCGGTGTGAAAGTCCATCGCTTAACGGTGGA
TCCGCGCCGGGTACGGGCGGGCTTGAGTGCGGTAGGGGAGACTGGAATTCCCG
GTGTAACGGTGGAATGTGTAGATATCGGGAAGAACACCAATGGCGAAGGCAGGT
CTCTGGGCCGTTACTGACGCTGA SEQ ID NO: 52
s-n-054 taxon from Table 8-nucleotide sequence of the 16S rRNA
gene.
GGCAGGTAGGTGGTCTGATTAGTCAATAGGTGAAATCCTCGGGCTTAACCCGAGA
AGTGCCTTTGAAACGGTCAGACTGGAGTACTCTAGAGGGTCGTGGAATTCCCGGT
GTAGCGGTGAAATGCGTAGAGATCGGGAGGAACACCAGAGGCGAAGGCGGCGA
CCTGGGGAGTGACTGACACTCA SEQ ID NO: 53
s-n-063 taxon from Table 8-nucleotide sequence of the 16S rRNA
gene.
CGTGCGTAGGCGGTTCTTTAAGTCAGAGGTGAAAGACGGCAGCTTAACTGTCGCA
GTGCCTTTGATACTGAAGAACTTGAATTGGGTTGAGGAATGCGGAATGAGACAAG
TAGCGGTGAAATGCATAGATATGTCTCAGAACCCCGATTGCGAAGGCAGCATTCC
AAGCCTATATTGACGCTGA SEQ ID NO: 54
s-n-068 taxon from Table 8-nucleotide sequence of the 16S rRNA
gene.
GGCAGGTAGGCTGTTTTGTAAGTCCGGCGTGAAATCCCAGAGCTCAACTCTGGAA
CTGCGTTGGAAACTACATGACTTGAGTATCGGAGAGGTTAGGGGAATTCTCGGTG
TAAGGGTGAAATCTGTAGATATCGAGAGGAACACCAGTGGCGAAGGCGCCTAACT
GGCCGATTACTGACGCTGA SEQ ID NO: 55
s-n-071 taxon from Table 8-nucleotide sequence of the 16S rRNA
gene.
AGAGCGCAGGCGGTTTCTTAAGTCTGATGTGAAAGCCCTCGGCTCAACCGAGGAA
GGTCATTGGAAACTGGGGAACTTGAATGCAGAAGAGGAGAGTGGAATTCCATGTG
TAGCGGTGAAATGCGTAGATATATGGAGGAACACCAGTGGCGAAGGCGACTCTCT
GGTCTGTAATTGACGCTGA Informal Sequence Listing SEQ ID NO: 56
OTU #11 taxon-*Sneathia sanguinegens*-nucleotide sequence of the 16S rRNA gene.
CGCATCTAGGCGGTAAGACAAGTTGAAGGTGAAAACCTGTGGCTCAACCATAGGCT
TGCCTACAAAACTGTTGAACTAGAGTACTGGAAAGGTGGGTGGAACTACACGAGTA
GAGGTGAAATTCGTA

What is claimed is:

1. A method for reducing the risk of preterm birth, said method comprising:

(a) identifying a pregnant female human subject suitable to receive cerclage/pessary intervention by the process of i. detecting in a cervical swab sample or a cervical mucus sample taken from a pregnant female human subject who has been diagnosed with cervical insufficiency the level of each of bacteria taxa *Parvimonas micra*, *Ureaplasma urealyticum* or *Ureaplasma parvum*, *Atopobium vaginae*, *Peptoniphilus lacrimalis*, *Megasphaera cerevisiae*, and *Parvibacter caecicola*, wherein the level is determined by massively parallel sequencing (MPS) with Cumulative Sum Scaling (CSS) normalization; ii. detecting a $\log_{10}$(total of all bacteria taxa levels obtained in step i) no greater than 1.15; and iii. identifying the subject as suitable to receive cerclage/pessary intervention, and (b) treating the subject identified in step (a) by cerclage/pessary intervention, thereby reducing the risk of preterm birth in the subject.

2. The method of claim 1, wherein in step i the levels of at least 7, 8, 9, 10, 11, 12, 13, 14, 15, 16, 17, 18, 19 or 20 different bacteria taxa are detected.

3. The method of claim 1, wherein step (a) comprises a polynucleotide amplification assay, an assay involving polynucleotide sequence determination, or an assay involving sequence-specific probe/primer hybridization.

4. The method of claim 3, wherein the amplification assay is a polymerase chain reaction (PCR) assay.

5. The method of claim 4, wherein the PCR assay is a quantitative PCR assay or a reverse-transcriptase PCR assay.

6. The method of claim 1, further comprising extracting nucleic acids from the cervical swab sample or cervical mucus sample prior to step (a).

7. The method of claim 1, wherein step i further comprises:
    detecting in the cervical swab sample or a cervical mucus sample the level of bacteria belonging to at least one bacterial taxon selected from the group consisting of *Jonquetella anthropi, Aerococcus urinae*, and a bacterial taxon specified by a 16S rRNA nucleotide sequence set forth in any one of SEQ ID NOs:12-18 and 34-38.

* * * * *